US006242472B1

(12) United States Patent
Sekins et al.

(10) Patent No.: US 6,242,472 B1
(45) Date of Patent: Jun. 5, 2001

(54) METHODS FOR THE PULMONARY DELIVERY OF BIOLOGICAL AGENTS

(75) Inventors: K. Michael Sekins, San Diego, CA (US); Thomas H. Shaffer, Lansdowne; Marla R. Wolfson, Wyndmoor, both of PA (US)

(73) Assignee: Alliance Pharmaceutical Corp., San Diego, CA (US)

( * ) Notice: Subject to any disclaimer, the term of this patent is extended or adjusted under 35 U.S.C. 154(b) by 0 days.

(21) Appl. No.: 09/109,592

(22) Filed: Jul. 2, 1998

Related U.S. Application Data

(63) Continuation of application No. 08/479,615, filed on Jun. 7, 1995, now abandoned, which is a continuation of application No. 08/424,577, filed on Apr. 13, 1995, now Pat. No. 5,562,608, which is a continuation of application No. 07/920,153, filed on Jul. 27, 1992, now abandoned, which is a continuation of application No. 07/495,566, filed on Mar. 19, 1990, now abandoned, which is a continuation-in-part of application No. 07/399,943, filed on Aug. 28, 1989, now abandoned.

(51) Int. Cl.$^7$ .................................................. A01N 43/50
(52) U.S. Cl. ........................ 514/396; 514/759; 514/772; 514/653; 514/937
(58) Field of Search ................................. 514/396, 759, 514/937, 772, 653

(56) References Cited

U.S. PATENT DOCUMENTS

| | | |
|---|---|---|
| 3,975,512 | 8/1976 | Long . |
| 4,233,984 | 11/1980 | Walling . |
| 4,669,463 | 6/1987 | McConnell . |
| 4,740,103 | 4/1988 | Theeuwes . |
| 4,881,542 | 11/1989 | Schmidt et al. . |
| 4,955,375 | 9/1990 | Martinez . |
| 4,976,261 | 12/1990 | Gluck et al. . |
| 5,031,613 | 7/1991 | Smith et al. . |

FOREIGN PATENT DOCUMENTS

| | | |
|---|---|---|
| 2848636 | 5/1980 | (DE) . |
| 0074809 | 3/1983 | (EP) . |
| 0118850 | 4/1984 | (EP) . |
| 2214467 | 8/1974 | (FR) . |
| 84000686 | 3/1984 | (WO) . |
| 8602845 | 5/1986 | (WO) . |

OTHER PUBLICATIONS

Bogy, D.B. (1979) Drop formation in a circular liquid jet, Ann. Rev. Fluid. Mech. 11:207–228.
Bogy, D.B. (1979) Break–up of a liquid jet: third perturbation Cosserat solution. Phys. Fluids 22(2):224–230.
Chemical Abstracts, vol. 71, No. 3, 1985, Columbus, Ohio, US; Abstract No. 115853, Abstract & Tumori vol. 71, No. 3, 1985, Hild, Peter, et al., Perfluorocarbon (FDA20) and extracorporeal circuit of isolated extremity perfusion.
Chemical Abstracts, 105:(5), Columbus, Ohio, US; Abstract No. 353341a, Abstract & Eur. Surg. Res. vol. 17(5), 1985, p. 301–309, J.L. Skibba, et al., Canine liver isolation–perfusion at normo–and–hyperthermic temperatures with perfluorochemical emulsion (Fluosol–43).
Crane, L., et al. (1964) The effect of machanical vibration on the break–up of a cylindrical water jet in air. Brit. J. Appl. Phys. 15:743–751.
Curry, S.A. and H. Portig (1977) Scale model of an ink jet. IBM J. Res. Devel., pp. 10–20.
Dabora, E.K. (1967) Production of monodisperse sprays. The Review of Scientific Instruments 38(4):502–506.
Keeling, M.R. (1981) Ink Jet Printing, Phys. Technol. 12:196–203.
Levanoni, M. (1977) Study of fluid flow through scaled–up ink jet nozzles, IBM J. Res. Develop., pp. 56–68.
Marmor, J.B., et al. (1982) Clinical studies wth ultrasound–induced hyperthermia, Stn. File Supplier & File Medline AN=83088921 (Karlsruhe) Natl. Cancer Inst. Monogr., vol. 61. pp. 333–337, Abstract.
Sakai, T., and M. Hoshino (1980) Production of uniform droplets by longitudinal vibration of audio frequency. Journ. Chem. Engineering Japan 13(4):263–268.
Sekins, K.M. et al. (1988) Lung cancer hyperthermia via ultrasound and PFC liquids. 78–80, $5^{th}$ International Symposium on Hyperthermic Oncology, Kyoto, Japan.
Sekins, K.M., et al. (1989) Intracavitary and external ultrasound bythermia of the lung using PFC liquids. Pp. 81–82, Ninth Annual Meeting of the North American Hyperthermia Group, Seattle, Washington.
Sekins, K.M., et al. (1989) Intracavity and external ultrasound hyperthermia of the lung using PFC liquids, Abstract Ad–5, p. 9, Abstracts of papers for the Thirty–Seventh Annual Meeting of the Radiation Research Society. Ninth Annual Meeting of the North American Hyperthermia Group, Seattle, Washington, Mar. 18–23, 1989.
Wissema, J.G. and G.A. Davies (1966) The formation of uniformly sized drops by vibration–atomization. The Canadian Journal of Chemical Engineering, 47:530–535.
Wolfson, M.R. and T.H. Shaffer (1990) Pulmonary administration of drugs (PAD): A new approach for drug delivery using liquid ventilation. FASEB Journal 4(4):A11005.

*Primary Examiner*—Rebecca Cook
(74) *Attorney, Agent, or Firm*—Knobbe, Martens, Olson & Bear, LLP

(57) ABSTRACT

Methods of delivering a therapeutic or diagnostic agent in a perfluorochemical liquid carrier are provided. In preferred embodiments, the disclosed methods use compositions in the form of an emulsion or a dispersion for delivery of a biological agent to the pulmonary air passages.

50 Claims, 29 Drawing Sheets

METHODS FOR THE PULMONARY DELIVERY OF BIOLOGICAL AGENTS

This application is a continuation of Ser. No. 08/479,615, filed Jun. 7, 1995, abandoned which is a continuation of Ser. No. 08/424,577, filed Apr. 13, 1995 and now U.S. Pat. No. 5,562,608, which is a continuation of Ser. No. 07/920,153, filed Jul. 27, 1992, abandoned, which is a continuation of Ser. No. 07/495,566, filed Mar. 19, 1990 now abandoned, which is a continuation-in-part of Ser. No. 07/399,943, filed Aug. 28, 1989, abandoned.

This invention was made with government support under Small Business Innovation Research Program Grant No. 1 R43 CA48611-01 awarded by the Public Health Service, Department of Health and Human Services. The government has certain rights in the invention.

TECHNICAL FIELD

The invention relates to methods and means for introducing liquids into the pulmonary system of patients for the treatment of pulmonary and/or systemic disease, conditions and/or abnormalities such as, for example, to effect hyperthermic treatment and augmented radiotherapy and chemotherapy of lung cancer. This invention also relates to the employment of liquid as a means of delivering, through the pulmonary air passages of a patient, biological agents.

BACKGROUND OF THE INVENTION

In the United States there has been a steady rise in the age-adjusted national death rate from pulmonary related diseases. The overwhelmingly predominant contributor to this trend is long cancer. Currently about 8% of all deaths in the industrialized world are attributed to lung cancer. In the United States, an estimated 155,000 new cases of lung cancer are currently diagnosed each year, and about 142,000 will die of the disease, about 1 death every 4 minutes! Only about 10% of the patients currently diagnosed with lung cancer will survive beyond 5 years.

Lung cancer, or bronchial carcinoma, refers strictly to tumors arising from the major airways (bronchi) and pulmonary parenchyma (bronchioles, alveoli, and supporting tissue), as opposed to those metastasizing from other sites. The four major forms of lung cancer, squamous cell carcinoma (SCC), adenocarcinoma (AC), large cell anaplastic carcinoma (LCAC), and small cell anaplastic carcinoma (SCAC), account for 98% of pulmonary malignancies. Although lung cancer can occur anywhere in the lungs, about three-quarters of primary lung cancers occur in and/or on the bronchial walls within the first three bronchial generations, i.e., near or proximal to the hilus, the region where the airways and major vessels enter and leave each lung. A smaller percentage occur in more distal areas of the parenchyma. Many tumors occur near the carina, at the junction of the right and left bronchi with the trachea, presumedly due to increased deposition of inhaled carcinogens. Squamous cell carcinoma tumors, the most common histological type, making up 30–40% of lung tumors, arise inside the surface layer of the bronchial wall and then invade the wall and adjacent structures. Squamous cell carcinomas tend to be relatively localized with less tendency than the other lung cancer tumors to metastasize. Adenocarcinoma tumors, also comprising 30–40% of lung cancers, occur in the mid- to outer third of the lung in about three-quarters of the cases. Adenocarcinomas tend to metastasize widely and frequently to other lung sites, the liver, bone, kidney, and brain. Small cell cancer, accounting for about 20% of all lung cancer, is the most aggressively metastatic and rapidly growing, and can begin near the hilus or in the lung periphery. Large cell tumors account for only a few percent of lung cancer and can occur anywhere in the lung. “Local failure,” where primary tumors spread to mediastinal lymph nodes, pleura, adrenal glands, bone, and brain, is common with adenocarcinoma, small cell anaplastic carcinoma, and large cell anaplastic carcinoma, and less so in squamous cell carcinoma.

The current “curative” treatment for lung cancer is surgery, but the option for such a cure is given to very few. Only about 20% of lung cancer is resectable, and out of this number less than half will survive five years. Radiation therapy (RT) is the standard treatment for inoperable non-small cell cancer, and chemotherapy (alone or with radiation therapy) is the treatment of choice for small cell and other lung cancer with wide metastasis. Patients with clinically localized but technically unresectable tumors represent a major problem for the radiotherapist, accounting for an estimated 40% of all lung cancer cases.

Adjunctive hyperthermia, the use of deep heating modalities to treat tumors, is being used increasingly to augment the therapeutic efficacy of radiotherapy and chemotherapy in cancer treatment. It has been estimated that eventually “hyperthermia will be indispensable for 20 to 25% of all cancer patients” [1; see the appended listing of literature citations]. Hyperthermia clinical research is increasingly showing the importance of using specialized heating equipment to treat specific anatomical locations and sites rather than devices with more general-purpose heating capabilities. Unfortunately, current hyperthermia devices are ill-suited to providing deep, localized heating of lung cancer. Because of this limitation, very few applications of localized lung hyperthermia have been recorded in the literature [2].

Kapp [8] has shown that, in terms of absolute numbers of patients (15,000 in 1987), more lung cancer patients would benefit from effective local hyperthermia than in any other cancer category, with the possible exception of prostate carcinoma. Because of the present difficulty of heating tumors locally in a controlled fashion in the center of the thorax, the techniques most commonly attempted for lung cancer hyperthermia to date have been whole-body hyperthermia (WBH), and radio-frequency (RF) heating of locoregional lung areas [2,9].While whole-body hyperthermia has produced some encouraging results in combination with chemotherapy, the technique is unsatisfactory since it produces significant systemic toxicity and mortality, and because the thermal dose is limited due to long induction times (warmup) and the need to maintain core temperature below 42° C. The electromagnetic (EM) approaches to lung heating have also been disappointing, due to the unpredictability of the heating patterns produced, the difficulty of measuring intratumoral temperatures in electromagnetic fields, the propensity of radio-frequency heating to preferentially heat superficial fat, and because of the physical inability of electromagnetic modalities to produce small focal volumes. The modern microwave body-surrounding array systems also suffer from difficulties associated with localization and predictability of heating, thermometry artifacts, and heat spikes at fat muscle interfaces.

Because of its characteristically small wavelengths, therapeutic ultrasound has the best capability for providing local heating in the body of all the conventionally used hyperthermia modalities. Focused and unfocused ultrasound beams are routinely used clinically to successfully provide localized hyperthermia to many tumors residing in soft tissues and organs. However, the presence of air in the lung has precluded this valuable energy source from being applied to lung hyperthermia.

Thus, the need for a means of delivering safe, effective, and well-tolerated localized heating to lung tumors is clear. The invention solves this problem, in the preferred embodiment, by an unconventional use of "breathable liquids" (e.g., perfluorocarbon liquids) and therapeutic ultrasound.

As used herein, the phrase "breathable liquids" refers to liquids which have the ability to deliver oxygen into, and to remove carbon dioxide from, the pulmonary system (i.e., the lungs) of patients. Examples of breathable liquids include, but are not limited to, saline, silicon and vegetable oils, perfluorochemicals, and the like. One of the presently-preferred breathable liquids is perfluorocarbon liquids.

Perfluorocarbon (also referred to herein as "PFC") liquids are derived from common organic compounds by the replacement of all carbon-bound hydrogen atoms with fluorine atoms. They are clear, colorless, odorless, nonflammable, and essentially insoluble in water. They have extremely high dielectric strength and resistivity. They are denser than water and soft tissue, have low surface tension and, for the most part, low viscosity. Perfluorocarbon liquids appear to have the lowest sound speeds of all liquids and are also unique in their high affinity for gases, dissolving up to 20 times as much $O_2$ and over three times as much $CO_2$ as water. Like other highly inert carbon-fluorine materials which are widely used in medicine (e.g., in drugs, Teflon implants, blood oxygenator membranes, etc.), perfluorocarbon liquids are extremely nontoxic and biocompatible. For a review, see: Biro, P. B., and P. Blais, Perfluorocarbon blood substitutes, in CRC Critical Reviews in Oncology/Hematology, Vol. 6, No. 4, pp. 311–374, 1987, which is hereby incorporated by reference.

To date, about 300 liquid compounds have been investigated for blood-gas exchange applications [4]. Those liquids which have evolved as artificial blood substitutes are complex perfluorocarbon liquid-based aqueous emulsions containing various chemical stabilizers and viscosity modifiers, along with conventional parenteral additives (glucose, electrolytes, starch, and buffers). Compatibility with blood and a surprising lack of major adverse effects have been demonstrated in several animal species. The first administration of perfluorocarbon liquid blood substitute (Fluosol-DA, one of four commercial blood substitutes now available) to human volunteers occurred in 1978 [10], with the first clinical use taking place shortly after in 1979 [11,12]. Subsequently, numerous other studies have been carried out in Japan, the United States, Canada, and Europe that have confirmed the comparatively benign impact of infusing significant amounts (some tests used liters) of the perfluorocarbon/water emulsions directly into the systemic blood circulation [13,14,15]. The blood substitutes are not yet ready for general clinical systemic use for two reasons: a) the requirement to form an emulsion to suspend the perfluorocarbon particles significantly reduces the volume fraction of the gas carrier (the perfluorocarbon), thus large volumes must be infused, and b) the emulsion gradually coalesces as it circulates, leading to premature removal of many of the synthetic constituents from the blood. However, studies are currently ongoing in a number of clinically related therapeutic perfluorocarbon applications primarily taking advantage of the oxygen carrying capacity of blood substitute emulsions [16,17,18,19].

It was first demonstrated that mammals submerged in hyperoxygenated saline could breathe liquid and successfully resume gas breathing in 1962 [20]. However, this approach to liquid ventilation (LV) was eventually abandoned, due to the practical difficulties of dissolving sufficient quantities of $O_2$ in saline (done under high pressure), and because saline rinses away much of the surfactant lining the lung alveoli [21]. These problems were overcome in 1966, by Dr. Leland Clark [22], who was the first to use perfluorocarbon liquids (now oxygenated at atmospheric pressure) to support the respiration of mice, cats, and puppies. The extreme biocompatability and suitable properties of certain perfluorocarbon liquids has subsequently led to a significant body of ongoing research yielding promising clinical applications.

To date it has been clearly established that mammals can breathe (total ventilation support) oxygenated perfluorocarbon liquids for long periods (>3 hours) and return to gas breathing without untoward long-term effects [23, 24]. In addition, studies have also shown that no adverse morphological, biochemical, or histological effects are seen after perfluorocarbon ventilation [24, 25, 26].

Perfluorocarbon liquids have also been investigated for lung lavage (washing) [27], and have been found to be effective for rinsing out congestive materials associated with Respiratory Distress syndrome (RDS) in adult humans [28]. While total respiratory support of both lungs via perfluorocarbon liquids is not without side effects, they are minor and transient (mild acidosis, lower blood $pO_2$, and increased pulmonary vascular resistance and decreased lung compliance) [3,29,30,31]. Other biomedical applications of perfluorocarbon liquid ventilation have also received serious research effort [32,33].

Pertinent to convective lung hyperthermia, i.e., lung heating by the repetitious infusion and removal of hot liquids to and from the lung, studies of the physiological heat exchange occurring from high- and low-temperature perfluorocarbon ventilation of animals have also been performed [30,41,42]. These studies have involved complete-lung liquid heating and cooling, and have been done at only moderate temperatures, but have illuminated and quantified many relevant physiological responses and systemic temperature effects. A very recent study [43] reporting hyperthermic (to 45° C.) convection heating of lungs involved sustained heating of surgically isolated dog lung lobes via heated blood perfusion, i.e., heating induced from the blood side rather than the airway side. Taking measurements of lung edema, compliance, perfusion pressure, and serotonin uptake during 2-hour sustained hyperthermia (done at 37.6°, 40.7°, and 44.5° C., time-averaged lung temperatures), no significant changes in lung parameters were found other than expected increases in perfusion pressure with temperature. The authors conclude that a normal lung appears to tolerate well the sustained heating regimens appropriate for cancer hyperthermia applications.

However, the problem of how to effect controlled and sufficiently localized hyperthermia of malignant lung tissue has, until now, remained unsolved.

As stated earlier, one way of treating pulmonary-related diseases, conditions and/or abnormalities is by the implementation of chemotherapeutic agents, either alone or in conjunction with other therapeutic techniques (e.g., radiotherapy). However, there are many problems existing when employing conventional techniques of chemotherapy. For example, in the presence of lung disease and intrapulmonary shunting, systemically administered drugs are ineffectually delivered to the diseased portion of the lung.

One conventional method of introducing such agents into a patient's pulmonary system consists of interrupting ventilatory support and exposing the delicate lung tissues of the pulmonary system to higher, and potentially traumatizing, pressures needed for manually delivering the agents. When practicing many of the conventional chemotherapeutic techniques, the final distribution of the agents, throughout the patient's pulmonary system, is generally non-uniform and typically "patchy".

Another problem associated with the presently-practiced methods of chemotherapeutic treatment of pulmonary-related diseases, conditions and/or abnormalities is often encountered during intensive care life support procedures. During such procedures, conventional gas ventilation is employed to maintain lung stability and to prevent lung collapse. However, the deleterious consequences of such life support procedures often precludes successful weaning from the particular life support system back to pulmonary gas exchange. As such, the practice of chemotherapeutic treatment, in conjunction with such conventional life support systems and/or procedures, is severely hampered.

As exemplified above, there are significant problems which exist with conventional chemotherapeutic techniques of treating pulmonary-related diseases, conditions and/or abnormalities. Until this invention, these problems were unsolved.

SUMMARY OF THE INVENTION

The invention provides, in one embodiment, a hyperthermic treatment of lung cancer, which includes the steps of: temporarily filling with a liquid medium pre-selected pulmonary air passages adjoining pulmonary tissues containing malignant cells, circulating exogenously heated liquid medium having a temperature in the range of from about 41° to about 50° C. (preferably from about 42° to about 45° C.) through the liquid-filled pulmonary air passages for a pre-determined period of time, and thereafter removing the liquid medium from the pulmonary air passages of the patient. The liquid medium may be a perfluorocarbon liquid or physiological saline solution. Suitable perfluorocarbon liquid having the requisite physical and thermal properties are characterized by an average molecular weight in the range of from about 350 to about 560 and by having: a viscosity less than about 5 CP at 25° C., a density less than about 2.0 g/cm$^3$ at 25° C., a boiling point greater than about 55° C., a vapor pressure in the range of from about 20 Torr to about 200 Torr, and a Prandtl number less than about 10 at 25° C. Representatives of such perfluorocarbon liquids are FC-84, FC-72, RM-82, FC-75, RM-101, and perfluorodecalin. The preferred group of perfluorocarbon liquids is characterized by having an average molecular weight in the range of from about 420 to about 460, a vapor pressure less than about 100 Torr at 25° C., and a surface tension less than about 17 dynes/cm at 25° C.

The invention provides in another embodiment a hyperthermic treatment of lung cancer using ultrasound, including the steps of: temporarily filling with a liquid medium preselected pulmonary air passages adjoining pulmonary tissues comprising malignant cells, heating the adjoining pulmonary tissues comprising the malignant cells to a temperature in the range of from about 41° to about 50° C. (preferably from about 42° to about 45° C.) for a predetermined period of time by transmitting ultrasound through the liquid-filled pulmonary air passages, and thereafter removing the liquid medium from the pulmonary air passages of the patient. Perfluorocarbon liquids having the requisite physical, thermal, and acoustic properties for this ultrasound treatment are characterized by an average molecular weight in the range of from about 400 to about 560. Such perfluorocarbon liquids are also characterized by having: viscosity less than about 5 CP at 25° C., density less than about 2.0 g/cm$^3$ at 25° C., boiling point greater than about 75° C., vapor pressure in the range of from about 25 Torr to about 100 Torr, surface tension below about 17 dynes/cm at 25° C., acoustic impedance in the range of from about 0.8 to about 1.6 MegaRayls at 37° C., and acoustic attenuation less than about 1.2 db/cm (at 1.0 MHz, 45° C., and acoustic intensity of about 3 W/cm$^2$). The preferred group of perfluorocarbon liquids for this purpose is characterized by an average molecular weight in the range of from about 420 to about 460, and representative of these are FC-75, RM-101, and perfluorodecalin. Operable and preferred ultrasound frequency ranges are also disclosed, for use with different liquid-filled regions of the pulmonary air passages. The ultrasound may be produced by a transducer disposed within the liquid-filled pulmonary air passages, or the transducer may be disposed exogenous to the liquid-filled pulmonary air passages. For example, the ultrasound may be transmitted through an intercostal space of the patient, or it may be transmitted from an exposed surface of the lung into the volume of same during an intra-operative application involving an "acoustic window" into the lung created by surgical means.

In yet another embodiment, the invention provides liquid infusion and isolation catheters, intracavitary ultrasound applicators, and intercostal ultrasound applicators for practicing the disclosed convection and/or ultrasound hyperthermia treatments of lung cancer.

In even another embodiment, the invention provides a means for delivering biological agents directly to at least a portion of the pulmonary system via liquid-born agents which are either recirculated in and out of the pulmonary system (e.g., by liquid lavage or liquid ventilation) or maintained static (i.e., non-recirculated) for extended periods of time. Breathable liquids are capable of providing, simultaneously, ventilation during drug delivery.

In still another embodiment, the invention provides a means to directly access cardiac output for drug infusion of biological agents, when systemic collapse precludes intravascular administration of such agents.

Other objects, aspects and embodiments of the invention will become apparent to those skilled in the art upon reading the following detailed description, when considered in conjunction with the accompanying drawings and the appended claims.

BRIEF DESCRIPTION OF THE DRAWINGS

FIG. 1 depicts a representative liquid infusion and isolation catheter according to the invention;

FIG. 2 depicts a pair of representative intercostal ultrasound applicators;

FIG. 3 shows a representative intracavitary ultrasound applicator, and also an optional cuff plug;

FIG. 4 shows the construction of a representative intracavitary transducer assembly;

FIG. 5 shows another representative intracavitary ultrasound applicator;

FIG. 6 illustrates in greater detail the representative transducer assembly shown in FIG. 5;

FIG. 7 is a graph indicating the molecular weights of representative perfluorocarbon liquids;

FIG. 8 is a graph indicating the surface tension (dynes/cm) of representative perfluorocarbon liquids;

FIG. 9 is a graph indicating the viscosity at 25° C. (CP) of representative perfluorocarbon liquids;

Figure 34:
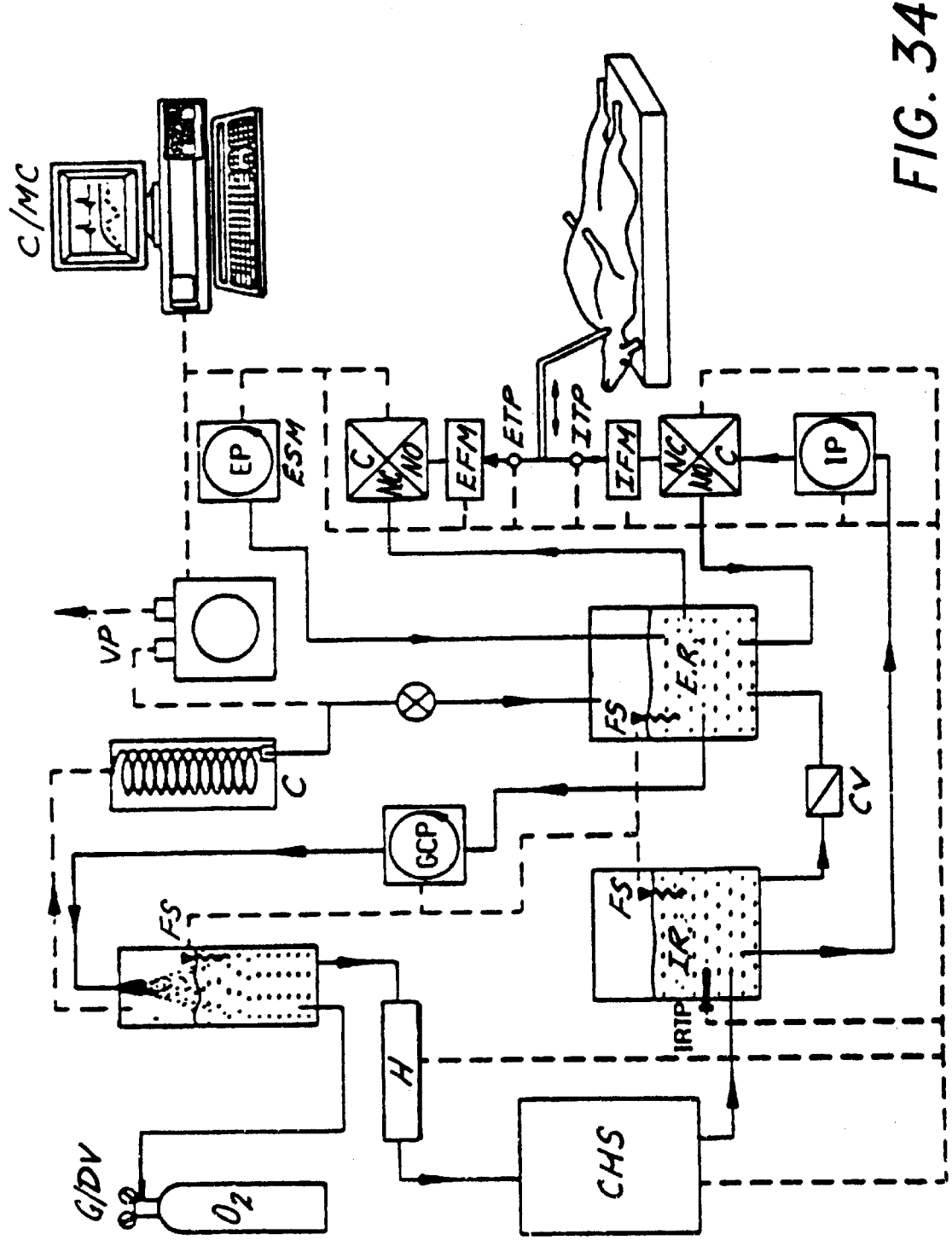
Figure 35:
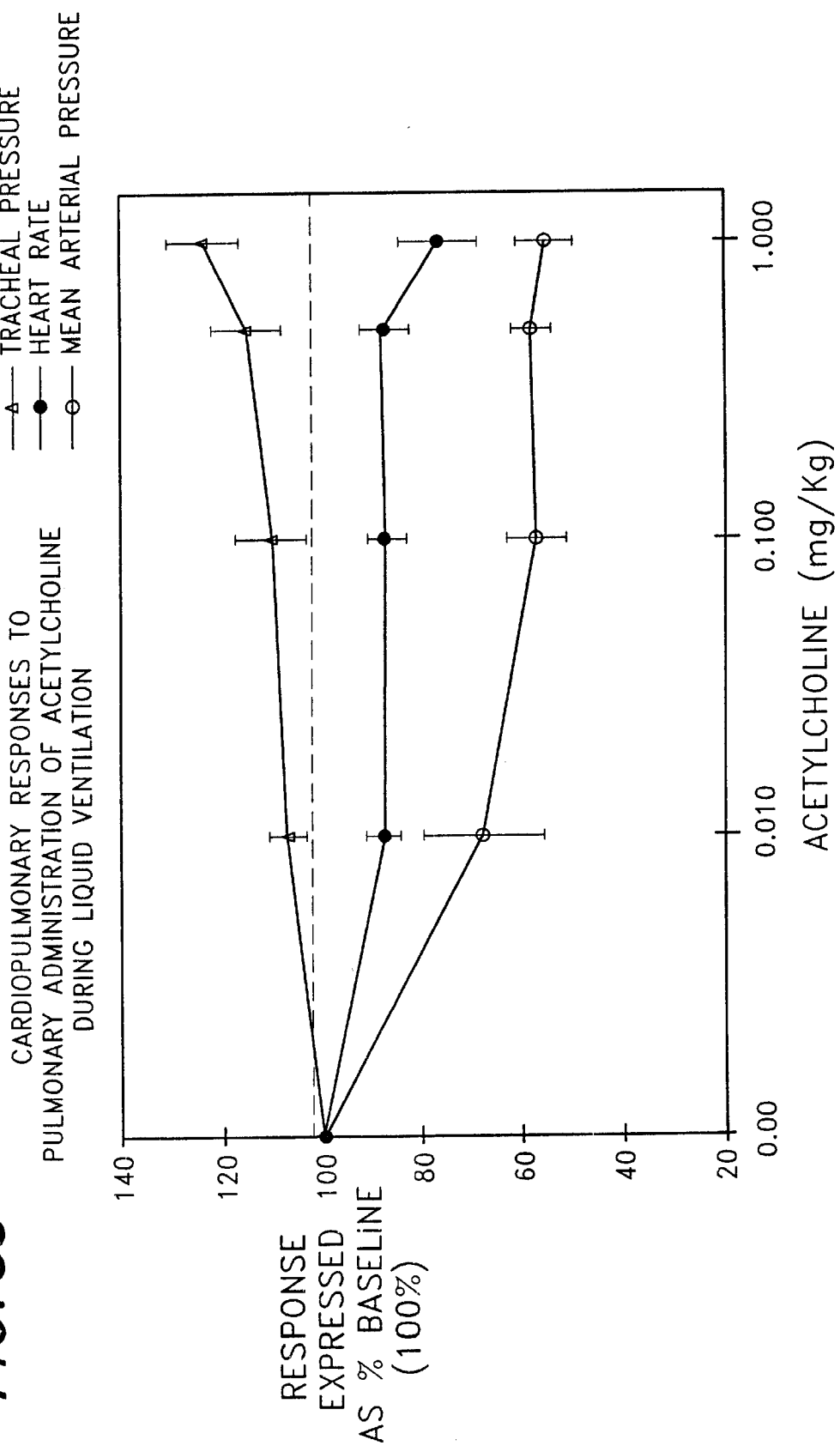
Figure 36:
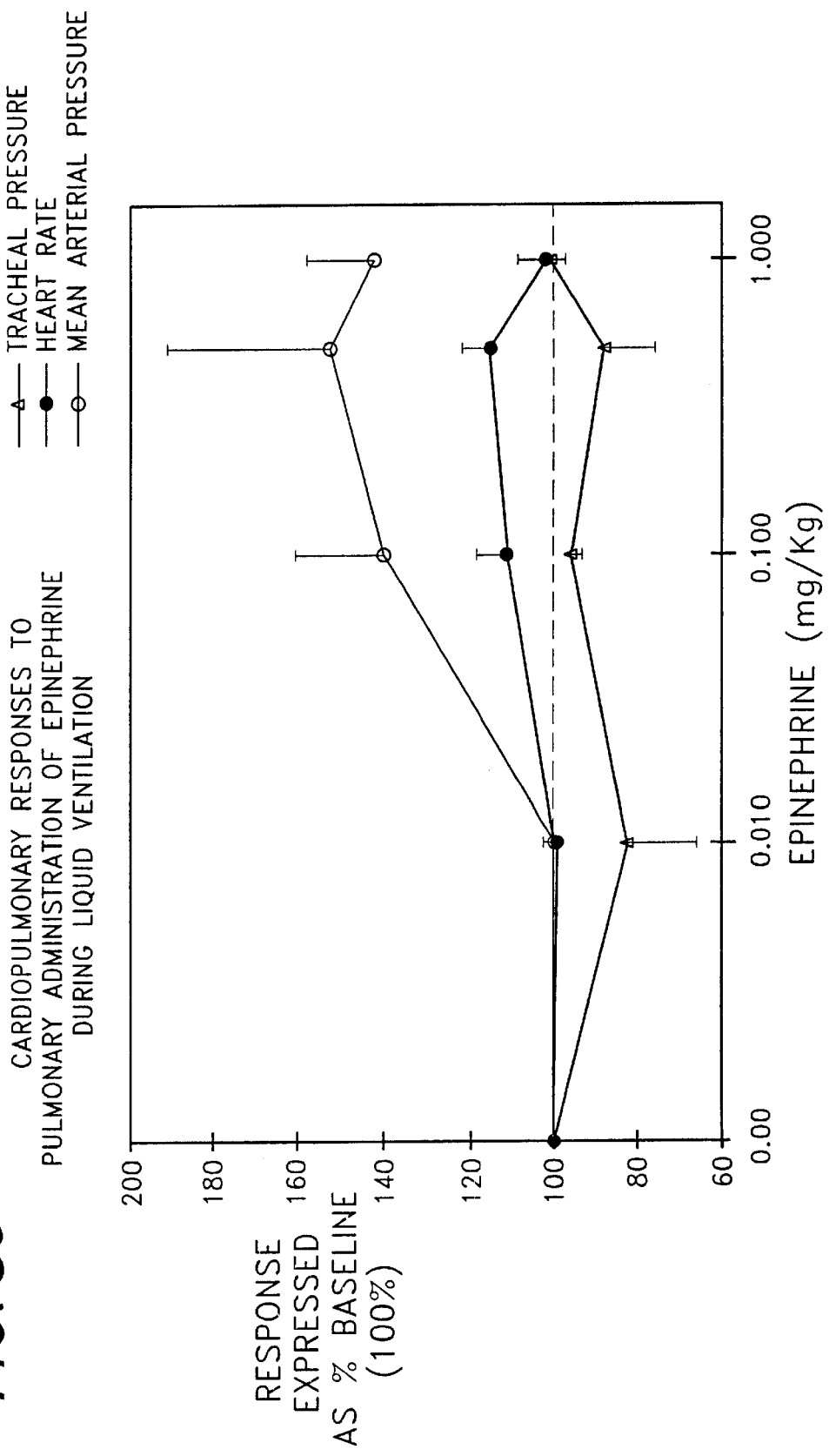
Figure 37:
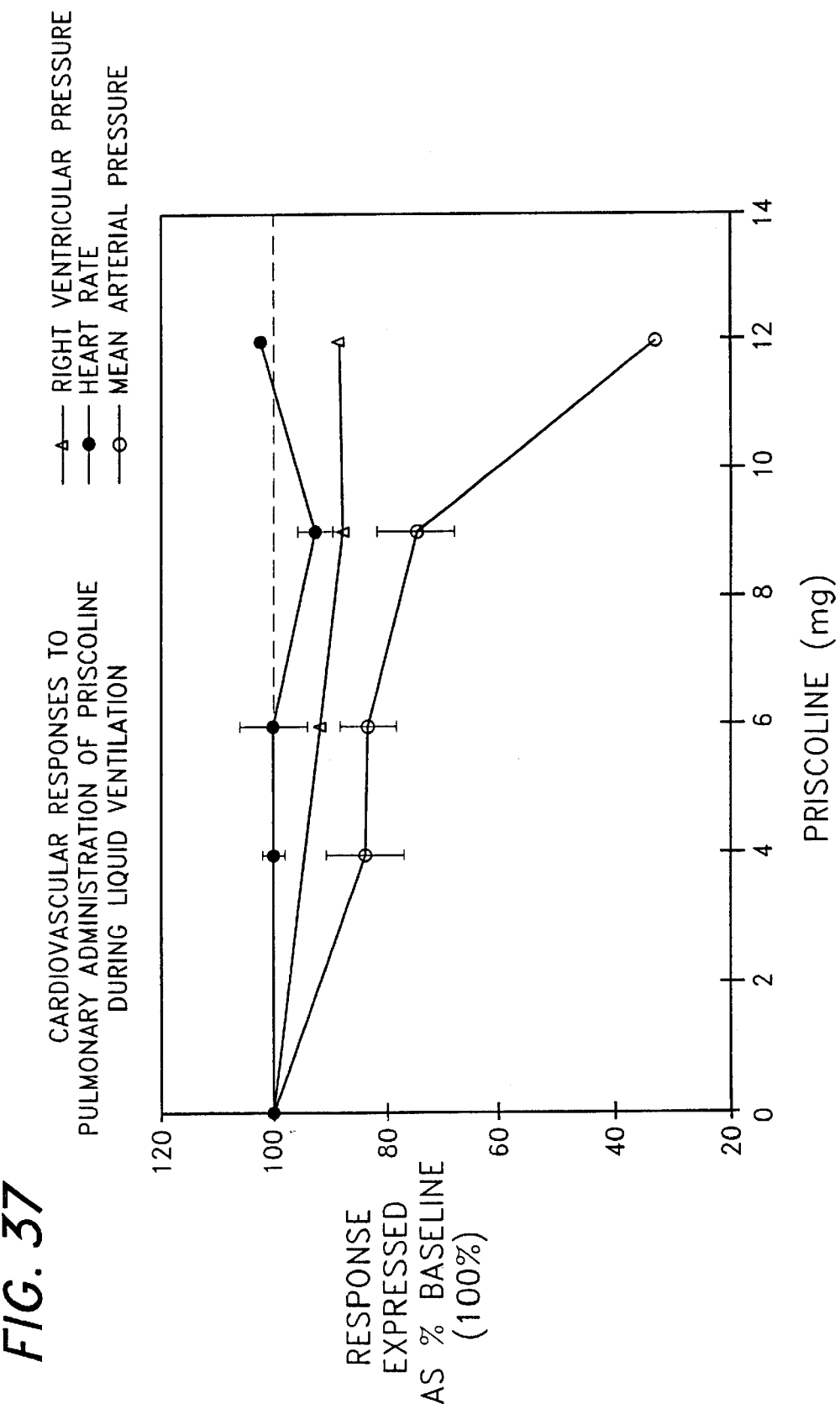
Figure 38:
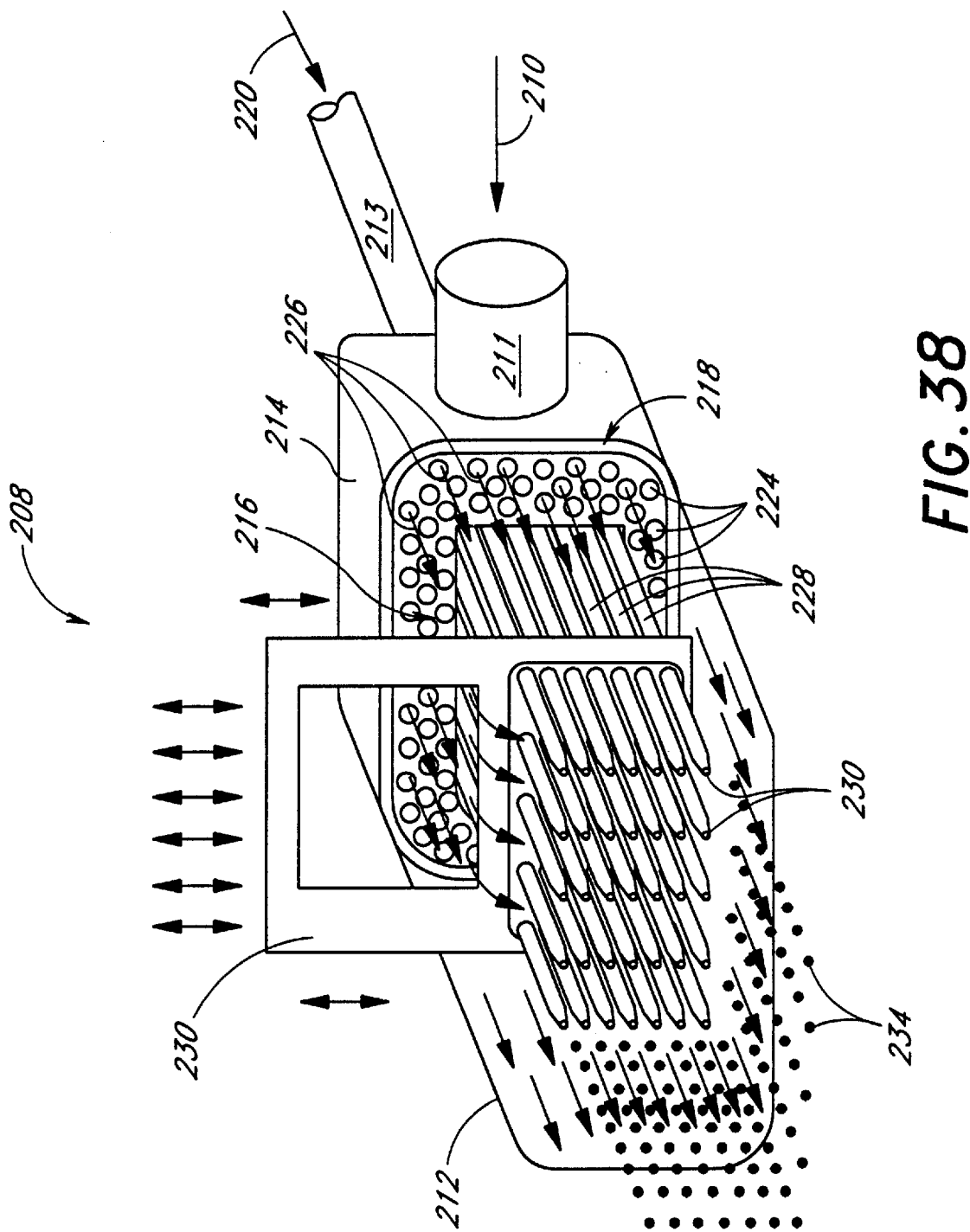

FIG. 34 is a schematic diagram of a representative liquid-filled lung convection hyperthermia and liquid infusion system, wherein the following abbreviations apply; IP, insp. pump; EP, exp. pump; ITP, insp. temp. probe; ETP, exp. temp. probe; IFM, insp. flow meter; EFM, exp. flow meter; IR, insp. reservoir; ER, exp. reservoir; CV, check valve; IRTP, insp. res. temp. probe; GCP, gas circular pump; and FS, free surface;

FIG. 35 is a graphical depiction of cardiopulmonary responses to the pulmonary administration of acetylcholine;

FIG. 36 is a graphical depiction of cardiopulmonary responses to the pulmonary administration of epinephrine;

FIG. 37 is a graphical depiction of cardiovascular responses to the pulmonary administration of priscoline; and FIG. 38 is a representative apparatus for producing a uniformly dispersed drug-containing phase within a continuous liquid delivery phase.

DETAILED DESCRIPTION OF THE PREFERRED EMBODIMENTS

The invention provides in one embodiment, a method of treating lung cancer by convection hyperthermia. Preselected pulmonary air passages that adjoin pulmonary tissues containing malignant cells are temporarily filled with a liquid medium such as physiological saline solution or, preferably, a perfluorocarbon liquid. By "pulmonary air passages" is meant the pulmonary channels, spaces or volumes in the trachea, left and right bronchi, bronchioles, and alveoli of the lungs that are normally occupied by air. In the practice of the invention, only the pulmonary air passages in contact with or near a patient's tumor site(s) are typically filled with the liquid medium, and gaseous ventilation of the remaining pulmonary air passages is maintained. Depending on the location of the lung cancer, as determined by available diagnostic methods, the fluid-filled pulmonary air passages may be localized in a lung, lobe or lung segment, and/or the bronchial tree may be selected for localized filling with the liquid medium. Localized filling of the pulmonary air passages in such a preselected manner can be effected by means of the representative infusion catheters described below. Diagnostic ultrasonic imaging can be used to monitor the filling of the pulmonary air passages, if either physiological saline or a perfluorocarbon liquid serves as the liquid medium. During the filling step, the perfluorocarbon liquid is preferably degassed at least 50%, and is most preferably substantially (almost totally) degassed.

To effect the localized convection hyperthermia treatment, exogenously heated liquid medium having a temperature in the range of from about 41° to about 50° C., and preferably from about 42° to about 45° C., is circulated through the liquid-filled pulmonary air passages for a period of time that may be determined at the discretion of the attending physician. During, prior to or subsequent to this hyperthermic treatment, the malignant cells may be irradiated with ionizing radiation such as x-rays, electron beams, neutron beams, etc. To potentiate the effects of such radiation treatments, the liquid medium in the fluid-filled pulmonary air spaces may be oxygenated. In treatments where the preselected pulmonary air passages are initially filled with substantially degassed perfluorocarbon liquid, exogenously heated oxygenated perfluorocarbon liquid may be circulated into the liquid-filled pulmonary air passages after the filling process is complete, prior to and/or during irradiation of the malignant cells with the ionizing radiation.

The circulating liquid medium may also contain a therapeutic agent such as an anti-cancer drug (e.g., adriamycin), toxin, antibody-linked radionuclide, etc. In treatments where the adjunctive use of such water-soluble therapeutic agents is desirable, the liquid medium may be an aqueous perfluorocarbon liquid emulsion.

After the hyperthermic treatment period, which as mentioned will vary in a patient-specific manner, depending partly upon the tumor location and any adjunctive therapies employed, the liquid medium is removed from the pulmonary air passages of the patient.

A preferred liquid medium for this convection hyperthermia treatment is a perfluorocarbon liquid of the general type used for lung ventilation. Suitable perfluorocarbon liquids having the requisite thermal as well as physical properties for use in convection pulmonary hyperthermia include perfluorocarbon liquids characterized by an average molecular weight, of the perfluorocarbon constituent(s), in the range of from about 350 to about 560. Such perfluorocarbon liquids are alternatively characterized by having a viscosity less than about 5 CP at 25° C., a density less than about 2.0 g/cm$^3$ at 25° C., a boiling point greater than about 55° C., a vapor pressure greater than about 20 Torr but less than about 200 Torr at 25° C., a surface tension less than about 17 dyne/cm at 25° C., and a Prandtl number less than about 10 at 25° C. To provide some adjunctive respiratory support, and for use with radiation therapy, and to provide efficient lung filling in the degassed state, the perfluorocarbon liquid should also have an oxygen solubility greater than about 40 ml/100 ml. Representative perfluorocarbon liquids that meet the above criteria include FC-84, FC-72, RM-82, FC-75 (3M Company, Minneapolis, Minn.), RM-101 (MDI Corporation, Bridgeport, Conn.), dimethyladamantane (Sun Tech, Inc.), trimethylbicyclononane (Sun Tech, Inc.), and perfluorodecalin (Green Cross Corp., Japan). The preferred group of perfluorocarbon liquids, in terms of optimizing the operative combination of physical and thermal properties, are characterized by an average molecular weight in the range of from about 400 to about 460. Such perfluorocarbon liquids are characterized by having a vapor pressure less than about 100 Torr. The most preferred perfluorocarbon liquids have an average molecular weight in the range from about 420 to about 460, and representative of this group are FC-75, RM-101, and perfluorodecalin.

The invention also provides an ultrasonic hyperthermic treatment of lung cancer. In this embodiment, after the preselected pulmonary air passages adjoining the patient's malignant cells are filled with the liquid medium such that an adequate and appropriate acoustic transmission path has been established, the pulmonary tissues containing the malignant cells are heated to a temperature in the range of from about 41° to about 50° C. by transmitting ultrasound through the liquid-filled pulmonary air passages. In a preferred embodiment, the ultrasound is produced by an intracavitary transducer that is positioned within the liquid-filled pulmonary air passages. Alternatively, the transducer may be located exogenous to the pulmonary air passages. For example, the ultrasound can be transmitted through an intercostal space between the ribs of the patient, or the transducer can be applied to the pulmonary pleura or lung surface overlying the fluid-filled passages, following surgical displacement of ribs or other interfering tissues.

In order to server as a suitable acoustical propagating medium in this ultrasonic hyperthermic treatment, the perfluorocarbon liquid should have the following physical, thermal, and acoustical properties: viscosity less than about 5 CP at 25° C., density less than about 2.0 g/cm$^3$ at 25° C., boiling point greater than about 75° C., vapor pressure greater than about 25 Torr and less than about 100 Torr, acoustic impedance between about 0.8 to about 1.6 Mega-Rayls at 37° C., and acoustic attenuation less than about 1.2 dB/cm (±20%) at 1.0 MHz, 45° C., and acoustic intensity of about 3 W/cm$^2$. The perfluorocarbon liquid is preferably also characterized by an oxygen solubility greater than about 40 ml/100 ml. Perfluorocarbon liquids having an average molecular weight in the range of from about 400 to about 500 generally satisfy the above criteria, with the preferred group in terms of optimizing the thermal and acoustical properties having an average molecular weight in the range of from about 400 to about 460, and most preferably in the range of about 420 to about 460. Representative of this most preferred group of perfluorocarbon liquids are FC-75, RM-101, and perfluorodecalin.

In treatments where the preselected liquid-filled pulmonary air spaces are localized in the bronchial tree, the ultrasound from an intracavitary transducer preferably has a frequency in the range of from about 250 KHz to about 3 MHz, and most preferably from about 500 KHz to about 2 MHz. For peripheral lung treatments (i.e., in the membranous airways and alveoli of the lung), where the sound waves must necessarily traverse many more liquid-tissue interfaces, a lower ultrasound frequency in the range of from about 250 KHz to about 1.5 MHz is necessary when perfluorocarbon liquids serve as the liquid medium. Ultrasound frequencies in the latter range are also recommended when the transducer is positioned exogenous to the lung.

The desired frequency within these ranges is established on the basis of the depth of heating sought. Lower frequencies are attenuated less and, therefore, are employed where deeper heating is preferred. Conversely, higher frequencies are more readily absorbed, and thus are more appropriate for more superficial heating. Optimal treatments may include a combination of the following strategies. First, a single transducer may broadcast at more than one frequency to effect a desired heating pattern. The changes in frequency in this case may be done by rapid incremental changes in frequency over a specified bandwidth using frequency modulation (FM) methods, or they may be done with serial changes over time whereby sound (in FM mode or not) is generated in predetermined frequency ranges for desired periods and then changed to other frequencies for periods of time. Second, multiple transducers (focused, diverging, or unfocused) may be employed to operate in tandem at similar or different frequencies (in FM mode or not) to effect desired heating patterns.

Where physiological saline serves as the liquid propagating medium, the ultrasound can be in the frequency range of from about 250 KHz to about 3 MHz from intracavitary transducers, and in the range of from about 500 KHz (preferably about 750 KHz) to about 3 MHz from exogenous transducers.

While the perfluorocarbon liquid is preferably degassed during the filling step, oxygenation of the liquid may be desirable (e.g., for radiation treatment or respiratory support) during the ultrasonic hyperthermic treatment. However, in order to suppress cavitation, the dissolved gas content (including oxygen, air, nitrogen, carbon dioxide or other gases) of the perfluorocarbon liquid in the liquid-filled pulmonary air passages should be held at no more than about 75% of saturation for ultrasonic treatments in the 2–3 MHz range. No more than about 50% of saturation should be permitted for ultrasonic treatments in the 250 KHz to 1.5 MHz range. The requisite dissolved gas content can be maintained by circulating the perfluorocarbon liquid into and out of the lung during the treatment between the liquid-filled pulmonary air passages and an extraneous source of gas-content processing, such as a degassing chamber.

The invention also provides liquid infusion catheters, intracavitary ultrasound applicators, and exogenous ultrasound transducers, representative embodiments of which are shown in FIGS. 1–5. Prior bifurcated bronchial catheters that have been used for delivering liquid into a lung are not suitable for use in the subject convection and ultrasonic hyperthermia treatments, for a number of reasons. First, the subject treatments can be applied deeper in the lung than heretofore possible, and prior commercial devices lack sufficient flexibility and length to reach many of the segmented bronchi. In addition, the inflatable cuff material used in the prior devices tends to lose its structural integrity at the relatively high fluid temperatures involved in the subject treatments. Furthermore, the prior devices are in general too large in diameter to penetrate several of the pertinent segmental bronchial passageways in the lungs, and they also provide no instrumentation for monitoring local transient and steady state temperature, and pressure, and are ill-suited for positional information.

Figure 1:
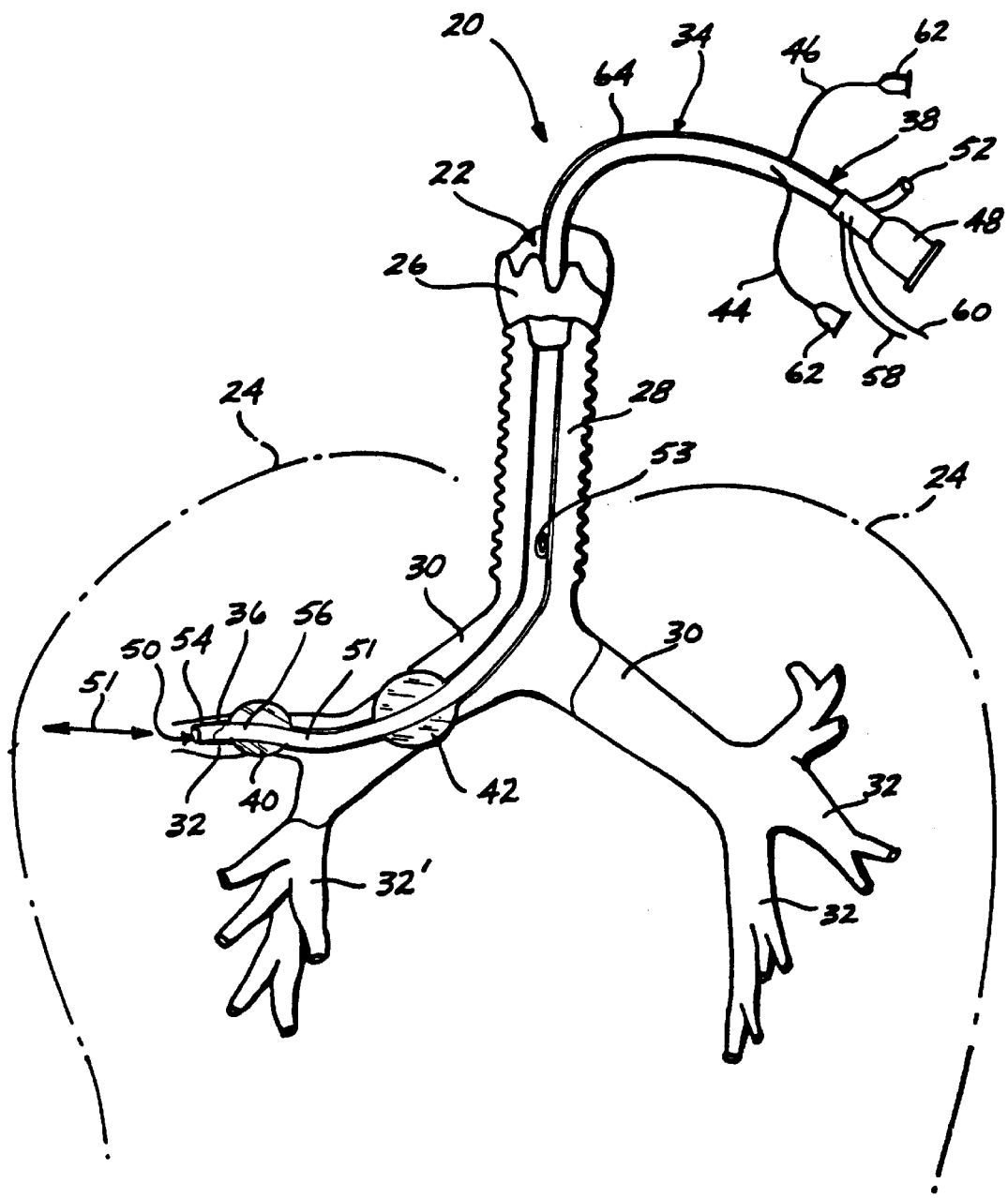

Referring initially to FIG. 1, a representative embodiment of the subject liquid infusion and isolation catheter 20 is shown in conjunction with the pulmonary air passages 22 that lead to and ramify throughout the lungs 24. More particularly, catheter 20 is shown passing through the larynx 26 and trachea 28 and into a bronchus 30 and associated segmental bronchi 32.

Catheter 20 includes a flexible conduit 34 having a distal end 36 that is positioned, in this instance, within segmented bronchus 32, and a proximal end 38 that is positioned outside (or exogenous to) the patient. The representative embodiment shown in FIG. 1 has a pair of inflatable cuffs 40 and 42 formed near the distal end 36 that are in fluid (liquid or gaseous) communication with corresponding channels 44 and 46 that exit the conduit 34 near the proximal end 38. Also shown at the proximal end 38, a liquid inlet/outlet connector 48 is in fluid communication through a liquid passageway 51 with an opening 50 at the distal end 36 of conduit 34. A gas ventilation channel 52 also is formed in the conduit 34 to be in fluid communication with a ventilation port 53 positioned so as to ventilate the bronchial tree. A pressure sensor 54 and temperature sensor 56 are positioned near the distal end 36, and have lead wires 58 and 60, respectively, passing through the conduit 34 and exiting at the proximal end 38. The temperature sensor 56 may take the form of a thermistor, thermocouple, resistance-based temperature device, etc. Suitable pressure sensors 54 include: solid-state piezoresistive diaphragm-based sensors, semiconductor strain gage sensors, etc.

The conduit 34 is typically formed from flexible plastics, such as a Teflon™, silicon rubber, polyurethanes, polyvinylchloride, Delrin™, or acetyl copolymers, or combinations thereof, having an outer thermal insulation layer 64 formed, for example, of a closed-cell plastic or rubber, to reduce heat loss to the tissues in contact with it, between the connector 48 and outlet 50 or at least the most proximal cuff 42. Alternatively, effective thermal insulation can be achieved by proper selection of the catheter material itself and its channel wall thicknesses. To minimize diameter and maximize flexibility, the conduit 34 is typically extruded to have the gas ventilation channel 52, the fluid channels 44 and 46, and the liquid passageway 51 integrally formed therein. The above elements may alternatively be separately formed and bound in a common sheath (not shown), although this may disadvantageously affect the diameter and flexibility of the conduit 20.

The cuffs 40 and 42 are preferably constructed of polyurethane or other distensible material that will maintain structural integrity when stretched and yet not lose elasticity when subjected to high temperature liquids. The cuffs 40 and 42 are concentrically formed about the conduit 34 to be selectively inflated and deflated via liquids such as physiological saline or perfluorocarbon liquids, or gas such as air, through the channels 44 and 46. A suitable connector 62, such as a Leur lock fitting, is located at the terminal end of each channel 44 and 46 to provide attachment to a source of liquid or gas such as a lockable syringe or a hand or mechanical pump. In the circumstance whereby liquid is the preferred cuff inflation fluid, it is likely that some liquid will have been placed in the cuff prior to use, to insure a gas-free volume inside the cuff. When inflated, the cuffs 40 and 42 bear against the encircling inner walls of the trachea 28, bronchus 30, and/or lobar or segmented bronchus 32 (depending upon the positioned location of catheter 20 in the pulmonary air passages 22), in order to locally seal the lumen (3) of the airway(s) to prevent the passage of liquid and gas during the hyperthermic treatment. Although a pair of cuffs 40 and 42 are shown, one or both may be eliminated, e.g., if both lungs are to be filled with the fluid. Additional cuffs may also be used to provide the requisite sealing. The number of cuffs used will depend on where the hyperthermic treatment is being directed in the lung, the passageways to be isolated and those to be kept gas ventilated, and the length of the catheter 20. In this regard, the cuffs 40 and 42, when required, are sized according to their application, i.e., whether they will be positioned in a large lobar bronchus (0.83 cm average diameter) or in a smaller segmental bronchus (0.56 cm average diameter). Cuffs sized to dam the main bronchi (1.22 cm average diameter) and trachea (1.8 cm average diameter) can also be readily fabricated. The use of two cuffs 40 and 42 in FIG. 1 is for illustration purposes only and is not meant to imply that the untreated distal pulmonary segments 32 are to be unventilated by gas. In use, the catheter configuration(s) will be selected to reflect the requirement to gas ventilate untreated, air-filled portions of the lung.

The gas ventilation channel 52 is used to provide respiratory gas exchange to the portions of the lungs 24 not sealed off by the cuffs 40 and 42 or filled with the liquid. The channel 52 is preferably coupled to an appropriate machine, such as a mechanical ventilator, to supply gas through the port 53 formed in the wall of the conduit 34. In the absence of such a connection air ventilation may occur by the gas being drawn into channel 52 from room air by the natural respiratory motion of the lung.

The liquid connector 48 is attached to a liquid infusion system, such as described below. Briefly, such a system provides liquid for the desired treatment at a controlled but variable tidal volume and frequency, and at a controlled temperature and gas content. The pressure sensor 54 and the temperature sensor 56 positioned at the delivery end 36 permit monitoring of the temperature and pressure of the liquid within the liquid filled air passages. Additional sensors may be positioned at any point along the conduit 34 to permit comparative measurements and to permit flow rate information in the catheter to be obtained from dynamic measurements.

In use, the catheter 20 may be fitted with a rod (not shown) formed of bendable material, such as aluminum, that is bent, prior to insertion in most cases, to a configuration designed to guide the catheter 20 through the trachea 28 to the desired location in the pulmonary air passageways 20. A fiber-optic assembly may be used either alone or in conjunction with the rod to provide visual confirmation of the positioning of the catheter 10. Such a fiber-optic assembly, including an optical fiber having a lens, may be integrated into or associated with the catheter 20, and coupled to a light source and an eyepiece to permit observation via video camera, still photographs, or the eye. A fiber-optic bronchoscope may be alternatively inserted through liquid passageway 51 for the same purpose. To assist in measuring distances to various parts of the lung, the outer surface of catheter 20 may be provided with distance indicator marks in spaced array.

Once the catheter 20 is in position, the various connectors at the proximal end are connected to the appropriate machines and monitoring devices. For instance, the liquid inlet/outlet connector 48 is attached to a liquid infusion system, and the fluid line connectors 62 are attached to suitable sources of liquid or gas. The cuffs 40 and 42 are inflated as necessary to seal off the pulmonary air passages adjoining the cancer cells while maintaining gas communication to untreated lung volume. The gas ventilation channel 52 is hooked to a mechanical ventilator and a suitable gas mixture is supplied through the port 53 to the unaffected air passageways. With temperature and pressure being monitored, liquid from the infusion system is supplied through the liquid passageway 51 to the, in this instance, bronchiole 32 at a controlled frequency and tidal volume (indicated by arrow 51). Following the hyperthermic treatment, the liquid can be removed from the pulmonary passages 20 by suction, by gravity (i.e., placing the patient tilted with the head down in the so-called "Trendelenburg" posture), and by evaporation.

Figure 2:
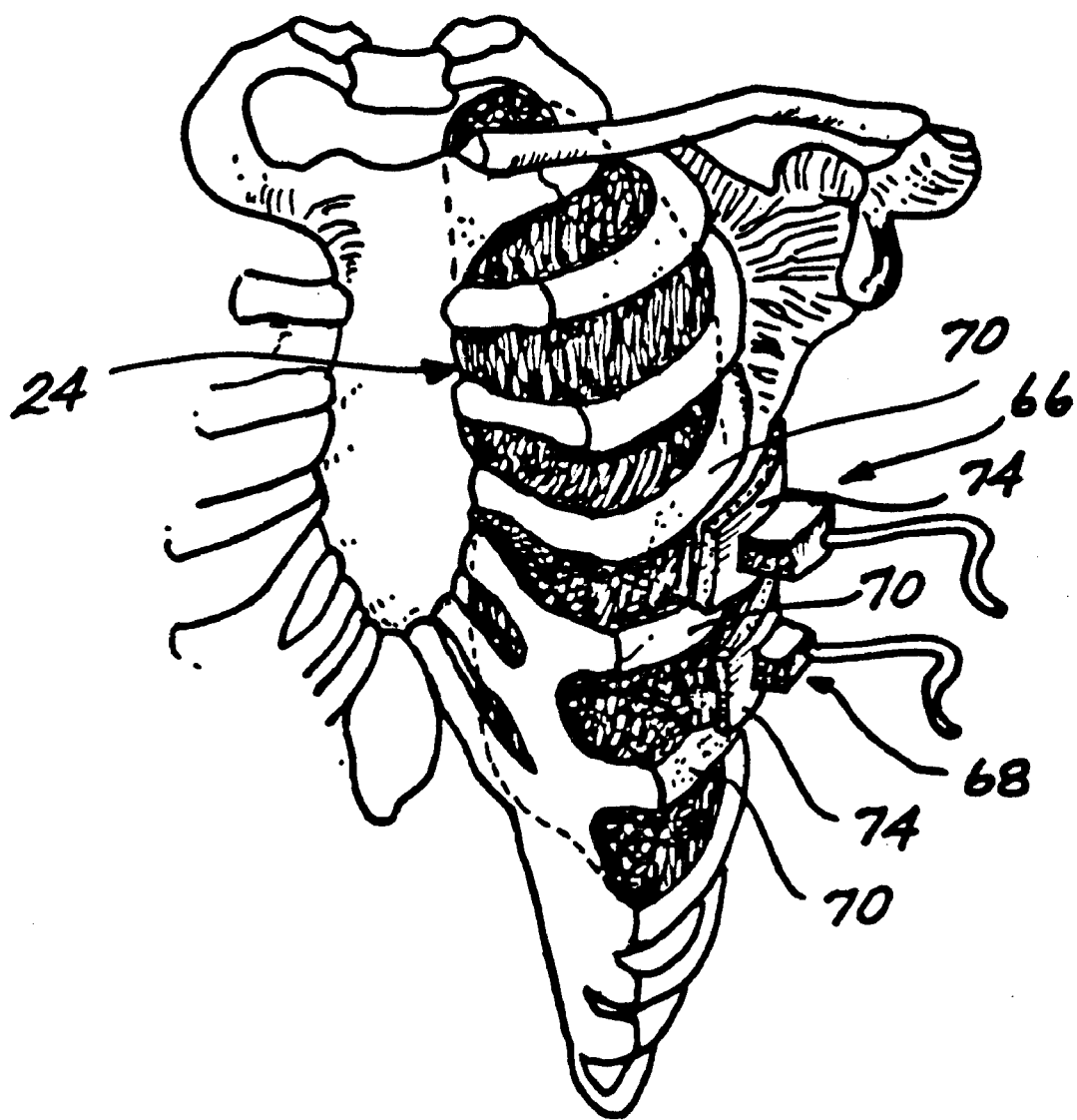

The liquid infusion and isolation catheter 20 may also be used in conjunction with external intercostal ultrasound applicators to provide the means for liquid filling and to provide additional heating and/or cooling to the tumor site. For instance, as shown in FIG. 2, a pair of intercostal applicators 66 and 68 are placed externally on the patient to direct sound waves between the ribs 70 and into the peripheral portions and bronchial spaces of the lung 24. These ultrasound power applicators 66 and 68 are composed of long aspect-ratio rectangular transducers 74, operated either singly or as a synchronous or asynchronous pairs. These applicators 66 and 68 can have flat (plane wave), broad-band unfocused transducers 74 or may have curved, focused transducers. Ideally these will be operated in the range from 250 KHz to 1 MHz.

Such applicators 66 and 68 can be used in conjunction with a liquid infusion and isolation catheter 20 to apply heat both convectively and ultrasonically to a specific portion of the lung 24. Although it would appear that a venetian blind or striped pattern of heating would result from this arrangement, it should be noted that the targeted tissue can be "scanned" up and down in front of the transducer array by a cyclic variation of the inflation pressure of the lung 24. This induced variation may be large or small, according to the motion desired. Likewise, the overall position of the tumor to be treated may be located with respect to the applicators 66 and 68 by virtue of inflation or deflation of the lung 24. Also, the respiratory motion normally present in the lung 24 may be suppressed by imposing a constant liquid infusion pressure at the desired level. Although not shown, it is to be understood that the applicators 66 and 68 may be in fixed position relative to each other, such as by mounting to a jig or frame.

Although not shown in this view, a transducer can alternatively be applied directly to the body of the lung following surgical resection of a rib or other interfering tissues. The transducer for this application will typically be supplied with a bolus of degassed coupling liquid, also serving the function of cooling the transducer and tissue surfaces.

Figure 3:
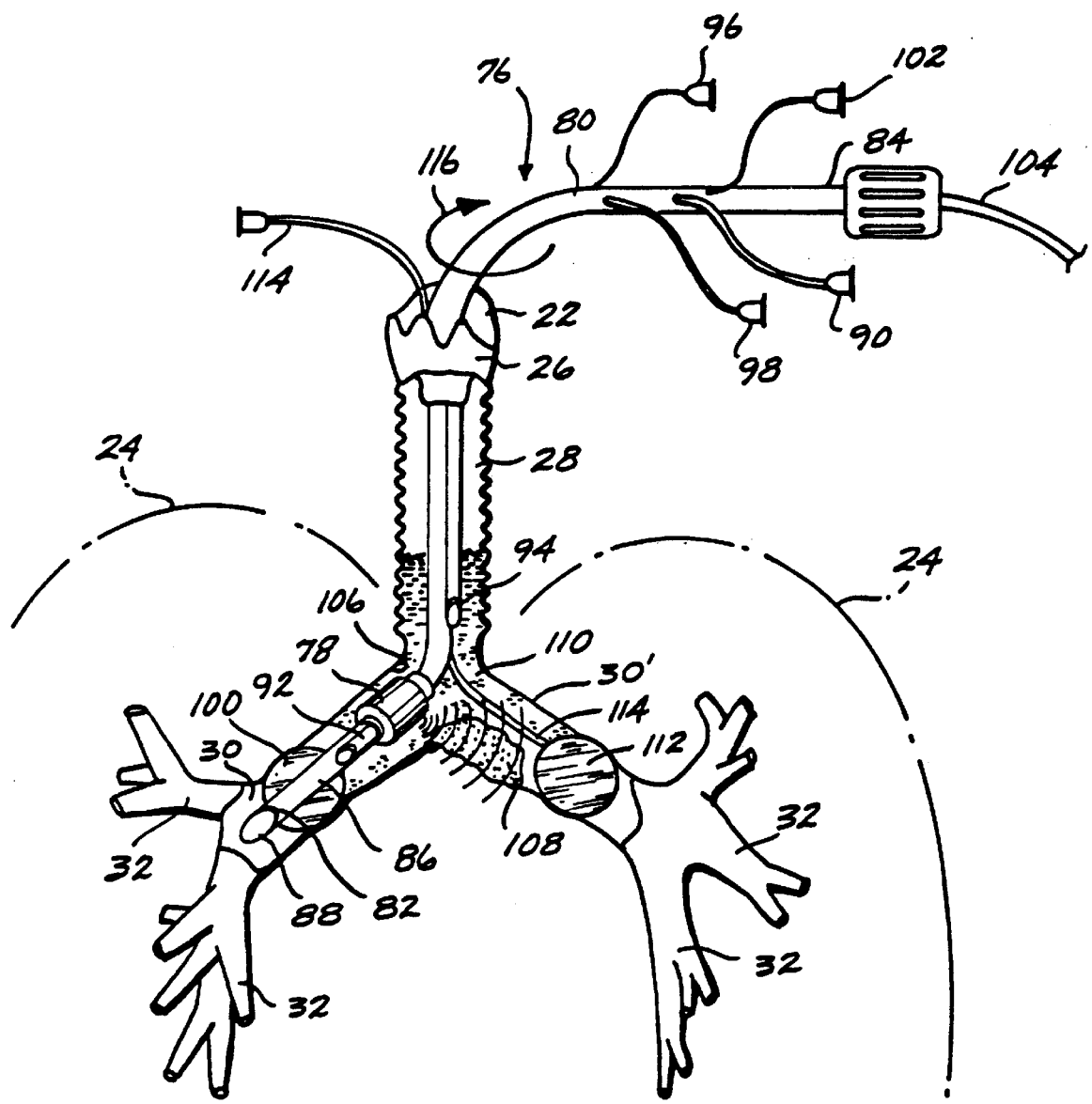

Another method of providing ultrasound hyperthermia is to place an ultrasound applicator within the fluid-filled pulmonary air passage near the tumor to be treated. FIG. 3 shows a representative embodiment of such an intracavitary applicator 76 for delivering an ultrasound transducer 78 to the treatment site. To facilitate the description, the reference numbers used in FIG. 1 are correspondingly employed in FIG. 3 (and in FIG. 4, described below). The intracavitary applicator 76 of FIG. 3 includes a conduit 80 having a distal end 82 positionable within the pulmonary air passages 22 and a proximal end 84 that remains outside the thoracic air passage 22. The conduit 80 encases a ventilation passageway 86 passing through the transducer 78 in fluid communication with the pulmonary air passages 22 through a distal opening 88. The passageway 86 terminates at the proximal end 84 of the conduit 80 with a coupling 90 for attachment to a respirator (not shown). The conduit 80 also houses a liquid inlet port 92, typically positioned distal to the transducer 78, and a liquid return port 94 positioned, in this instance, proximal to the transducer 78. The liquid inlet port 92 is in fluid communication with a liquid inlet coupler 96, and a liquid return port 94 is in fluid communication with a liquid return coupler 98, both couplers 96 and 98 being located at the proximal end 84 of the conduit 80. Formed concentrically about the ventilation passageway 86 and positioned distal to the transducer 78 and liquid ports 92 and 94 is an inflatable cuff 100. A fluid line coupling 102 is in fluid communication with the cuff 100, for connecting the cuff 100 to a suitable source of pressurized liquid or gas (e.g., air). Power cables 104 pass through the conduit 80 to provide high frequency electrical power to the transducer 78.

This conduit 80 is constructed with similar materials and by similar methods as the liquid infusion catheter 20 described above. Here, in FIG. 3, the transducer assembly 78 is positioned concentrically around the ventilation passageway 86. In this manner, the distal cuff 100, when inflated, serves to dam the proximal pulmonary passages 30'. The distal cuff 100 also anchors the distal end 82 of the conduit 80, and thereby permits the transducer 78 to be manipulated into position in the center of the bronchus 30 (or trachea 28) to avoid contact with the bronchus wall 106 and the tumor 108. The cuff 100 is otherwise substantially the same as the cuffs 40 and 42 described above with respect to FIG. 1. When the cuff 100 is inflated, it seals off the bronchus 30 so that a degassed liquid propagating medium 110 can be supplied to and fill the bronchus 30 through the liquid inlet port 92, to provide acoustic coupling and secondarily to cool the transducer assembly 78. Circulation of the liquid 110 may be accomplished by circulating liquid from the bronchus 30 through the liquid return port 94 to a liquid supply system, such as described below.

In order to prevent filling of the other lung, if that is desirable, an optional cuff plug 112, which is independent of the intracavitary transducer and its support shaft and conduit 80, is inserted within the other bronchus 30', and its degree of distension is controlled with pressurized liquid or gas supplied through a line 114. Respiration is accomplished through the one lung by supplying air through the ventilation passageway 86. Although not shown, it is to be understood that the cuff assembly 112 and 114 may, and preferably should, be supplied with a separate ventilation passageway (not shown) in order to ventilate the pulmonary air passage 32 distal to cuff plug 112. Pressure and temperature sensors (not shown) may also be disposed and used as desired, such as described above with respect to FIG. 1. Installation of the intracavitary applicator 76 can be accomplished substantially the same way as described above with respect to the liquid infusion and isolation catheter 20. Positioning of the transducer 78 with respect to the tumor 108 is accomplished by rotating the conduit 80 as shown by the rotational arrow 116.

Figure 4:
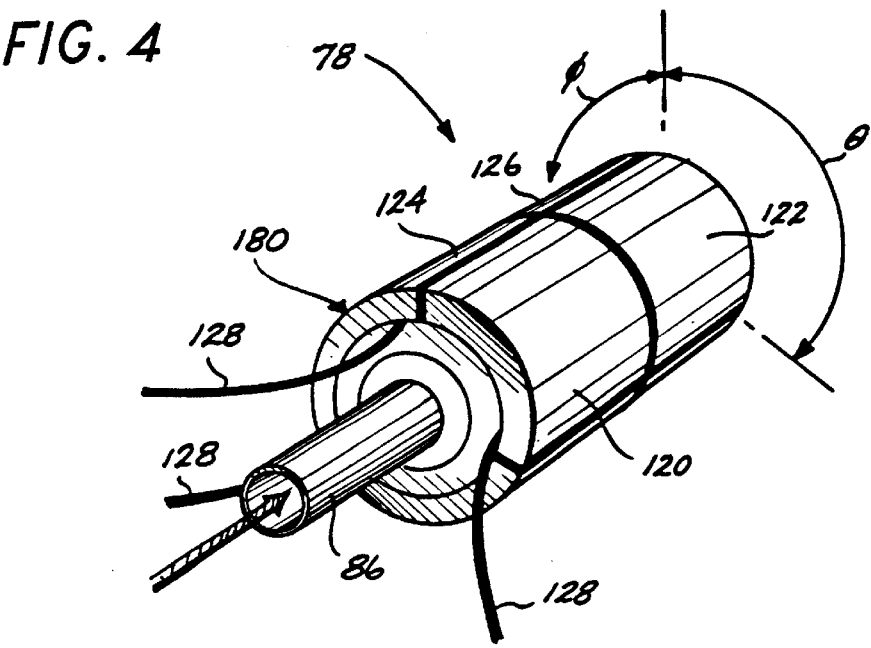

The construction of such a representative intracavitary transducer assembly 78 is shown in greater detail in FIG. 4. Here, one approach to providing selective directional heating patterns is illustrated. FIG. 4 shows a thin-walled piezoelectric ceramic cylinder 180 that is longitudinally and circumferentially sectioned into four separate power transducers, with transducers 120 and 122 formed to have an arcuate cross-sectional shape of approximately 120°, as indicated by angle θ; and with transducers 124 and 126 formed to have an arcuate cross-sectional shape with an included angle of approximately 240°, as represented by angle φ. Leads 128 supply power to the transducers, and the ventilation passageway 86 is shown, in this instance, passing coaxially through the cylinder 180. This multiple-transducer approach provides flexible heating patterns. For instance, with transducers 120 and 122 driven in parallel, a 120° pattern can be achieved. Similarly, with transducers 124 and 126 driven in parallel, a 240° heating pattern can be achieved. Finally, with all of the transducers being driven together, a full 360° of heating can be achieved along the length of the cylinder 180. Of course, full 360° heating patterns may also be achieved by cylindrical piezoelectric cylinders that are not sectioned.

Although the transducer assembly 78 is shown mounted coaxial with the conduit 80, it is to be understood that other positions and transducer configurations can be used. For instance, transducers formed of flat plates may be associated with or placed adjacent to the conduit 80 to radiate sound waves in one or more directions. Likewise, the transducers 124 and 126 may be eliminated to leave only the transducers 120 and 122 mounted adjacent the conduit 80.

Figure 5:
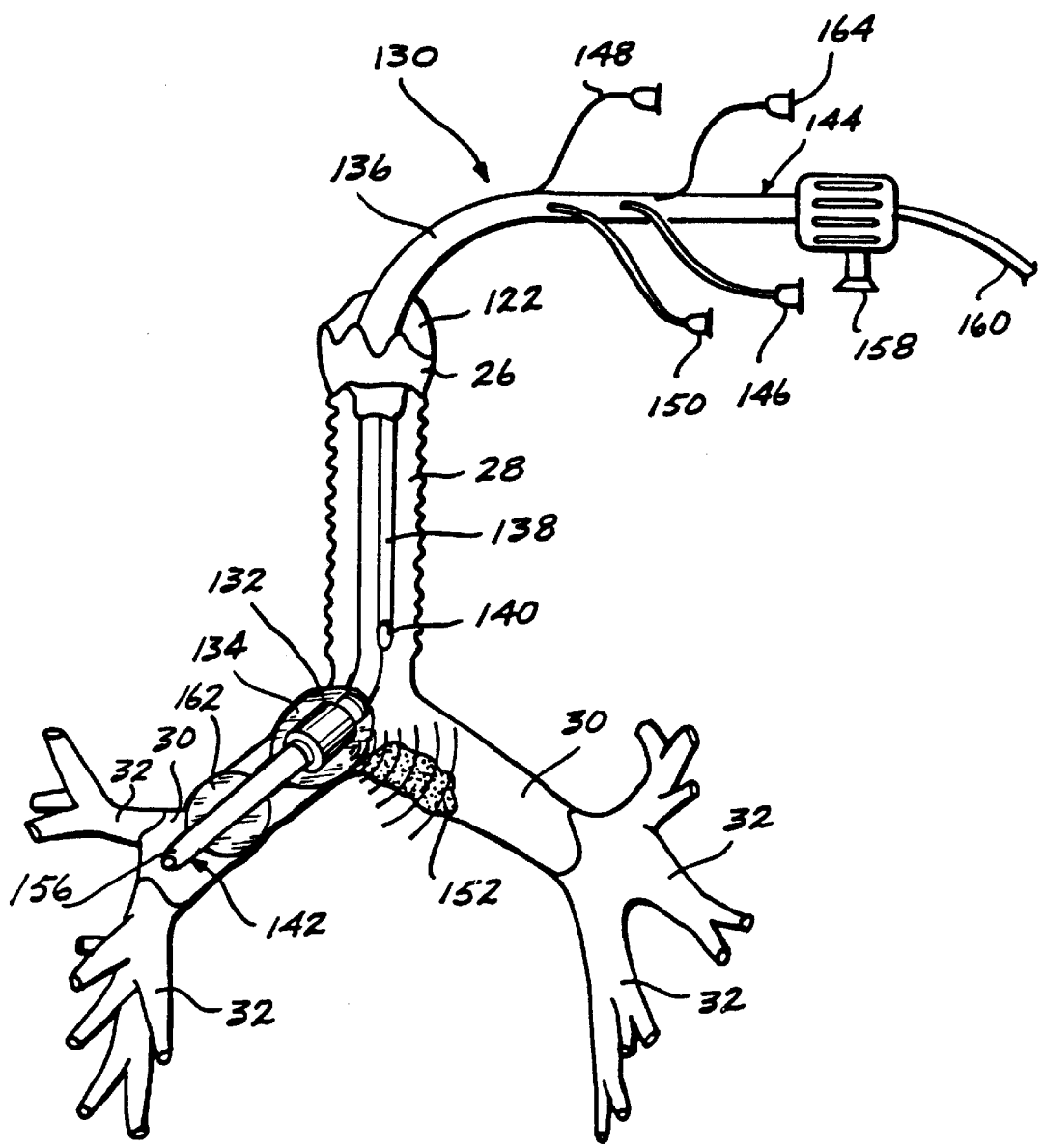

FIG. 5 illustrates yet another representative embodiment of an intracavitary ultrasound applicator 130, in which a transducer assembly 132 positioned within a self-contained liquid-filled sac 134 for acoustic coupling and cooling. This applicator 130 includes a conduit 136 having a distal end 142 positioned within the bronchus 30 and a proximal end 144 positioned outside of the patient's body. A ventilation passageway 138 is formed within or associated with the conduit 130 having a ventilation port 140 formed approximately midway down the conduit 136 and an air line coupling 146 located at the proximal end 144 for attachment to a respirator (not shown). While not shown in this view, a ventilation passageway can also be provided to the distal end 142 if desired.

The conduit 136 also houses one or more liquid passageways that supply liquid from a liquid inlet coupling 148 to the distensible sac 134, and circulate liquid back to a liquid outlet coupling 150. The couplings 148 and 150 may be connected to a self-contained liquid supply system or a larger system containing a separate power supply circuitry and fluid flow module that circulates a degassed liquid at a controlled temperature for cooling the transducer assembly 132 and providing an acoustic coupling between the transducer assembly 132 and the pulmonary tissues and tumor 152. It is also possible to derive the coupling/cooling fluid from the liquid infusion system that supplies liquids to the lung. The sac 134 is constructed of a thin, pliable material, such as polyurethane, that readily conforms to the shape of an abutting pulmonary tissue or tumor to facilitate heating of the tumor. A fiber-optic assembly is shown as part of the applicator 130 having one or more optical fibers (not shown) passing through the liquid sac 134 and the transducer 132. The fiber-optic assembly includes a lens 156 positioned on the distal end 142 of the conduit 136, an optical coupler 158 at the proximal end 144 to facilitate viewing through the lens 156 as previously described, and a light source that is supplied through cables 160 that also include power cables for the transducer assembly 132. A cuff 162 typically is formed on the conduit 80 distal to the transducer assembly 132, to be inflated and deflated through a cuff fluid line coupling 164 that is connected to a source of pressurized liquid or gas. This cuff 162 serves primarily an anchoring function, to assist and maintain acoustical positioning of the transducer 132 and liquid-filled sac 134 at the tumor site 152.

Both of the intracavitary applicators 76 and 130 described above can be positioned in the bronchial tree by first locating the tumor target via a flexible bronchoscope that indexes the lengths of the passageways and the position of the tumor. The applicator is then guided down the airways with the aid of a bendable rod, as described above. Such a rod is first bent slightly and then fed down one of the inner passageways of the applicator. The bend of the rod is sufficient to bend the distal end of the applicator in the desired direction. Supplementing this steering approach is a system of fiduciary marks taken from or correlated with the bronchoscope traversal that establishes the length required to descend down the airways. Finally, the fiber-optic assembly 154 can be used alone or in conjunction with the rod to accurately position the transducer assembly adjacent to the tumor to be treated.

The intracavitary applicator 130 may also be configured for hyperthermic treatment in other body cavities, e.g., the mouth, esophagus, uterus, or rectum, in which case a cuff may be provided for auxiliary anchoring purposes.

Figure 6:
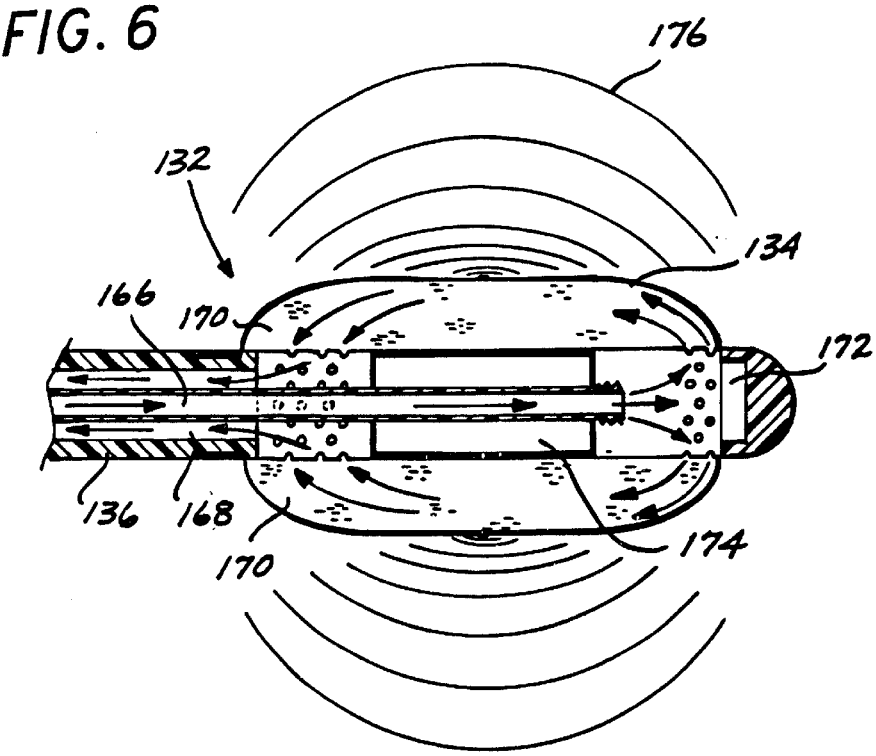

FIG. 6 illustrates in greater detail a representative transducer assembly 132 for use in conjunction with the distensible acoustic-coupling sac 134. Here, the conduit 136 is shown in cross section having a liquid inlet passageway 166 centrally positioned within a concentric liquid return passageway 168. The liquid 170 passes through a manifold 172 into the lumen of the sac 134 to distend the sac 134 and circulate around the transducers 174. The liquid 170 then passes through the manifold 172 and into the return passageway 168. The circulation of the liquid 170, which is normally degassed water, aids in cooling the transducers 174 and provides an acoustic coupling for the ultrasound waves 176. Although not shown, it is to be understood that cuff fluid lines and the fiber-optic assembly lines can be constructed to pass axially through the sac 134 and the transducers 174 to distal positions along the conduit 136.

Another embodiment of the invention provides a means for delivering biological agents, through the pulmonary air passages of a patient, for treating, controlling and/or diagnosing pulmonary and/or systemic, diseases, conditions and/ or abnormalities. In this embodiment of the invention, the biological agents are delivered into at least a portion of the pulmonary system via the implementation of liquid lavage/ventilation of at least a portion of the patient's pulmonary air passages. Specifically, in this embodiment of the invention, biological agents are delivered into at least a portion of the patient's pulmonary system via liquid-born agents which are either recirculated in and out of the preselected portion of the pulmonary air passages in a liquid lavage fashion or maintained static (non-recirculated) for extended periods of time. If breathable liquids are used, pulmonary delivery of biological agents can be performed with simultaneous pulmonary ventilation.

As used herein, the phrase "biological agents" refers not only to physiologically-active agents (e.g., chemotherapeutic agents), but also to physiologically-inert agents (e.g., diagnostic agents).

As used herein, the phrases "liquid lavage", "liquid ventilation", and/or "liquid lavage/ventilation" individually and collectively refer to gravity-assisted and/or mechanically-assisted passing of liquid mediums through at least a portion of a patient's pulmonary air passages. The liquid mediums being passed therethrough need not, necessarily be "breathable" (e.g., in those instances when a liquid lavage process is employed solely for washing/rinsing a portion of the lungs). However, when employed in liquid ventilation, it is preferable that the liquids have the ability of gas exchange.

This embodiment of the invention, pertaining to the pulmonary administration of biological agents, provides a method for treating, controlling and/or diagnosing a patient's pulmonary-related diseases, conditions and/or abnormalities. This new method is especially useful when treating, controlling and/or diagnosing conditions wherein blood is preferentially shunted away from diseased pulmonary regions and, thereby, systemically delivered agents are at least partially precluded from reaching these regions. This embodiment is also useful as a means for introducing agents such as surfactants, steroids, antibiotic agents, chemotherapeutic agents, chemotactic agents, diagnostic agents, and the like, primarily, if not exclusively, into the pulmonary system, when systemic absorption of such agents is undesirable.

The implementation of liquid lavage/ventilation techniques, as a vehicle for delivering biological agents to at least a portion of a patient's pulmonary system, is of particular importance for many reasons. Examples of some of the advantages associated with the pulmonary administration of biological agents includes, but are not limited to, the following: (a) it results in the homogenous delivery of the agents throughout the pulmonary system for treating, controlling and/or diagnosing diffuse diseases, conditions and/or abnormalities, while simultaneously supporting gas exchange, if desired; and/or (2) it can be employed to selectively deliver biological agents to desired areas of the pulmonary system for treating controlling and/or diagnosing local diseases, conditions and/or abnormalities. In each of the aforementioned instances, the process of the selective pulmonary administration of biological agents minimizes normal, healthy, delicate pulmonary tissues from being exposed to toxic agents, such as is often encountered during conventional systemic chemotherapeutic and/or diagnostic techniques.

When practicing the embodiment pertaining to the pulmonary administration of biological agents, the biologically active agents, passing through at least a portion of the patient's pulmonary air passages, can react with, and/or diagnose, the patient's biological system in a number of ways. For example, the biological agents introduced in accordance with the invention, by pulmonary administration, may be used in the following ways: (a) to react directly on and/or diagnose the patient's pulmonary system, (b) to react on and/or diagnose both the patient's pulmonary and systemic system, and/or (c) to differentially react on and/or diagnose specified regions of the patient's pulmonary system.

Through research, it was discovered that there are many advantages of delivering biological agents directly to the surface of the pulmonary air passages (e.g. lungs) via liquid lavage/ventilation. Some of the more important advantages include, but are not limited to, the following:

1. The delivery of the desired biological agents directly through a patient's pulmonary air passages is enhanced by several physiological principles, such as, for example, (a) the large exchange surface area of the lung (i.e., from about 50 to about 100 $m^2$), (b) the entire cardiac output passes through the pulmonary capillary bed, (c) the thin barrier (i.e., alveolar wall thickness) and the short diffusion distances enhances absorption of the agent, and (d) the uniform distribution of low surface tension liquids throughout the pulmonary system.

2. In many cases, the action of the biological agents (e.g., surfactants to lower pulmonary surface tension, bronchodilators to relax airway smooth muscle, pulmonary vasodilators to increase pulmonary blood flow, steroids for lung inflammation, chemotactic agents, chemotherapeutic agents and/or diagnostic agents for lung cancer, and the like) are exclusively directed to a portion of the patient's pulmonary air passages (e.g., lungs) and would be undesirable in the rest of the body.

3. In diseases and/or abnormal lungs, a common problem is poor distribution of pulmonary blood flow and ventilation. This problem is obviated in the liquid-filled lung, in that liquid and blood flow are uniformly distributed and matched. This physiological principle enables efficient exchange of biological agents into a lung where exchange would otherwise be impossible.

4. Liquids can be selectively directed to specific regions of the patient's pulmonary air passages by a number of different conventional means, such as a bronchoscope, a conventional catheter or even a specialized catheter, similar to that employed in the hyperthermia treatment mentioned earlier. This capability of selectively directing liquids comprising biological agents would be particularly useful when only a specific region of the patient's pulmonary system requires delivery of such agents (e.g., chemotherapeutic cancer drugs which may be harmful to normal, healthy lung and body tissues in high concentrations and agents which facilitate pulmonary debridement).

5. In the case of systemic vascular compromise or shock, intravascular administration of agents is ineffective under conventional practices. However, the passage of the necessary biological agents through at least a portion of the patient's pulmonary air passages by liquid lavage/ventilation techniques provides a direct route for agent administration.

When practicing the embodiment of the invention pertaining to the pulmonary administration of biological agents, the selected liquid is augmented with the selected biological agents. These agents can be present in the liquid medium in any suitable form (e.g., bulk form, a suspension, a dispersion, a liquid form, an emulsion form, encapsulized and the like and/or combinations thereof). The particular form of the biological agent, will depend upon many different variables (e.g., the specific agent being used, the area being treated and/or diagnosed, the condition and/or abnormality being treated, controlled and/or diagnosed, the parameters under which the liquid lavage/ventilation process is performed, etc.).

Moreover, the selected biological agents can be incorporated into the liquid medium by any suitable technique. Examples of suitable incorporation techniques include, but are not limited to, injection, blending, dissolving, employing conventional incorporation procedures and incorporation of specific incorporation procedures (see, e.g., FIG. 38).

Any suitable biological agent can be employed when practicing this embodiment of the invention. Examples of suitable biological agents include, but are not limited to, anti-cancer agents, vasoconstrictors, vasodilators, bronchoconstrictors, bronchodilators, surfactants, steroids, antibiotic agents, chemotactic agents, toxins, antibody-linked radionuclides, diagnostic agents, contrast agents, and the like, and/or combinations thereof.

When employing vasoconstrictors, vasodilators, bronchoconstrictors and/or bronchodilators (e.g., epinephrine, acetylcholine, priscoline and sodium nitroprusside), they can be used in any suitable amount necessary to achieve the desired results, in view of the specific conditions, diseases and/or abnormalities present. For example, the amount of these biological agents can range from between about 0.001 to about 10.0 mg for each kilogram of body weight of the patient whose physiological conditions, diseases and/or abnormalities are being controlled, diagnosed and/or treated in accordance with this embodiment of the invention. In another instance, it may be desirable to have the amount of these biological agents range from between about 0.004 to about 7.0 mg/kg, or from between about 0.007 to about 4.0 mg/kg, or from between about 0.01 to about 1.0 mg/kg.

As indicated above, the amount of biological agent employed depends, in part, on the specific set of circumstances revolving around each individual case.

In addition to the above, this embodiment is particularly useful for delivering anti-cancer drugs (e.g., adriamycin), toxins, antibody-linked radionuclides, and the like and/or combinations thereof, to at least a portion of the patient's pulmonary system by being passed through the patient's pulmonary air passages.

Any suitable liquid can be used as the liquid carrier when practicing the embodiment pertaining to the pulmonary administration of biological agents. As stated earlier, depending upon the specific circumstances, the liquid carrier need not be breathable. In most instances, however, the liquid carriers employed are breathable.

Particularly useful breathable liquids which can be used as the liquid carrier include, but are not limited to, perfluorochemicals, saline, silicone and vegetable oils, and the like. Of the aforementioned liquids perfluorochemicals (e.g., perfluorocarbon) liquids are presently preferred.

Some of the reasons for preferring perfluorochemicals include, but are not limited to, (a) they have a high solubility for respiratory gases, thereby being able to maintain ventilation during therapeutic and/or diagnostic procedures; (b) they have a low surface tension which facilitates the uniform distribution of the liquids and the biological agents throughout the pulmonary system; and/or (c) they are generally biologically inert, thus preventing possible side-effects due to the liquid carrier and the biological agent interacting. It should be noted, however, that other liquids can be preferred over perfluorochemicals, depending upon the specific circumstances and the desired results.

There are a number of clinical conditions when liquid lavage (washing) of the pulmonary system is necessary to debride the alveolar surfaces of unwanted secretions, particles, toxins, etc. (e.g., alveolar proteinosis, cystic fibrosis, aspiration syndromes, and the like). Conventional lavage procedures generally employ the use of isotonic saline as the washing media since it is relatively non-damaging to the alveolar surface. However, because saline does not carry a substantial amount of oxygen to support respiration, only one lung can be washed at a time. The other lung is maintained with 100% oxygen. This imbalance usually results in hypoxia during and after conventional the lavage procedures.

In several research reports, it has been documented that it is possible to wash both lungs, simultaneously, if a breathable liquid (e.g., perfluorocarbon) is employed as the washing media. In view of the embodiment of the present invention pertaining to the pulmonary administration of biological agents, an extension of the concept which employs breathable liquids as the washing media, in a liquid lavage procedure, is to augment the breathable liquid with an effective solvent appropriate for the particular injury to the patient's pulmonary air passages. For example in the case of Adult Respiratory Distress Syndrome (also referred to herein as "ARDS"), the breathable liquid may contain a suspension of antiproteases to more effectively perform the following functions: (a) inhibit protein leakage, (b) wash out alveolar debris and (c) maintain gas exchange. Furthermore, in the case of aspiration syndromes, the breathable liquid may contain an agent to neutralize or buffer the action of the aspirant on the lung surface. For example, if the aspirant is of an acidic nature (e.g., gastric contents), the breathable liquid may be buffered with bicarbonate to balance the pH and minimize lung epithelial damage.

When practicing the embodiment of the invention, wherein the biological agents are introduced via a liquid lavage procedure, the liquid carrier (augmented with the desired biological agents, whether in bulk, suspension, dispersion, emulsion and/or encapsulization form) can be placed in an inspiratory reservoir ($R_I$). This inspiratory reservoir is generally suspended above the patient and is in open communication with at least a portion of the patient's pulmonary air passages. For example, two ends of a Y-piece can be used to interconnect the $R_I$ with the patient's endotracheal tube.

Gas ventilation is generally interrupted when instilling the liquid functional residual capacity from the $R_I$. This residual capacity may contain at least a portion of the desired biological agents. Gas and/or liquid ventilation is then resumed and/or initiated depending upon whether the process is (a) a total or partial ventilation, (b) a total or partial lavage with breathable liquid, or (c) a total or partial lavage with a non-breathable liquid.

After the resumption and/or initiation of gas and/or liquid ventilation, tidal volumes of a liquid washing medium are passed through the patient's pulmonary air passages. These tidal volumes of liquid medium may contain at least a portion of the desired biological agents.

In liquid lavage techniques, the tidal volumes of liquid can be passed through the desired portion of the patient's pulmonary air passages via gravity assistance, mechanical assistance or a combination of both. Similarly during liquid lavage techniques, the liquids can be removed from pulmonary air passages via gravity and/or mechanical assistance. If a Y-piece is employed as described above, the expired liquids can pass through its remaining port and be deposited into an expiratory reservoir.

Although the residual capacity of liquid remains in the pulmonary air passages throughout the entire lavage/ventilation procedure, each tidal volume of liquid is held within the patient's lungs for a period of time necessary to achieve the desired results, while maintaining the necessary exchange of gases, if necessary. For example, the liquid can be retained in the patient's pulmonary system for a period of time ranging from between about 60 seconds to about 1 second. In most instances, however, it will not be necessary to retain the tidal volume liquid in the patient's pulmonary system for more than about 30 seconds.

Similarly, the frequency of the tidal volumes of liquid also depends upon the specific results desired.

On the other hand, when practicing the embodiment of the invention, wherein biological agents are introduced via a liquid ventilation procedure, the liquid ventilation process can also be achieved using a gravity-assisted system and/or a mechanically-assisted system. In this procedure, breathable liquid is generally oxygenated to maintain the arterial oxygen tension ($P_aO_2$) constant; and carbon dioxide ($CO_2$) is generally scrubbed from the system. Thereafter, the $pO_2$ and $pCO_2$ of the liquid are typically sampled, analyzed and/or controlled during the ventilation process to ensure constant inspired gas tensions and drug delivery levels. It should be noted that the augmentation of the liquid carrier with the biological agents can be performed either before, during and/or after the liquid is oxygenated.

Once the patient is connected to the liquid ventilation system which is being used as the vehicle for the pulmonary delivery of biological agents, tidal volume ($V_T$) and functional residual capacity (FRC) is preferably monitored and/or controlled. Generally, ventilation schemes will be initially adjusted for effective carbon dioxide elimination and maintenance of physiological arterial $CO_2$ tension ($P_aCO_2$). In addition to the above, breathing frequency (f), $V_T$ and FRC are also generally monitored and/or adjusted to obtain physiological $P_aO_2$ and $P_aCO_2$.

Regardless of whether a liquid lavage and/or ventilation technique is employed as the vehicle for carrying biological agents to the patient's pulmonary system via the patient's pulmonary air passages, heart rate, arterial pressure, hemoglobin-oxygen saturation, arterial blood gas tensions, and/or pulmonary function are generally evaluated before and during the process.

When practicing the embodiment of the invention pertaining to the pulmonary administration of biological agents via liquid lavage/ventilation, the liquid medium can be heated or cooled to temperatures above or below the patient's normal body temperature depending, again, on the specific conditions and/or desired results. For example, in addition to the liquid medium being at our about the patient's normal body temperature, it can also be greater or less than that temperature.

For example, the temperature of the liquid medium, either before and/or during the liquid lavage/ventilation process, can range from between about the normal body temperature of the patient whose physiological conditions, diseases and/or abnormalities are being diagnosed, controlled and/or treated to about 20% above the patient's normal body temperature. Generally, if such a hyperthermic treatment is desired, the temperature of the liquid medium can range from about the patient's normal body temperature to about 15% greater than the patient's normal body temperature, or from about the patient's normal body temperature to a temperature about 10% greater than the patient's normal body temperature, or from about the patient's normal body temperature to a temperature about 5% greater than the patient's normal body temperature, or from about the patient's normal body temperature to a temperature about 1% greater than the patient's normal body temperature. In each instance, the liquid medium's temperature will depend upon the specific circumstances present and the results desired.

Moreover, the temperature of the liquid medium, either before and/or during the liquid lavage/ventilation process, can range from between about the normal body temperature of the patient whose physiological conditions, diseases and/or abnormalities are being diagnosed, controlled and/or treated to about 20% below the patient's normal body temperature. Generally, if such a hypothermic treatment is desired, the temperature of the liquid medium can range from about the patient's normal body temperature to about 15% less than the patient's normal body temperature, or from about the patient's normal body temperature to a temperature about 10% less than the patient's normal body temperature, or from about the patient's normal body temperature to a temperature about 5% less than the patient's normal body temperature, or from about the patient's normal body temperature to a temperature about 1% less than the patient's normal body temperature. As above, the temperature of the liquid medium will depend upon the specific set of circumstances present and the results desired.

In addition to the above, it is also within the scope of this invention for the liquid medium's temperature, either before and/or during the liquid lavage/ventilation, to range from between about 10% below to about 10% above the normal body temperature of the patient whose physiological conditions, diseases and/or abnormalities are being diagnosed, controlled and/or treated. In other instances, however, it may be desirable to have the temperature of the liquid medium range from between about 5% below to about 5% above the patient's normal body temperature, or from between about 3% below to about 3% above the patient's normal body temperature, or from between about 1% below to about 1% above the patient's normal body temperature.

When practicing the embodiment pertaining to the pulmonary delivery of biological agents, the particular temperature range of the liquid medium, either before and/or during the liquid lavage/ventilation, will depend upon the desired results and specific circumstances of each individual implementation.

As stated earlier, the embodiment of the invention, pertaining to the pulmonary administration of biological agents, is especially useful for treating certain types of lung cancer. The phrase "lung cancer" as used herein, generally refers to tumors arising in major airways and pulmonary parenchyma.

Therapeutic treatment of lung cancer with chemotherapeutic agents (e.g., adriamycin, toxins, antibody-linked nuclides, etc.) may have devastating effects on systemic tissues when delivered at the high levels which are generally necessary for the treatment of many types of lung cancer.

On the other hand, the embodiment of the present invention, which employs liquid lavage/ventilation techniques for the pulmonary administration of biological agents, provides a successful means for delivering therapeutically high levels of anti-cancer agents to the lung surface (cancer site) relative to the systemic tissues, therefore minimizing adverse side effects.

Another pulmonary abnormality, which can be chemotherapeutically treated with the embodiment of the present invention pertaining to the pulmonary administration of biological agents, is respiratory distress syndrome. Respiratory distress syndrome is characterized in both neonate and adults by their inability to effectively exchange oxygen and carbon dioxide as a result of lung immaturity (infants only), damage, or a combination of both.

Because breathable liquids, such as perfluorocarbons, have low surface tensions and high solubilities for respiratory gases, when practicing the present invention, such liquids can be used to homogeneously expand the lung with low pressures, while simultaneously supporting gas exchange and delivering biological agents to regions of the lung which are generally not accessible by systemic circulation. In comparison to existing conventional procedures for treating respiratory distress syndrome, the approach employed when practicing the present invention significantly reduces the risk of pulmonary damage.

Particular therapeutic agents which would be applicable in the treatment of respiratory distress syndrome (RDS) include, but are not limited to: exogenous surfactants, antibiotics, steroids, antioxidants, antiproteases, bicarbonate and the like. While all of these agents have proven clinical applicability for treatment of RDS, they have significant limitations associated with their conventional means of delivery. However, the pulmonary administration of these agents, in accordance with the practices of the present invention, (a) provides a means for overcoming most of the limitations encountered by conventional administration techniques and (b) effectively delivers the aforementioned agents to the injured/abnormal regions of the patient's pulmonary system. Moreover, due to the evaporative characteristics of many breathable liquids, practicing the present invention in this manner provides a means for assured deposition of these agents onto the lung surface, without residual interference due to the liquid carrier.

Yet another process, wherein the embodiment of the invention pertaining to the pulmonary administration of biological agents can be employed, is in Airway Smooth Muscle (ASM) Control. In addition to controlling pulmonary vascular smooth muscle for pulmonary circulation, by practicing the present invention, it is now possible to augment certain breathable liquids (e.g., perfluorocarbons) with therapeutic agents which control ASM and, therefore, airway resistance to flow.

In the case of severe asthma, the ASM contracts such that respiration is impeded and hypoxia and hypercapnia generally results. We have demonstrated that the addition of a ASM agonist and antagonist to a breathable liquid can significantly alter ASM tone and, subsequently, affect ventilating pressures. Specifically, in Example 12 of this invention (infra), acetylcholine was injected into a perfluorocarbon liquid during inspiration. As that Example demonstrates, there was a rapid increase in tracheal pressure due to airway constriction. Airway dilation, on the other had, has also been demonstrated with the addition of other biological agents, such as isoproterenol and epinephrine, to a perfluorocarbon ventilation liquid.

The embodiment of the invention pertaining to the pulmonary delivery of biological agents can also be useful for diagnosing particular conditions, diseases and/or abnormalities in the pulmonary system. For example, contrast agents (e.g., radioopaque agents) can be augmented into the liquid medium to enhance structural delineation of the patient's pulmonary air passages. Moreover, agents which can evaluate diffusional barriers, pulmonary blood flow, and/or distribution of ventilation can also be employed.

When practicing any embodiment of the invention, it is generally necessary to monitor and/or control certain mechanical and/or physiological parameters. The particular parameters which would fall into this category will depend greatly upon specific circumstances surrounding the specific application. Examples of variables which are generally taken into consideration when practicing the invention include, but are not limited to: the technique being employed for liquid ventilation/lavage, the particular pulmonary condition being treated, diagnosed and/or controlled the particular method of treating, diagnosing and/or controlling the particular condition, and the likes and/or any combination thereof.

Parameters which are most often monitored and/or controlled generally can be divided into three categories. The first category includes the monitoring and/or control of parameters, such as breathing frequency, inspiratory and expiratory times, volume, flow rate, and/or pressure. The second category includes the monitoring and/or control of parameters, such as the temperature of the inspired liquid. The third category includes the monitoring and/or regulation of parameters, such as oxygen and carbon dioxide tensions of the inspired liquids. While the aforementioned list of categories includes those parameters which are most likely to be monitored and/or controlled, is not intended to be an exhaustive list.

As can be seen from the above disclosure, the pulmonary administration of biological agents through at least a portion of the patient's air passages is also a means to directly access cardiac output for the infusion of selected agents when systemic collapse precludes delivery via intravascular administration.

As stated earlier, any suitable technique can be employed to combine the selected biological agent and the selected liquid carrier. While not necessarily the preferred technique, one of the many examples of an apparatus and method for producing a uniformly dispersed phase of a biological agent in a liquid medium is now described. The term biological agent used in conjunction with the following description, is in a liquid phase or can be converted into a liquid-phase. Examples of such biological agents include, but are not limited to, exogenous surfactants, antibiotics, steroids, antioxidants, antiprotease, bicarbonate, and other similar chemotherapeutic and/or diagnostic agents.

This representative apparatus produces a cloud or liquid-liquid mist of uniformly sized agent-containing droplets with a liquid carrier (e.g., a perfluorocarbon liquid), wherein the droplets are a uniformly dispersed phase and the liquid carrier is a continuous phase. This method is useful for producing agent/carrier combinations that form a dispersion or suspension (where the carrier and agent are immiscible to a substantial degree), or a solution (in the case of soluble constituents).

Referring to FIG. 38, an apparatus 208, that can be used to provide a uniformly dispersed biological agent within a source of a liquid carrier 210, includes a longitudinal conduit 212 that carries the agent-containing fluid to a delivery device (not shown) for introducing liquid 210 in the at least a portion of the patient's pulmonary air passages. Along the length of conduit 212, upstream from the end where liquid 210 enters the preselected pulmonary air passages, is header 214.

Header 214 is divided into an inner chamber 216 and an outer chamber 218. Inner chamber 216 occupies the central portion of header 214, and outer chamber 218 surrounds inner chamber 216 and occupies the balance or outer portion of header 214. The upstream end of inner chamber 216 communicates with source 220 for the aqueous solution or other liquid-phase biological agent(s) 220 through conduit 213. Outer chamber 218 communicates with liquid carrier source 210 through conduit 211. Although conduit 211 is illustrated as being of the side of header 214, it can also be on the top or bottom of header 214 or on the side where conduit 213 joins the header. Inner chamber 216 and outer chamber 218 are separated from each other so mixing of the aqueous solution or other liquid-phase agent(s) and the liquid carrier, within header 214, is prevented.

Downstream end of outer chamber 218 includes a plurality of orifices 224 through which liquid carrier 210, within outer chamber 218, can pass in an evenly distributed manner into conduit 212. Liquid carrier 210 flows through conduit 212 in the direction of arrows 226.

Downstream end of inner chamber 216 communicates with upstream end of a plurality of longitudinal tubes 228 that extend lengthwise in a downstream direction within the central portion of conduit 212. The downstream end of each tube 228, opposite inner chamber 216, includes nozzle 230. When the solution of biological agent(s) is forced through nozzle 230, small droplets 234 are formed. The plurality of tubes 228 are spaced apart in a side-by-side relationship so that liquid carrier 210, which enters conduit 212 through orifices 224, can flow between and around tubes 228.

In most cases, the length of tubes 228 will be such that liquid carrier 210, which passes through orifices 224, can achieve a laminar flow before passing by nozzles 230. Laminar flow is preferred so that the dispersed droplets of the aqueous solution or other liquid-phase biological agent (s), as described hereinbelow in more detail, will be uniformly dispersed throughout liquid carrier 210.

Upstream from nozzles 230 and downstream from inner chamber 216, tubes 228 are supported by a plate 232 that passes upward, perpendicular to the longitudinal axis of tubes 228, through the top side of conduit 212. Plate 232 supports each tube 228 near nozzle 230 so that nozzles 230 are positioned uniformly and substantially in the center of conduit 212. In a preferred embodiment, plate 232 is attached to a high-frequency driver, such as an ultrasound transducer, that can vibrate the nozzles 230 at a high frequency to stimulate the natural instability of the droplets that form at the nozzles' tips and promote the formation of the small droplets of controlled size. The vibration can be in a vertical plane or a horizontal plane relative to plate 232. As an alternative to vibration, controlled-size droplets of the aqueous solution or other liquid-phase biological agent(s) can also be formed by providing oscillatory pulses of pressure to the liquid in tubes 228. Pressurizing the liquid in tubes 228 can be accomplished by pulsing the source 220 pressure of the aqueous solution or other liquid-phase agent (s) at appropriate frequencies.

In operation, liquid carrier 210 is introduced into outer chamber 218 through conduit 211. Liquid carrier 210 fills outer chamber 218 and passes through orifices 224 and into conduit 212 where it passes down conduit 212 and in between and around tubes 228.

An aqueous solution or other liquid-phase biological agent(s) is introduced into inner chamber 216 through conduit 213. The solution fills inner chamber 216 and enters tubes 228. The solution exits tubes 228 through nozzles 230 which produces small, uniformly sized droplets 234 of the solution. Since liquid carrier 210 surrounds nozzles 230, the droplets of liquid drug are dispersed into the liquid carrier as they separate from nozzles 230. Formation of uniformly sized droplets of preferred diameters may be promoted by either vibrating plate 232 or by providing oscillatory pulses of pressure to the source of the aqueous solution of liquid-phase agent(s) as described above.

The size of droplets 234 can be controlled by varying the size and shape of the nozzles, the temperature of the source liquid 220, and/or the mean pressure provided from the source of the aqueous solution or other liquid-phase drug(s). In addition, the frequency, magnitude, and shape of the oscillation signal (e.g., sine wave vs. square wave) of the vibration, or the frequency and magnitude of the pulses of pressure, can be modified to selectively control the size of the droplets. Other factors such as drug vehicle temperature and chemical additives that effect physical properties (e.g., surface tension and viscosity) of the carrier 210 liquid (without changing the therapeutic effects or toxicity of same) can also be manipulated to control the formation of the droplets.

It should be understood that the apparatus described above is but one representative embodiment by which one can achieve this liquid-liquid mist of uniformly sized droplets in a carrier liquid. The motivation to introduce drugs in this manner is particularly important with immiscible liquids of substantially different densities, such as in the case with aqueous-based drugs and perfluorocarbon liquids. By introducing the dispersed drugs in the flow stream just before entering the patient, the time for buoyancy-driven separation of the two constituents is minimized and the biodistribution of the drug is thereby enhanced.

It should also be understood that the embodiment of the invention pertaining to the pulmonary administration of drugs also includes the administration of solid, insoluble drugs. In these instances, for example, a liquid-solid phase may be formed by dispersing and/or suspending a fine powder of the drug in the liquid carrier.

The examples which follow are intended to assist in a further understanding of the invention. Particular materials employed, species, and conditions are intended to be illustrative of the invention and are not limitative of the reasonable scope thereof.

EXAMPLES

Based on the well-established biocompatability of perfluorocarbon liquids, the issues most central to determining the feasibility of the disclosed convection and ultrasound hyperthermia techniques were those having to do with the fluid, thermal, and acoustic characteristics of perfluorocarbon liquids and lungs filled with perfluorocarbon liquids. Below, the general physical, thermal, and acoustic properties of candidate liquids are quantified in parameter ranges appropriate to lung heating, as confirmed by isolated lung and in vivo experiments. By employing perfluorocarbon liquids that meet the disclosed criteria, we have demonstrated sustained and controlled convective and ultrasound hyperthermia in large animal lungs in vivo.

Figure 8:
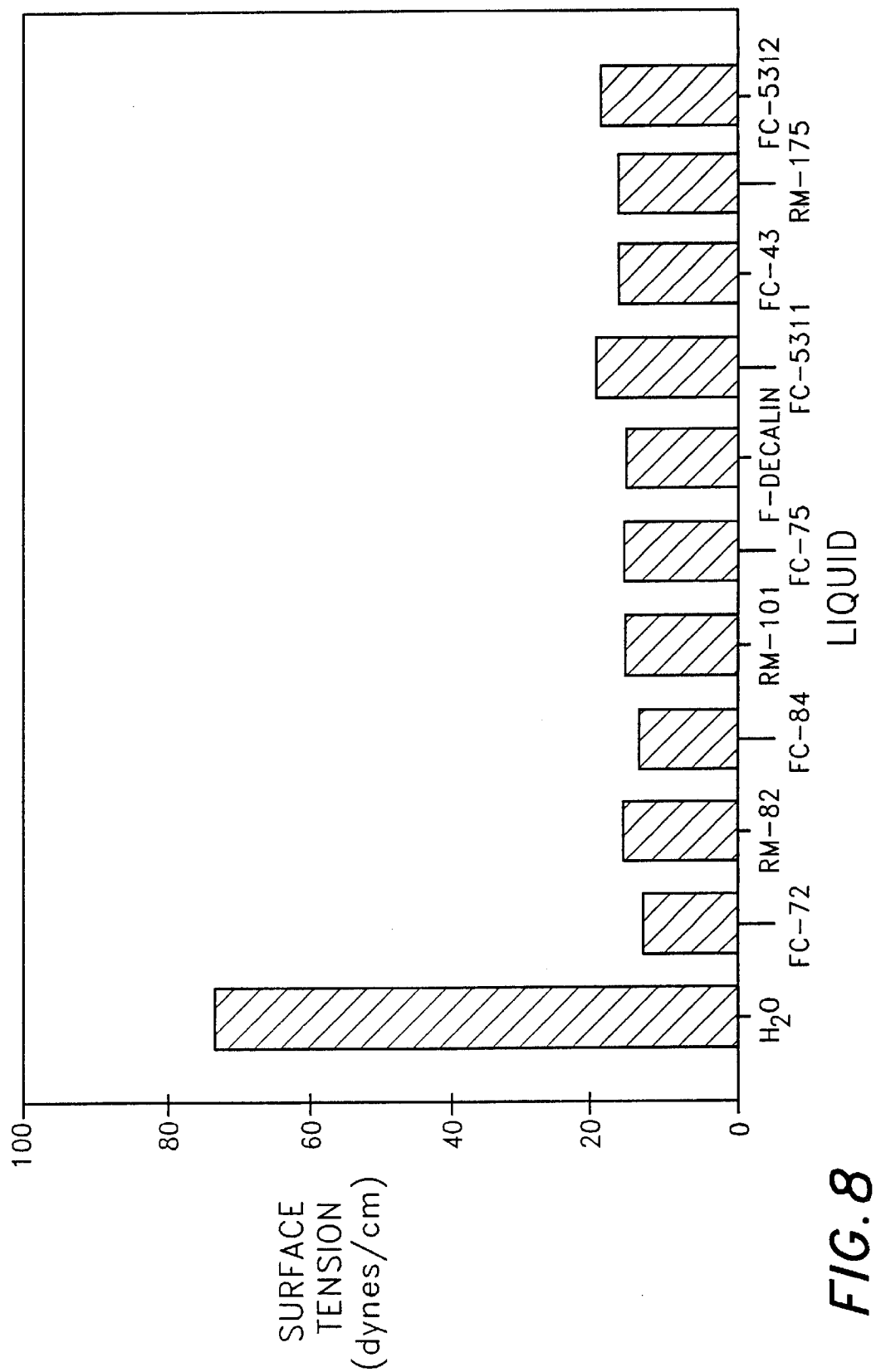

A thorough investigation of the requisite properties of candidate perfluorocarbon liquids was undertaken. From these studies, the most suitable class of liquids was selected for use in confirming animal research. As described below, perfluorocarbon liquids were found to exhibit interesting acoustic properties leading to unexpected but, for the most part, favorable behavior for the purpose of liquid-filled lung ultrasound hyperthermia (LLUH). Chief among the findings are: a) pure perfluorocarbon liquids show measurable non-linear acoustical behavior in intensity ranges suitable to LLUH (<2 W/cm$^2$ @1 MHz), i.e., attenuation increase with power as well as frequency; and b) perfluorocarbons in the lung exhibit significant acoustical scattering of the ultrasound beam. The implications these observations have on the LLUH devices include 1) the need for lower frequencies than are used in conventional superficial ultrasound hyperthermia, 2) a natural advantage exists whereby inherent acoustic beam profile "smoothing" (i.e., flattening of the nearfield diffraction peaks) occurs due to augmented scattering, and 3) a potential benefit favoring focused ultrasound devices may exist in that preferential absorption in their focal regions should result from the nonlinear properties of these particular liquids. In addition, the physical properties of perfluorocarbon liquids have yielded some unexpected advantages. Chief among these are a) the tremendous gas solubility of the liquids make them unique in their ability to quickly and completely fill lung tissue, an advantage important for acoustic coupling, and b) the high gas solubility can likely be exploited to suppress cavitation in the liquid. In addition, the low surface tensions of perfluorocarbon liquids, as shown in FIG. 8, enhance the liquid's ability to readily fill the lung. Also, when a lung becomes filled with liquid, liquid resides on both sides of the vascular spaces, that is, on both the gas side and the blood side. By regulating the amount of liquid infused into the lung space, the blood flow can be controlled. This is because the more fluid that is introduced, the more compressed the lung capillaries become. Reduced blood flow is an important mechanism to reduce heat dissipation and therefore to further localize the treatment to the desired target tissues. Also, the liquid distribution in the lung can be used to control the distribution of pulmonary blood flow.

A wide range of perfluorocarbon liquids were initially considered in an evaluation of physical, thermal, and acoustic properties for selecting the most apt liquids for liquid-filled lung procedures. A summary of these properties is described in detail below.

Example 1
General Characteristics of Perfluorocarbon Liquids

Figure 7:
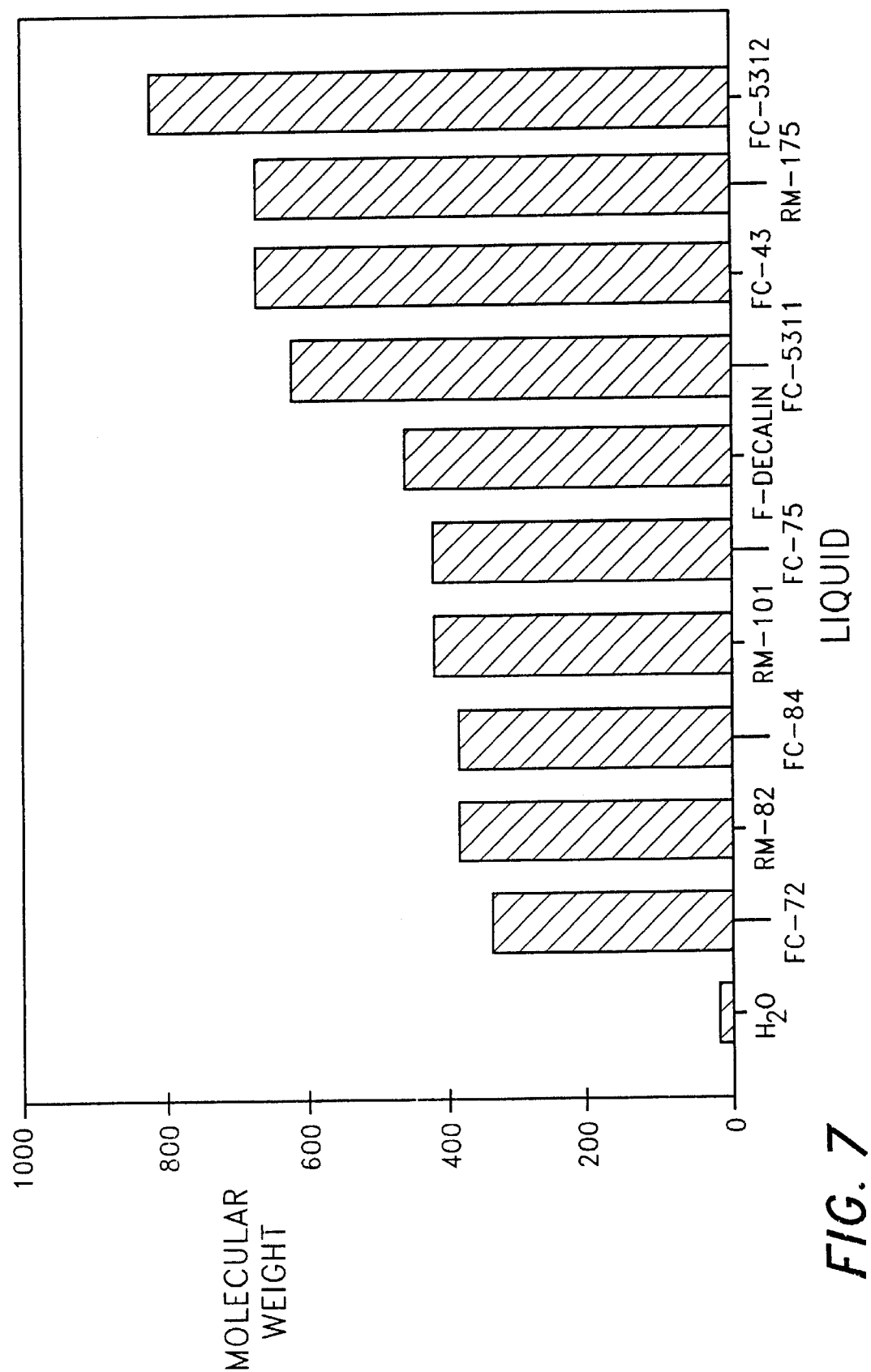

Physical properties: The candidate perfluorocarbon liquids spanned a wide range of molecular weights, as indicated in FIG. 7. For reference purposes, the physical properties of the liquids are presented in the Figures in order of molecular weight, with water properties included for comparison, and, unless otherwise stated, are measured at 25° C.

Fluid flow properties: The predominant force involved in lung inflation is the surface force along alveolar walls due to the action of surface tension effects from the moist lining of the alveoli. The introduction of bulk liquid into the lung significantly reduces these forces since the gas/liquid interface is removed. Further reducing these forces is the fact that perfluorocarbon liquids have some of the lowest surface tensions recorded for liquids (FIG. 8). These combined effects means that the net pressure to maintain inflation in a PFC-filled lung is roughly 20–30% of that required for air inflation [61]. This fact is advantageous for providing cuff isolation of lung lobes and segments since cuff sealing in the airways can be accomplished with lower pressures than for normal clinical bronchial intubation.

Perfluorocarbon liquids are generally poor solvents, being essentially insoluble in water, alcohols, and most biological materials. This is a primary key as to why they are superior to saline as acoustic coupling/heat transfer fluids for liquid-filled lung ultrasound and convection hyperthermia treatments. This immiscibility ensures that the phospholipid surfactant (which maintains low surface tension in alveolar wall moisture) will not readily be washed out of the treated lung. This in turn minimizes the respiratory difficulty which might otherwise occur in a lung after returning to gas ventilation [62].

Figure 9:
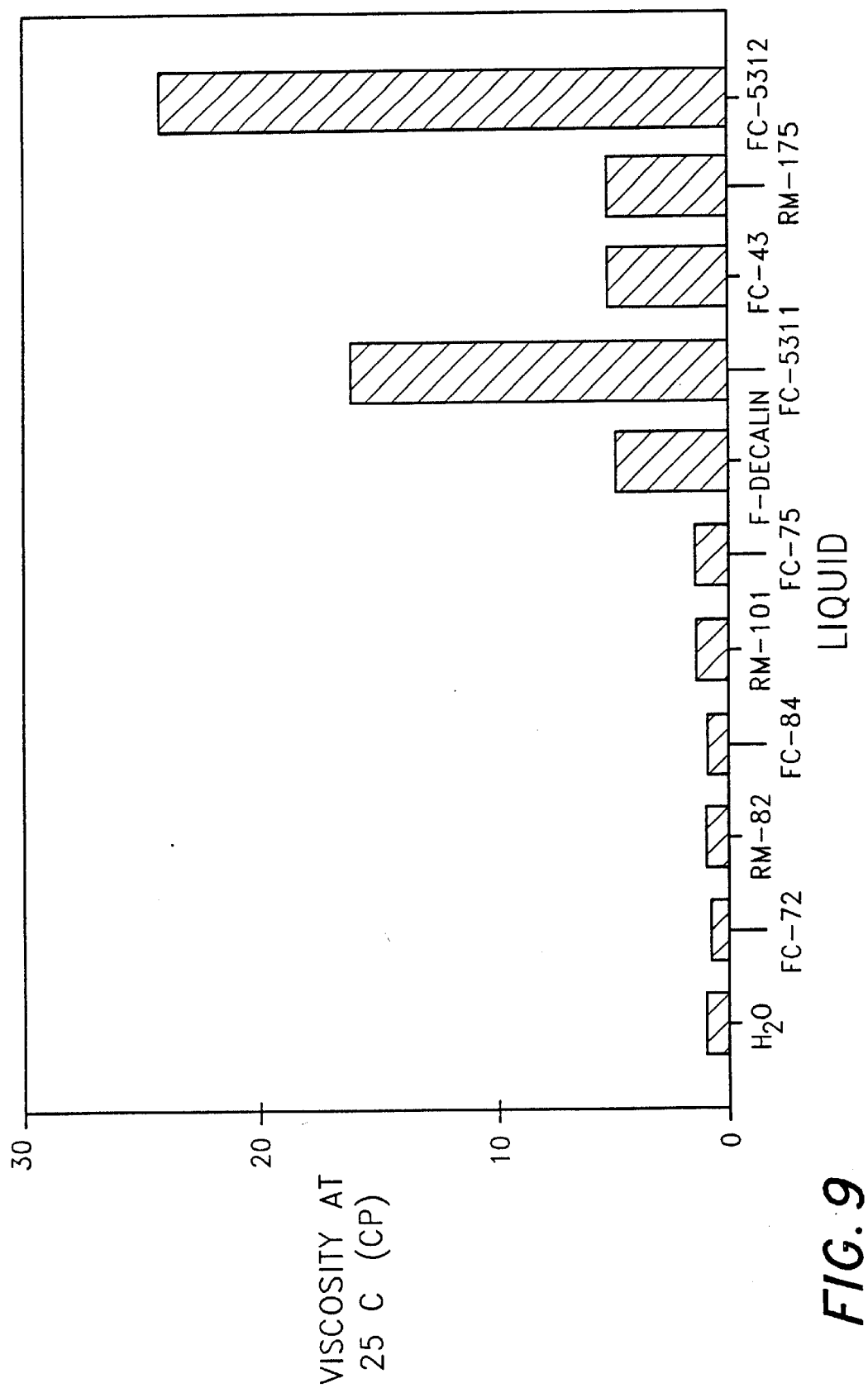
Figure 10:
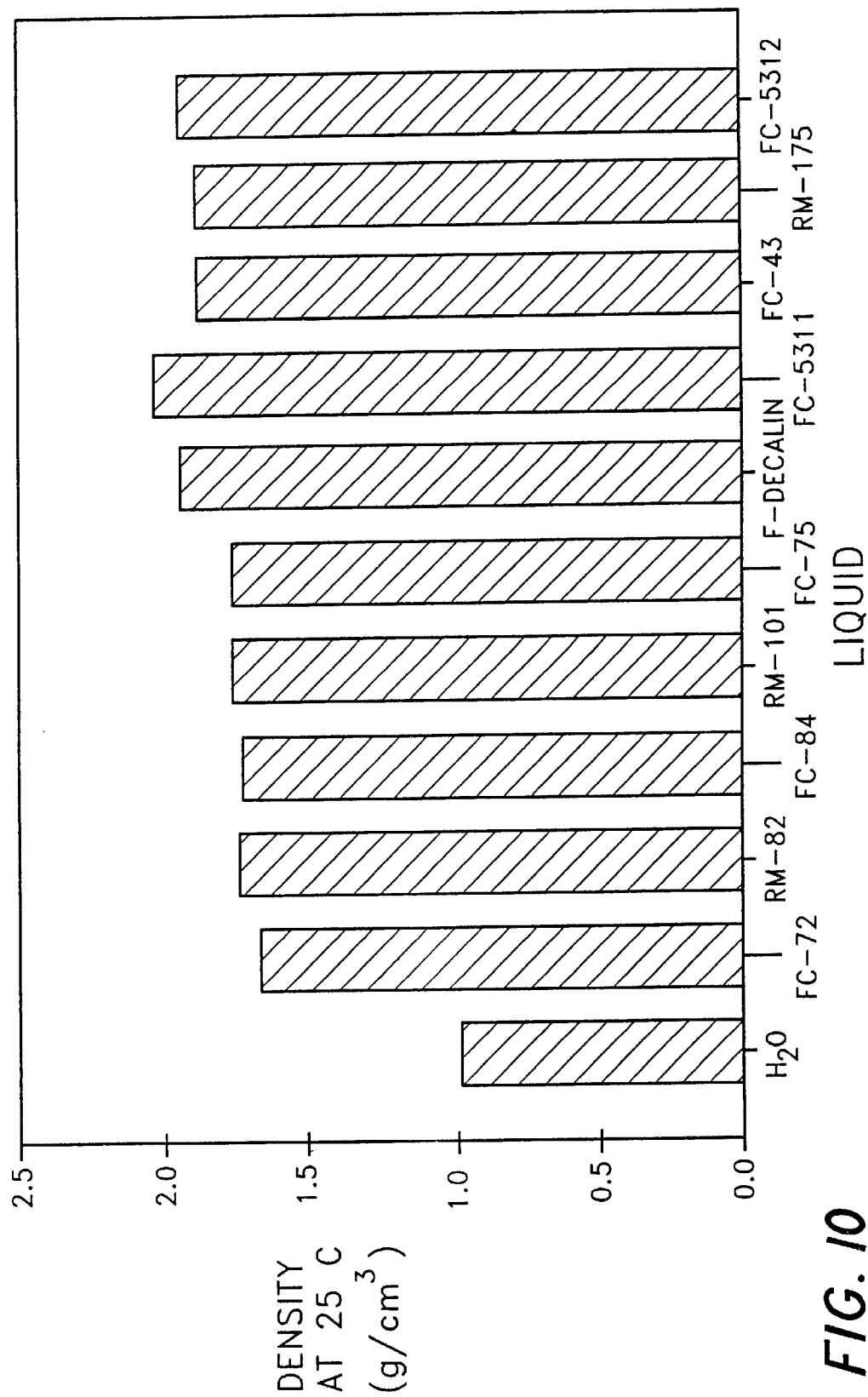
FIG. 10 is a graph indicating the density at 25° C. (g/cm$^3$) of representative perfluorocarbon liquids.

To reduce liquid flow resistance into and out of the lung it is important to minimize the effects of viscous resistance. FIG. 9 shows that some of the perfluorocarbon liquids considered are relatively high in absolute viscosity, compared to water. On this basis, liquids with molecular weights (see FIG. 7 for molecular weights) higher than F-Decalin (i.e., perfluorodecalin) become less desirable. Strictly considered, flow resistance is more closely related to the "kinematic viscosity" (absolute viscosity/density) than absolute viscosity, usually as expressed in the "Reynolds Number" [63]. Considering the higher densities of the liquids (FIG. 10), it is found that those perfluorocarbon fluids with molecular weights below F-Decalin have flow resistance characteristics equivalent to or better than water.

Figure 11:
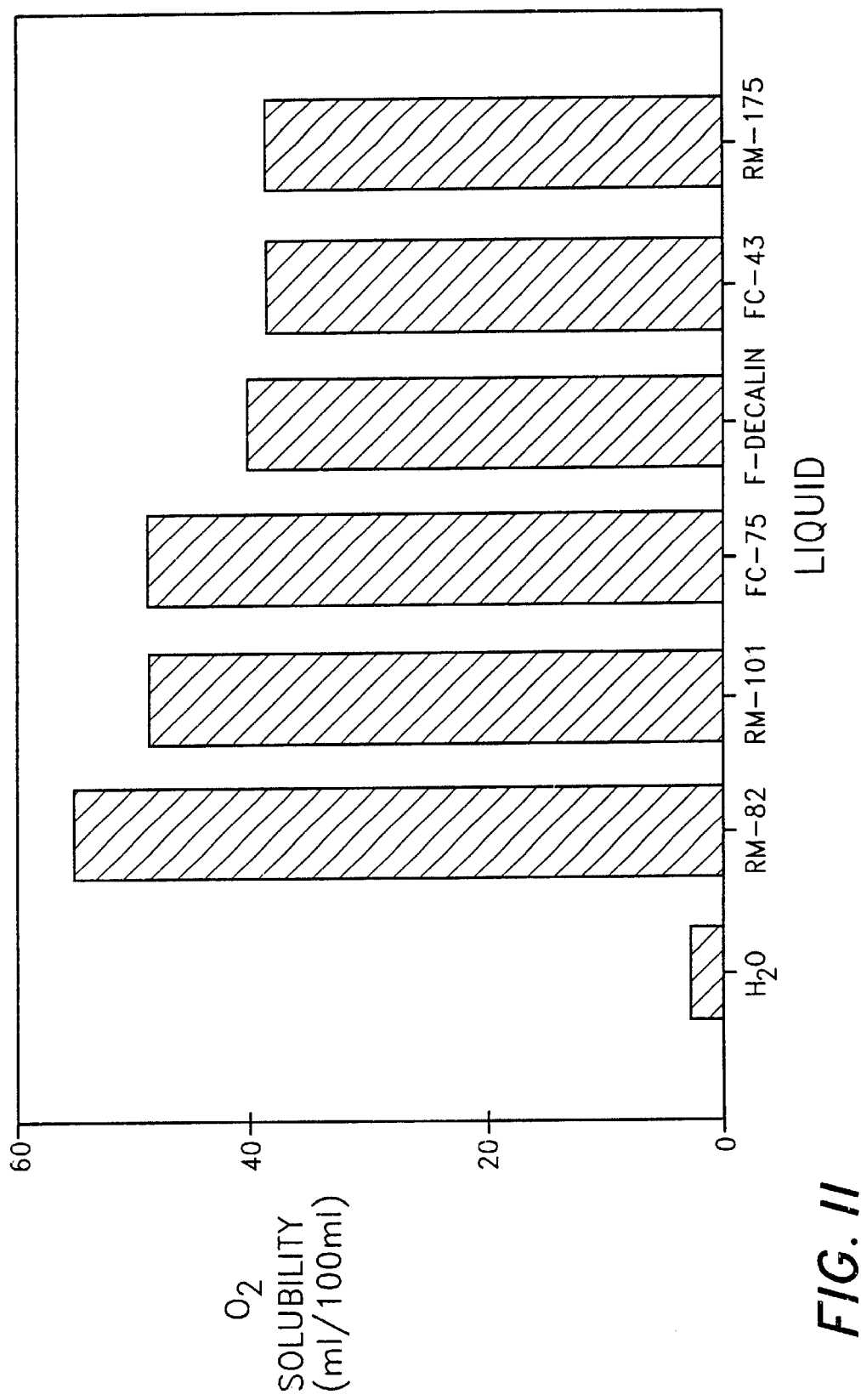
FIG. 11 is a graph indicating the oxygen solubility (ml/100 ml) of representative perfluorocarbon liquids.

Gas solubility: To illustrate the tremendous capability of perfluorocarbon liquids to absorb dissolved gases, FIG. 11 shows the oxygen solubility of six perfluorocarbon liquids in comparison with water. From the standpoint of exploiting this property to suppress cavitation, to assist in lung filling, and, of course, to enable simultaneous lung ventilation during liquid-filled lung hyperthermic treatments (via ultrasound and/or convection), the perfluorocarbon fluids are all roughly equivalent, with a slight preference going to molecular weights below F-Decalin.

Example 2
Thermal Properties of Perfluorocarbon Liquids

Figure 12:
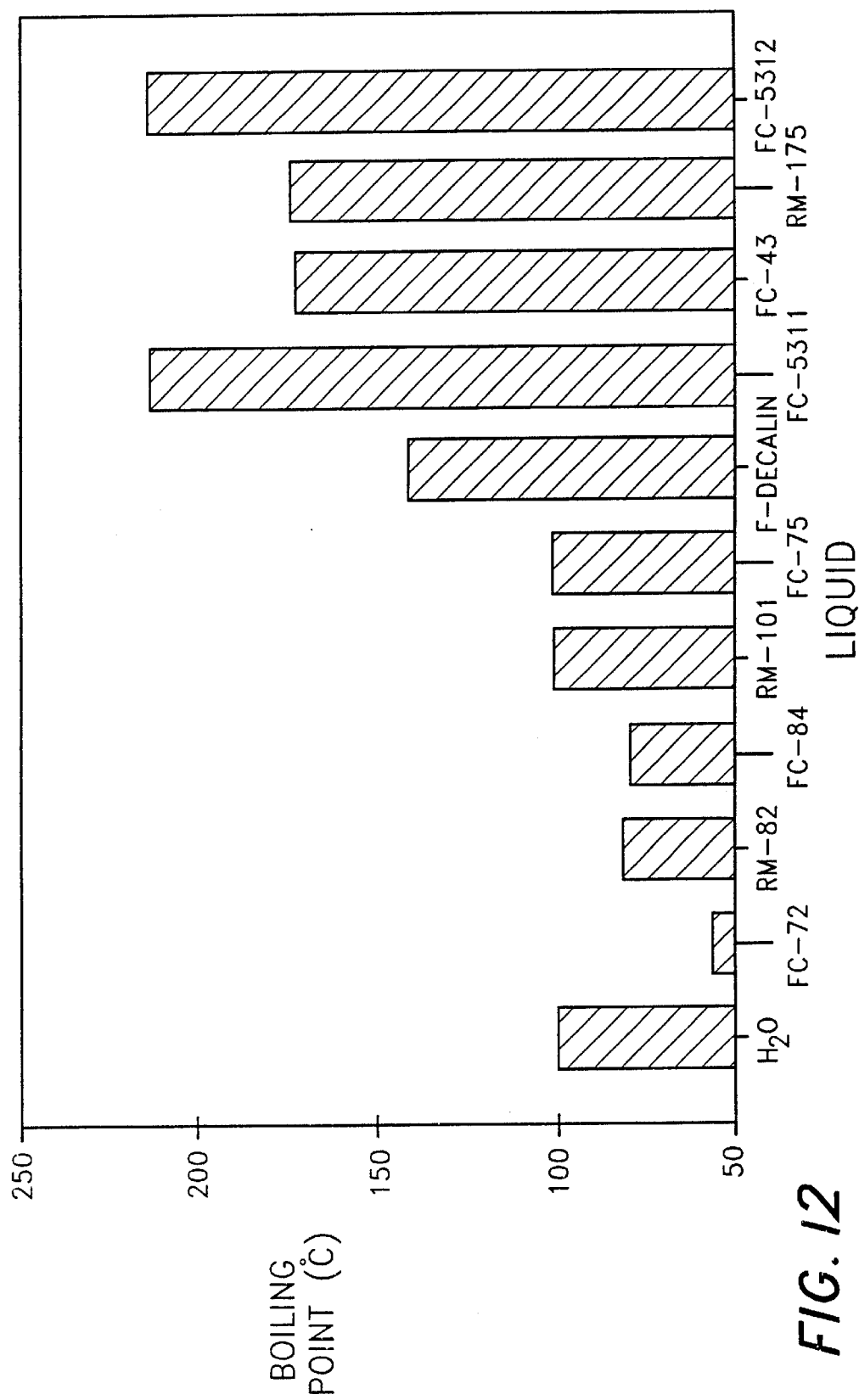
FIG. 12 is a graph indicating the boiling point (°C.) of representative perfluorocarbon liquids.

Thermodynamic properties: In ultrasound lung heating if will be undesirable to induce boiling in the coupling liquid since, at the very least, this will interrupt acoustic coupling. As shown in FIG. 12, this criterion renders FC-72 a very poor liquid selection, and RM-82 and FC-84 less than optimum as well. In this category, RM-101 and FC-75 roughly match the boiling points of tissues, so they are acceptable, though not as appealing as the higher molecular weight fluids.

Figure 13:
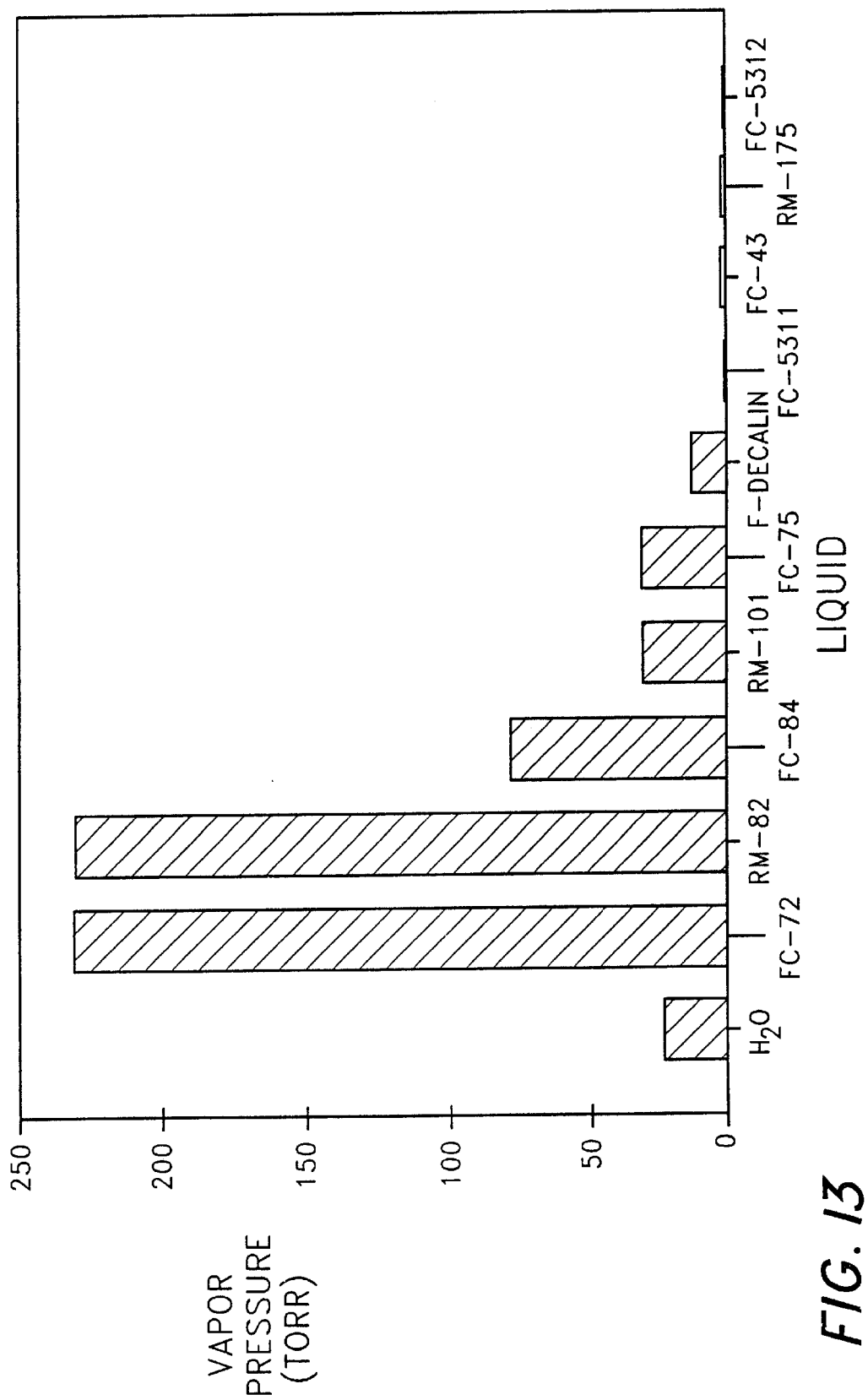
FIG. 13 is a graph indicating the vapor pressure (Torr) of representative perfluorocarbon liquids.

The efficient removal of perfluorocarbon liquid from the lung after liquid-filled lung hyperthermia treatments must be a leading consideration in designing the proposed therapies. The primary removal mechanisms for the bulk liquid will be first pumping or suctioning the fluid from the lung, permissibly followed by gravity-induced drainage (enhanced by the high densities of perfluorocarbons). The remainder of the fluid is then removed by evaporation. The facility with which a liquid evaporates is expressed by its vapor pressure; the higher the value, the more rapid the evaporation. As FIG. 13 demonstrates, perfluorocarbon liquids with molecular weights above F-Decalin are clearly unacceptable from this standpoint. It is not surprising that the most favorable liquids in this category (FC-72, RM-82, and FC-84) are the same ones that were undesirable from a boiling point perspective, since the physical phenomena are the same.

Heat transfer properties: The ability to convectively transfer heat to the lung will be governed by the "Prandtl number" of the fluid, which defines the ratio of viscous diffusivity to thermal diffusivity, i.e., the ratio (specific heat)x(viscosity)/thermal conductivity [64]. Because the specific heat for perfluorocarbon liquids is virtually constant (0.25 J/g-C) and since their thermal conductivities only vary by about 20% ($k_{ave}$=0.064 W/m-C), a Prandtl number comparison is dominated by differences in viscosity (see FIG. 9). Thus, from this standpoint, all fluids with molecular weights below F-Decalin are generally preferred and are approximately the same.

The ability to sustain constant temperatures in the lung is determined by the "thermal capacitance" of the fluid, or (density)×(specific heat). Again, because there is no variation in specific heat between the fluids, the more dense fluids will be those with higher thermal capacitances.

Example 3

Figure 14:
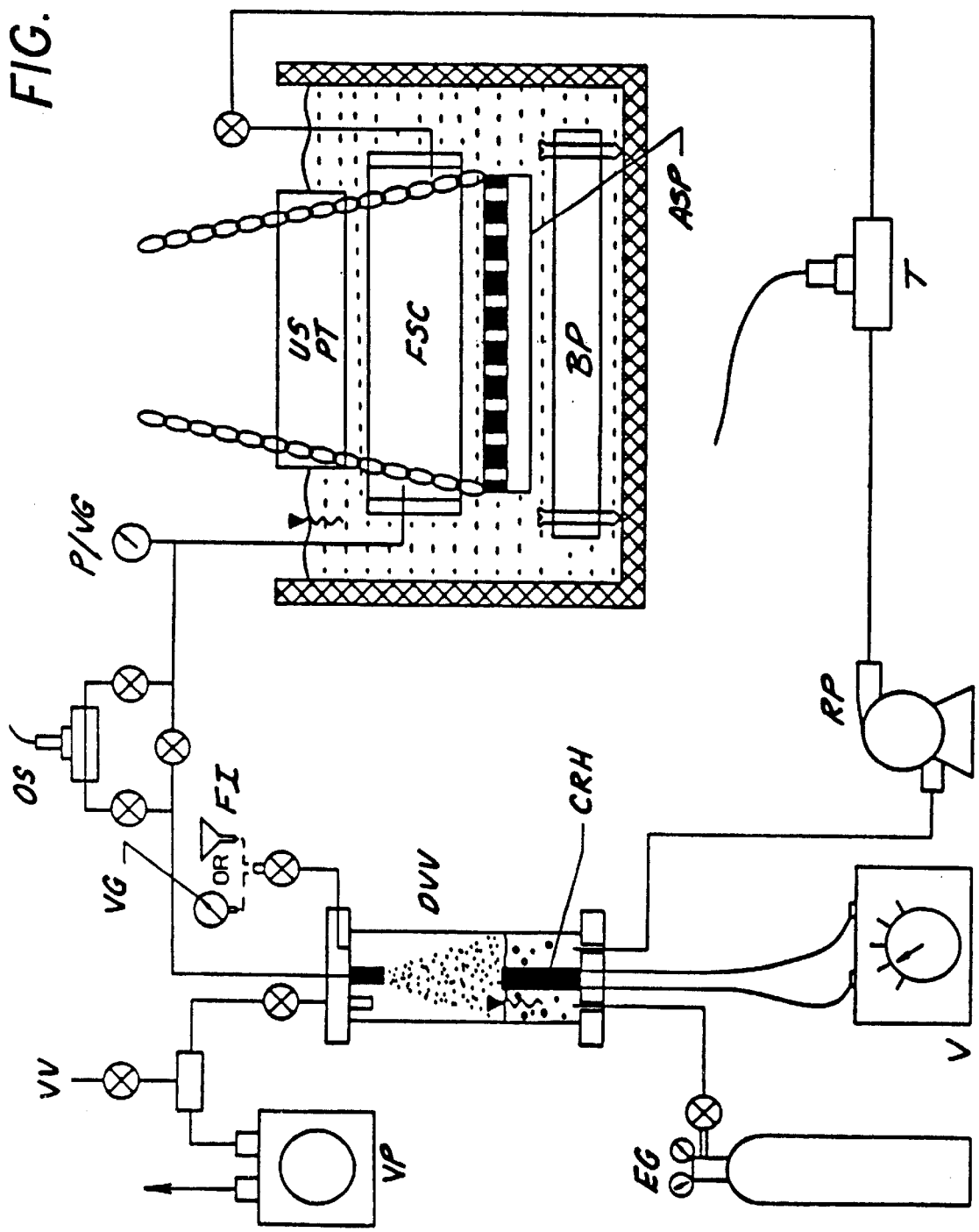
FIG. 14 is a schematic depiction of a representative acoustical test system.

Laboratory acoustic measurements: For the purpose of obtaining attenuation data over the range of physical parameters described, a special Perfluorocarbon Fluid Conditioning and Acoustic Measurement Flow System was constructed, as depicted schematically in FIG. 14. This system permitted low volumes of perfluorocarbon liquid (<1 liter) to be conditioned to any desired temperature and gas saturation level while exposing the liquid in a transparent fluid sample cell to ultrasound. The fluid sample cell featured thin membrane (1 mil Monokote) on the top and bottom surfaces, allowing virtually loss-free coupling of the sound to the cell via temperature-controlled degassed water. Sound attenuation was measured via the force balance method, which detects acoustic radiation pressure [65]. The sound traversed the sample cell and was then absorbed by an absorber plate suspended from a precision load cell. The acoustic path length through the perfluorocarbon liquid was 5.0 cm. An adjustable-height base plate below the absorber was adjusted to reduce oscillations in the absorber through the action of viscous fluid dampening. The radiation forces were recorded by a digital voltmeter connected to the load cell, with the voltage signals representing force automatically sent to a computer where the data was converted to acoustic power in Watts and stored for later analysis. To accommodate the need for frequencies below 1.0 MHz, both 250 and 500 KHz power transducers were constructed.

Cavitation is a complex function of temperature, fluid properties, fluid purity and cleanliness, ambient pressure, and gas content. For the purposes of this study, clean perfluorocarbon liquid was used and measured over a temperature range from 25° to 45° C. and at gas saturations from a completely degassed state to 100% saturation using air, O2, and blood gas (7%, O2, 7% CO2, balance N2). Cavitation thresholds were determined primarily by high-speed video camera recording, by still photography, and by visual inspection for bubble formation through the transparent sample cell walls. Sound speeds were measured by frequency-matched ultrasound transmitter/receiver transducer pairs separated by a known and fixed gap. A single-path, time-of-flight method of velocity measurement was employed using an oscilloscope.

Figure 15:
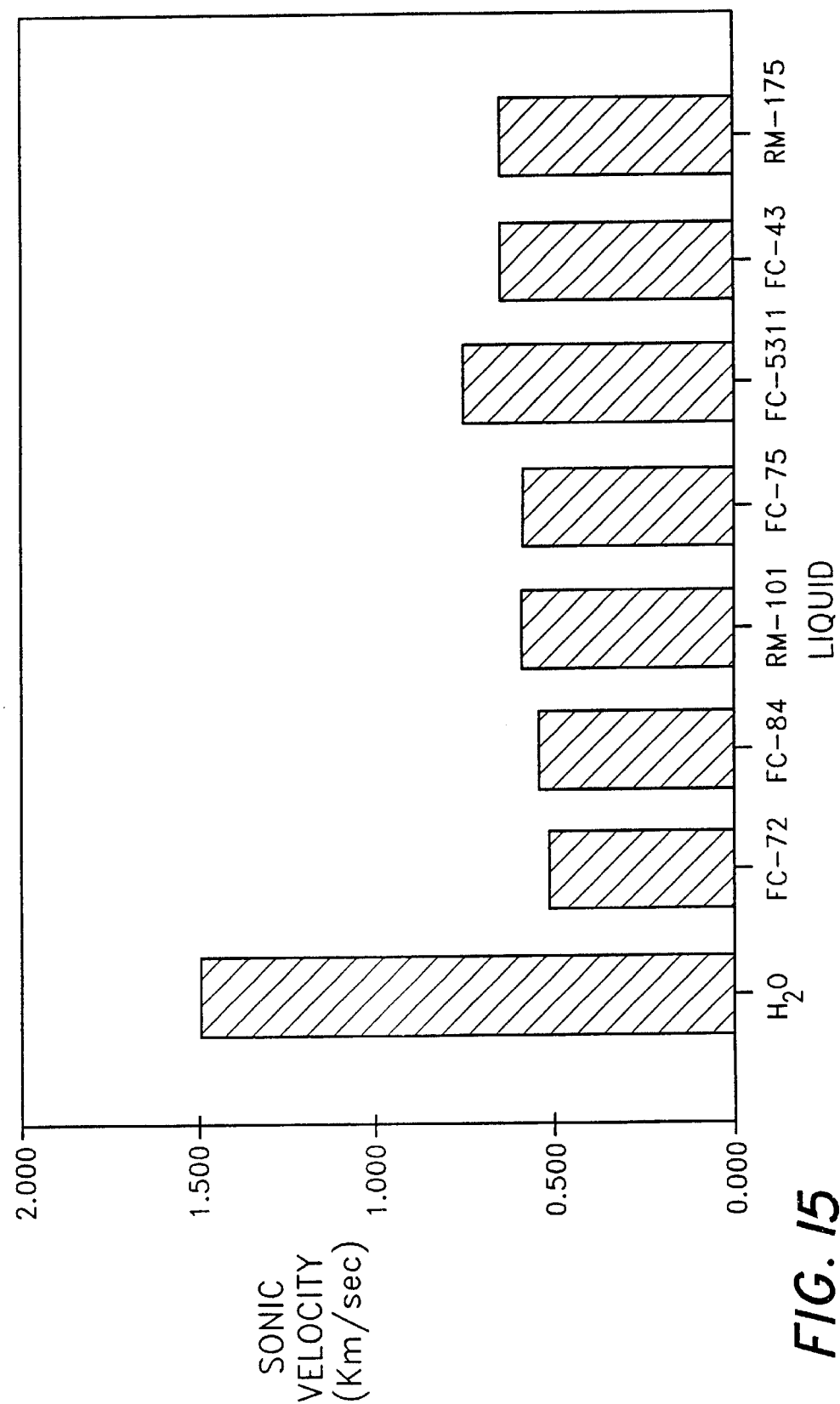
FIG. 15 is a graph indicating the velocity of sound (km/sec) in representative perfluorocarbon liquids.
Figure 16:
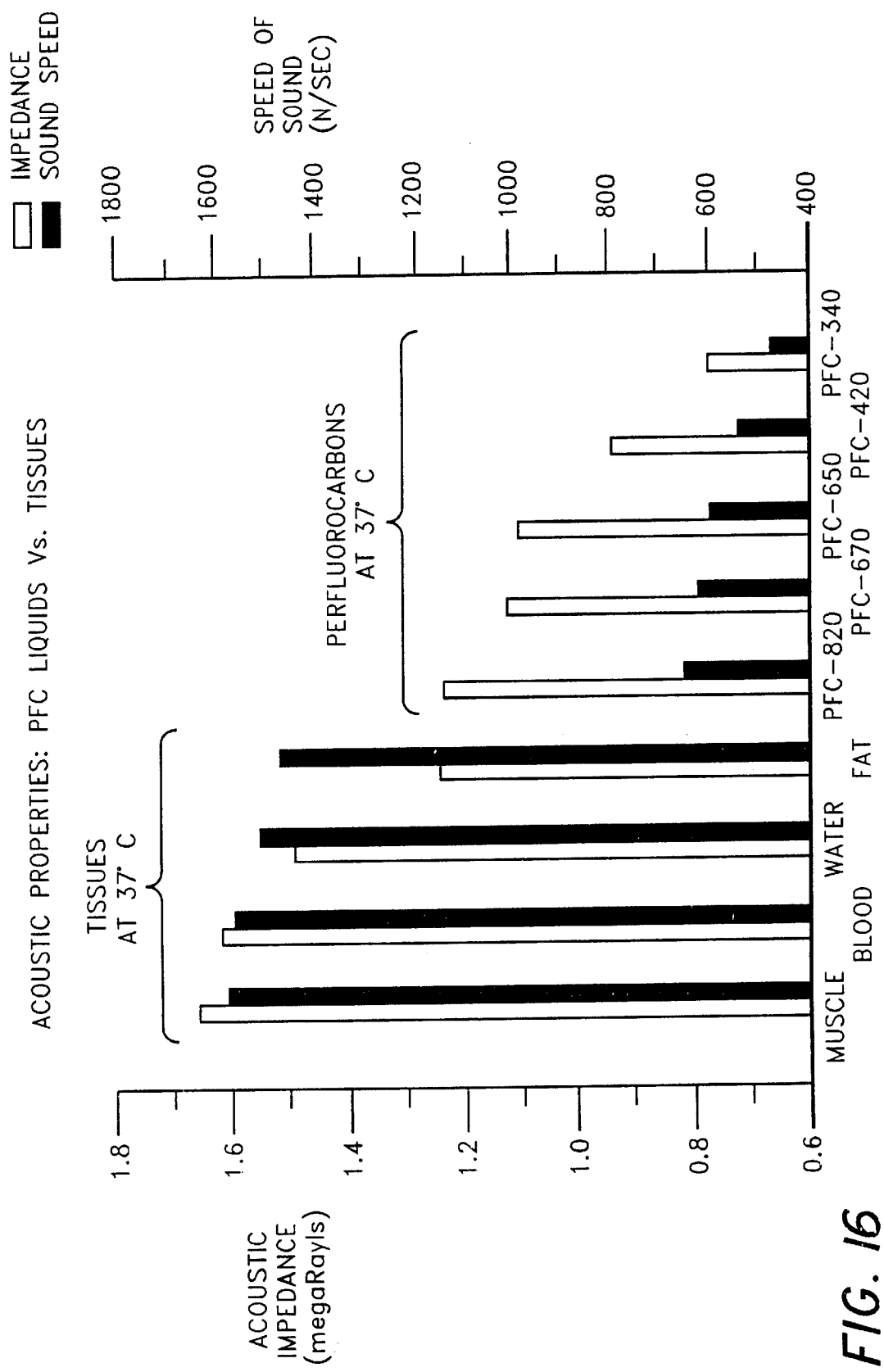
FIG. 16 is a graph indicating the acoustic impedance (MegaRayls) of selected tissues and representative perfluorocarbon liquids at 37° C.
Figure 17:
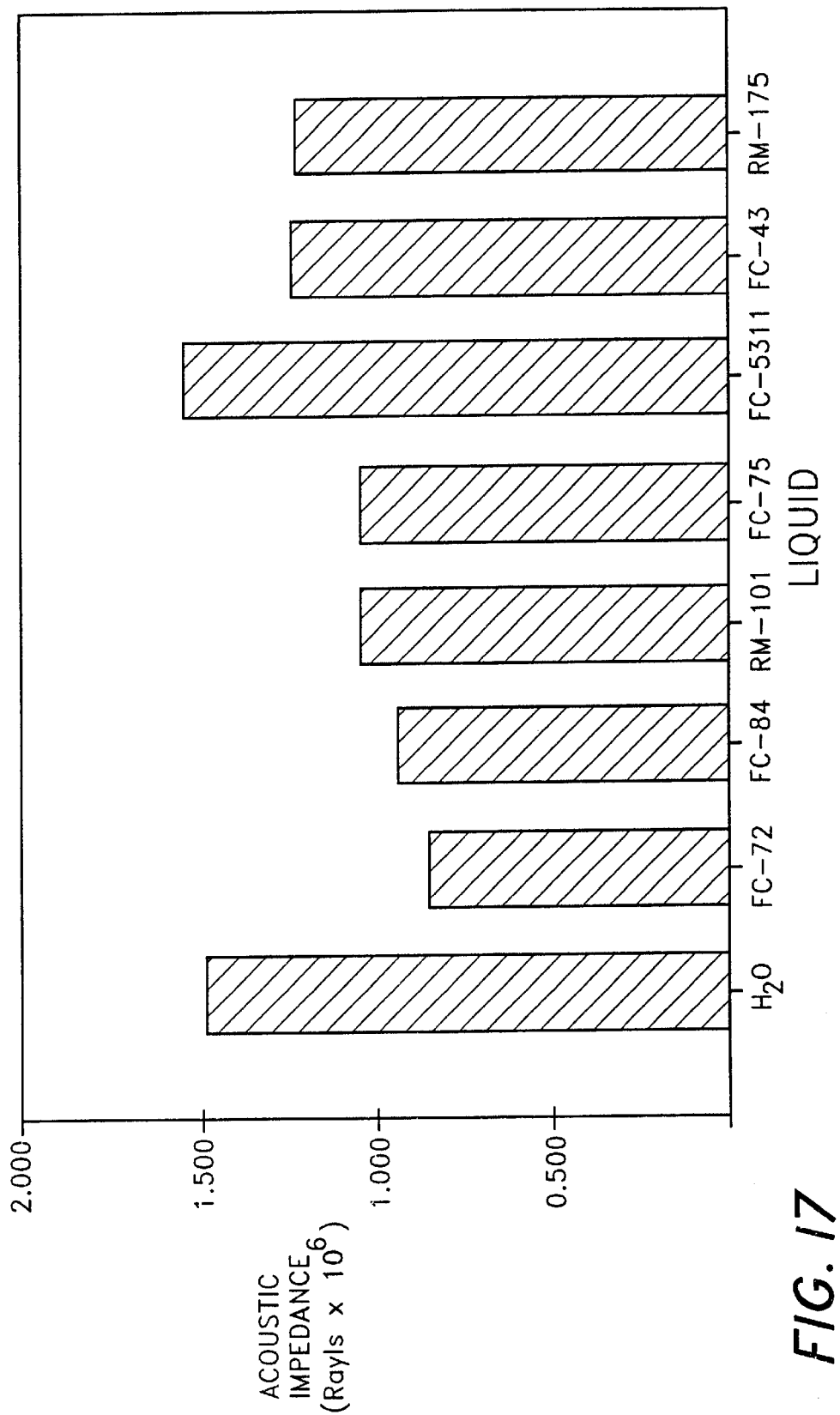
FIG. 17 is a graph indicating the acoustic impedance (Rayls×106) of representative perfluorocarbon liquids as compared with water.

Perfluorocarbon liquids have sound speeds which are among the lowest recorded for any liquids (FIG. 15). To obtain efficient coupling of the beam into the perfluorocarbon liquid from either water or tissue, the liquid's acoustic impedance, (density)×(sound speed), should approximately match that of water and tissue. Whereas the sound velocities are indeed very low in perfluorocarbon liquids, their higher densities favor a good acoustic impedance match, as shown in FIG. 16. FIG. 17 shows comparative values of perfluorocarbon acoustic impedances. Although FC-5311 shows an almost perfect match, this liquid is ill-suited for use in liquid-filled lung hyperthermic treatments on the basis of the physical properties discussed above. The remaining acoustic matching values, while not ideal, can provide good coupling of sound between water and tissue. For example, the transmission loss of sound passing from water into FC-75 is only slightly over 3 percent.

Example 4
Acoustic Properties of Perfluorocarbon Liquids

Acoustic measurement materials and methods: Ultrasound transmission is primarily governed by attenuation in the perfluorocarbon liquids and, at relatively higher intensities, cavitation (i.e., creation of small bubbles by gases liberated out of solution). Lab measurements of sound speed, impedance, attenuation, and cavitation were done in several perfluorocarbon fluids over a temperature range from 25° to 45° C. and at various gas saturations representative of conditions anticipated in liquid-filled lung hyperthermic treatments in a special Perfluorocarbon Fluid Conditioning and Acoustic Measurement Flow System (depicted schematically in FIG. 18).

Blood perfusion in liquid-filled lungs is much lower than under normal physiological conditions, particularly when the lung tissue being treated is not simultaneously ventilated. In addition to enhancing the localization of the treatment, as discussed above, by virtue of reducing blood perfusion dissipation of thermal energy, the ultrasound power required for lung hyperthermia is surprisingly lower than might be appropriate for other vascularized tissue, e.g., muscle. The acoustic intensities employed for the evaluation of perfluorocarbon acoustic properties ranged from 0–3.5 W/cm$^2$ and are expected to fully encompass the range appropriate for lung heating. Somewhat higher output powers were used in the cavitation evaluations. In addition, although properties were measured at frequencies of 0.25, 0.50, 0.90, 1.0, 1.1, and 2.25 MHz, only the range from 0.25 to 1.1 MHz was studied in detail due to the high attenuation associated with 2.25 MHz sound. The following observations were made.

Acoustic impedance: Perfluorocarbon liquids have sound speeds which are among the lowest recorded for any liquids. To obtain efficient coupling of the beam into the perfluorocarbon liquid from either water (or tissue), the liquid acoustic impedance, (density)×(sound speed), should approximately match that of water and tissue. Whereas the sound velocities are indeed very low in perfluorocarbon liquids, their high densities favor acoustic impedance matching, as shown in FIG. 16 (perfluorocarbons listed according to molecular weight). For example, the transmission loss of sound passing from water to FC-75 is only slightly over 3 percent.

Figure 19:
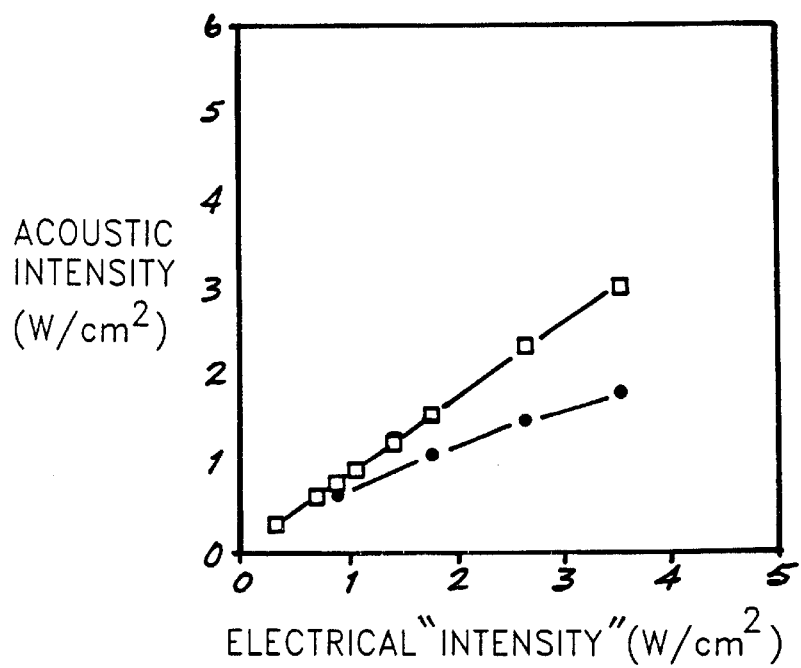
FIG. 19 is a graph depicting acoustic losses in perfluorocarbon liquids by plotting the relationship between perfluorocarbon acoustic intensity (W/cm$^2$) and electrical intensity (W/cm$^2$) at 1.0 MHz and 25° C.
Figure 20:
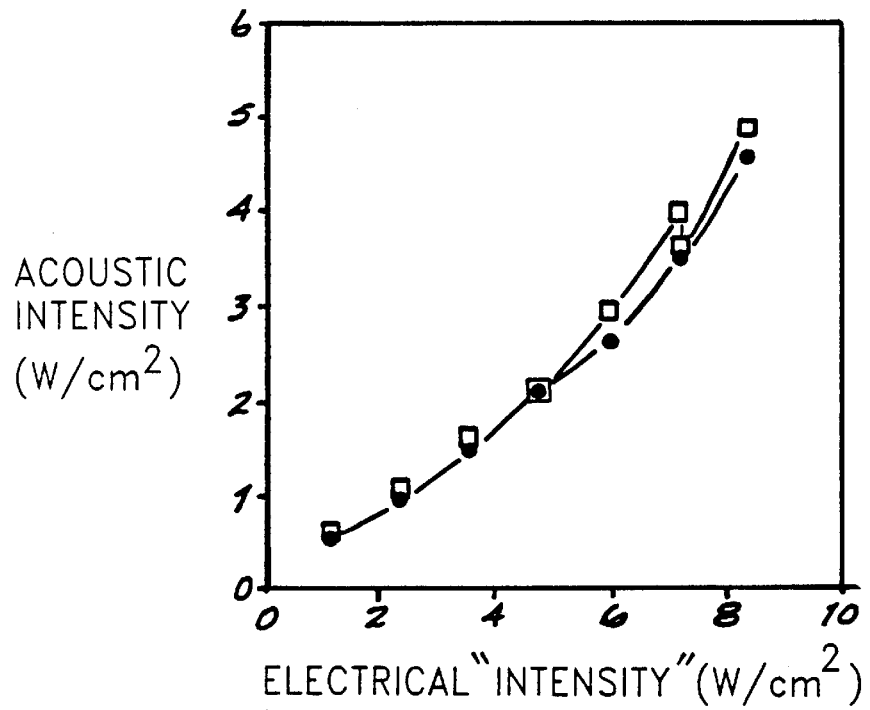
FIG. 20 is a graph depicting acoustic losses in perfluorocarbon liquids by plotting the relationship between perfluorocarbon acoustic intensity (W/cm$^2$) and electrical intensity (W/cm$^2$) at 0.5 MHz and 25° C.
Figure 21:
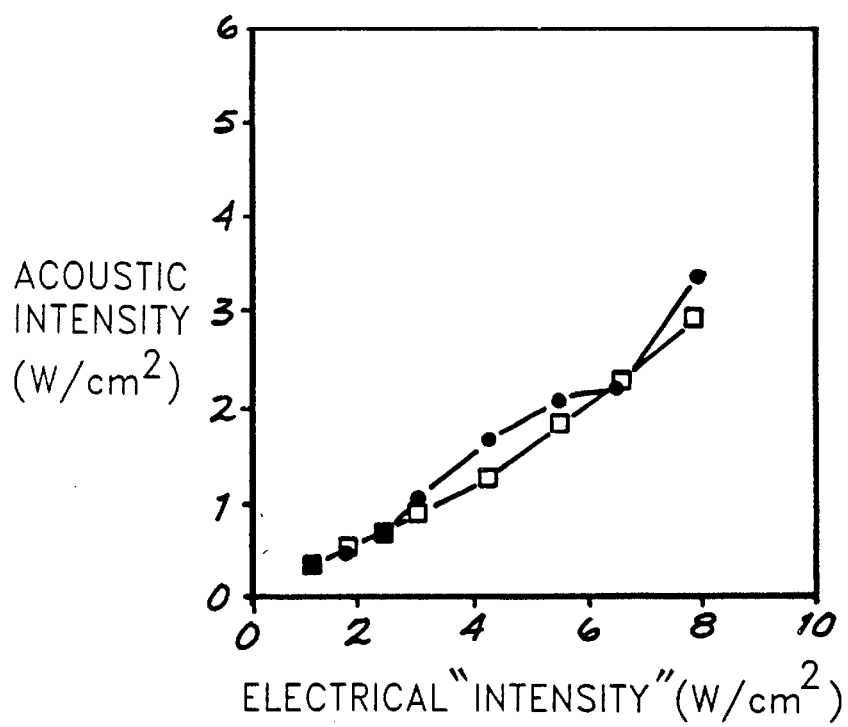
FIG. 21 is a graph depicting acoustic losses in perfluorocarbon liquids by plotting the relationship between perfluorocarbon acoustic intensity (W/cm$^2$) and electric intensity (W/cm$^2$) at 0.25 MHz and 25° C.
Figure 22:
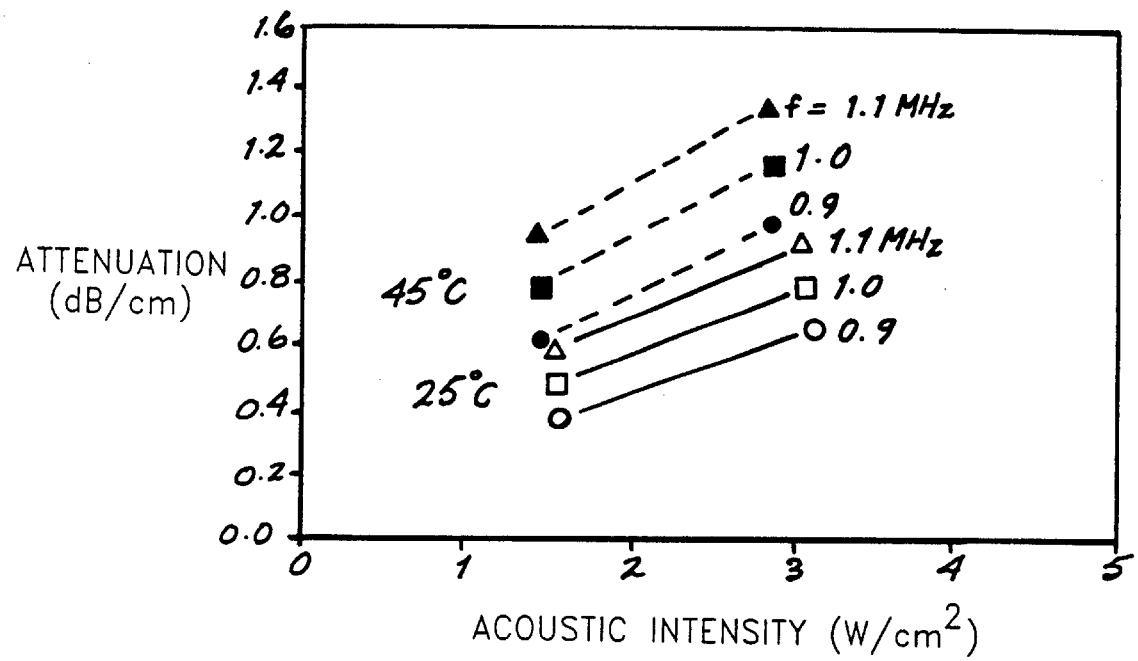
FIG. 22 is a graph indicating the relationship between perfluorocarbon attenuation (dB/cm) and acoustic intensity (W/cm$^2$) as functions of temperature (25° or 45° C.) and frequency (MHz)
Figure 23:
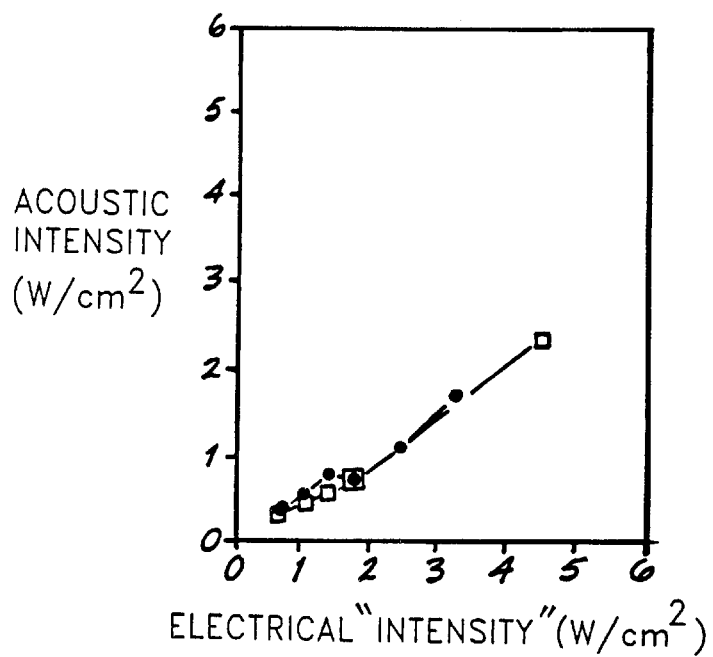
FIG. 23 is a graph indicating the relationship between acoustic intensity (W/cm$^2$) and electrical intensity (W/cm$^2$) for FC-75 at 0.25 MHz and 45° C.
Figure 24:
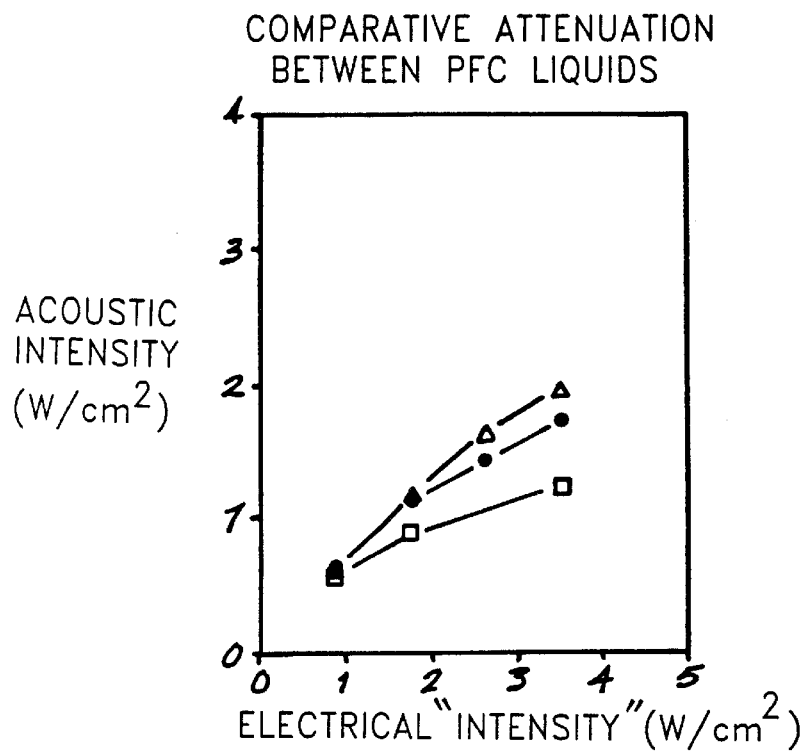
FIG. 24 is a graph of acoustic intensity (W/cm$^2$ versus electrical intensity (W/cm$^2$), indicating the attenuation range of various perfluorocarbons at 1.0 MHz and 25° C.

Acoustic attenuation: The most surprising acoustic characteristic of perfluorocarbon liquids was found to be their low threshold for exhibiting nonlinear behavior. FIG. 19 shows the attenuation behavior of FC-75 by comparing the acoustic power transmitted through 5 cm of degassed water (virtually loss-free) versus that through FC-75 at 1.0 MHz. It can be seen that the attenuation gradually increases with power (electrical power is normalized by the transducer face area and expressed as Electrical "Intensity"), even over the moderate power levels required for lung heating. The liquid attenuation is, however, extremely sensitive to frequency. As shown in FIGS. 20 and 21, the attenuation and the degree of non-linearity fall dramatically at lower frequencies, showing virtually loss-free behavior at 250 and 500 KHz (within the limits of accuracy of the measurement method). The attenuation in perfluorocarbon liquids also increases as the fluids are heated, as depicted in FIG. 22. This is an interesting nonlinear aspect as well, for attenuation in water and most fluids decrease with temperature, due to the reduction of viscosity. Although perfluorocarbon attenuation increases with temperature, the use of low frequencies can compensate, resulting in very low losses, as the 250 KHz, T=45° C. data of FIG. 23 show. FIG. 24 compares the attenuation in three perfluorocarbon liquids representing a significant range of molecular weights.

Cavitation: While the bio-effects of acoustic cavitation are apparently tolerated in some therapeutic applications [55], in principle it will be better to avoid it in the liquid-filled lung. The data obtained in these experiments have shown that cavitation is likely to occur at ultrasound intensity levels only if the perfluorocarbon liquid is at or very near its saturation point in terms of dissolved gases (e.g., O2 or blood gases). Thus, it will not be advisable to support respiration in the lung with 100% O2 saturated liquids while using ultrasound heating. However, this does not preclude the use of incompletely gassed liquids (e.g., 75% saturation) for use in simultaneous ventilation with ultrasound hyperthermia.

Figure 25:
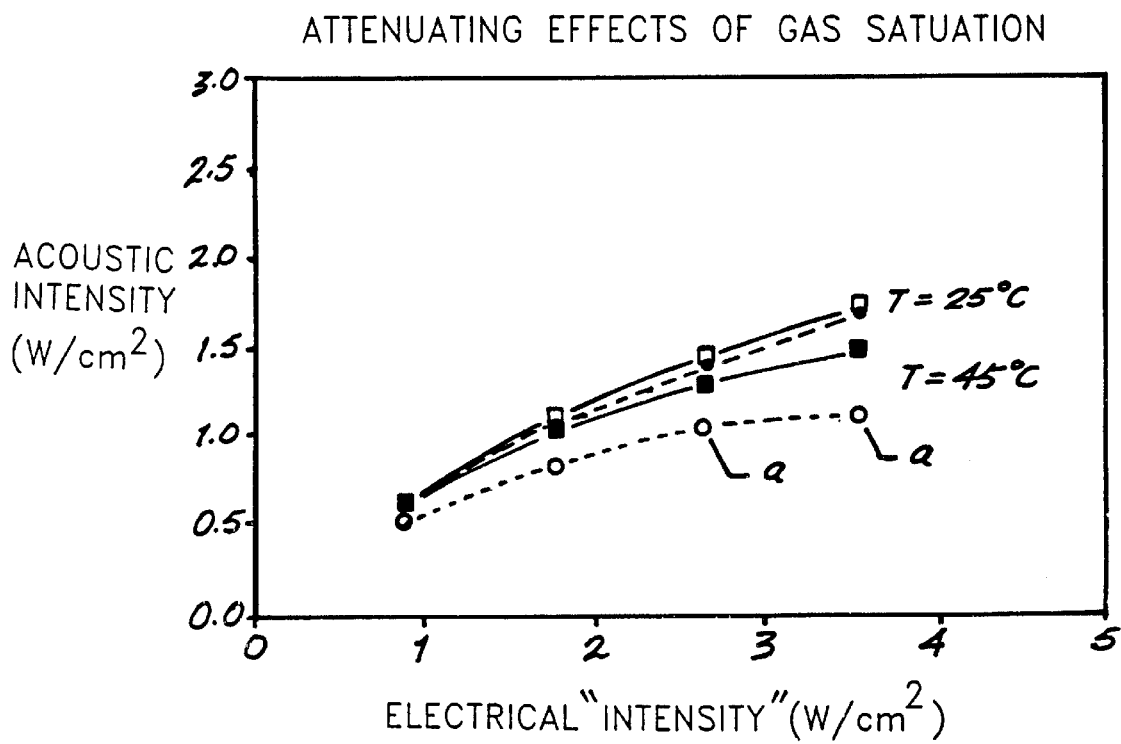
FIG. 25 is a graph of acoustic intensity (W/cm$^2$) versus electrical intensity (W/cm$^2$), indicating the attenuating effects of gas saturation in perfluorocarbon FC-75 at 1.0 MHz and 25° or 45° C.

Also, it should be emphasized that simultaneous 100% O2 liquid ventilation support while convectively heating the lung is feasible. FIG. 25 shows the power dissipation which occurs from cavitation in 100% saturated FC-75 over the hyperthermic temperature range. This data also indicates that no cavitation occurs in degassed liquids. Some variation of the threshold for cavitation in gas-saturated liquids was found as a function of frequency as well as of temperature.

Figure 18:
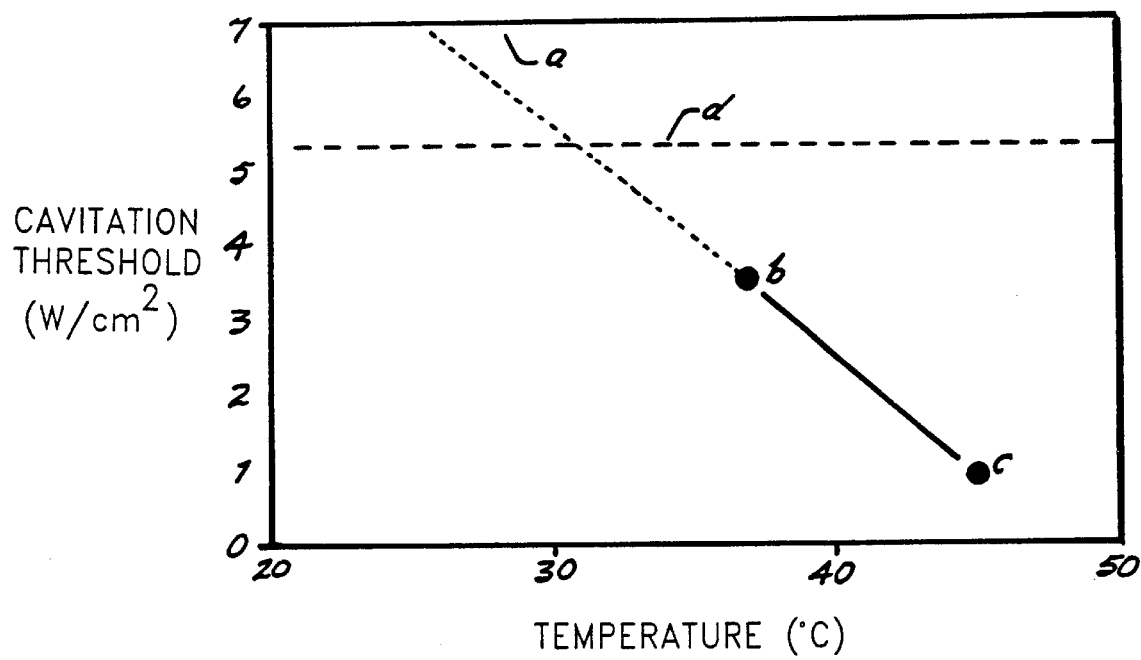
FIG. 18 is a graph indicating the relationship between perfluorocarbon cavitation threshold (W/cm) and temperature (°C.) as a function of gas saturation.

It is important to stress that even slight degassing seems effective in suppressing cavitation at these intensities. This is probably due to the tremendous perfluorocarbon affinity for gases. Perfluorocarbons appear less prone to cavitation at equivalent saturations and intensities than water. The perfluorocarbon capacity to dissolve gases is so high, in fact, it is difficult to cavitate liquids at the recommended ultrasound powers even a few percent below saturation, as seen in FIG. 18 (where gas saturation is changed in small increments by changing liquid temperature). Because of both decreased lung perfusion during liquid-lung procedures and the large "gas sink" characteristics of perfluorocarbon liquids, it is plausible that the pulmonary circulation would take several minutes to saturate degassed perfluorocarbon liquids introduced into the lung, particularly considering that the partial pressure of $H_2O$ vapor may preclude sufficient dissolved gas saturation conditions from occurring at all. Completely degassed liquids were used in the animal experiments (described below). The liquids were cycled into and out of the lung (several minutes apart) to maintain low liquid gas levels.

Summary

On the basis of the foregoing experimental observations, the fluorocarbon liquids FC-75 (a mixture of perfluorobutyltetrahydrofuran and perfluoropropyltetrahydropyran; 3M Company, Minneapolis, Minn.) and RM-101 (a mixture of Furan,2,2,3,3,4,4,5 heptafluorotetrahydro-5-(nonafluorobutyl) and 2H-Pyran,2,2,3,3,4,4,5,5,6-nonafluorotetrahydro-6-(nonafluorodecafluoro); MDI Corp., Bridgeport, Conn.) were found equally suitable as ultrasound transmission and heat transfer fluids in the lung. Reinforcing the selection of these fluids (which, in purified form, should be substantially free of hydrogen) is the fact that both have been used in animal liquid ventilation research and have excellent records of biocompatibility [3]. FC-75 and RM-101 are thus considered representative of the class of perfluorocarbon liquids, most suitable for liquid-filled lung convection and ultrasound procedures, having the most preferred physical, thermal, and acoustical parameters. Since FC-75 is representative of this class, the presentation of its properties will be emphasized from this point on.

EXAMPLE 5

Acoustic Properties of Perfluorocarbon-Filled Lungs

Animal Model/Study Design

Due to their size and structure, adult sheep lungs are good pulmonary models. In the following animal experiments, five adult sheet were used in acute in vivo and in vitro studies. A narrow band, 1.0-MHz, 6-cm diameter piezo-ceramic disk transducer with an integral temperature controlled coolant/coupling liquid was utilized for these studies. Both thermal techniques (measuring specific absorption rates (SAR) of power) and acoustic methods (measuring acoustic pressures and intensities) were employed. The animal preparation and experimental methods employed for the in vivo studies are described in detail below.

Animal Preparation

Following the methods normally used in ongoing liquid ventilation research, the animals were all initially given pentobarbital sodium (20 mg/kg) to induce deep sedation. After a local infiltration of 1% lidocaine in the neck, the right carotid artery and right jugular vein were cannulated. A tracheotomy was performed for the placement of either an indotracheal tube or a liquid infusion catheter (the catheter shown in FIG. 1 could be used for this purpose). To maintain biological stability, the sheep's untreated lungs are ventilated on a mechanical ventilator at a volume of 500 ml, at a frequency of approximately 15–20 breaths per minute, under skeletal muscle paralysis (pancuronium bromide; initial bolus of 0.1 mg/kg, followed by 0.1 mg/kg/hr). In addition, steady state maintenance of the animals included an intravenous crystalloid infusion (10% dextrose with 10 mEq sodium bicarbonate and 1 mg sodium pentobarbital/100 ml fluid) administered at a rate of 3 ml/kg/hr. Physiological monitoring was done via arterial blood gas tensions, pH, heart rate, and blood pressure measurements. Additional surgical procedures during in vivo experiments included double or triple rib resections, to expose an acoustic window for the ultrasound applicator. Also, small needle thermometry probes were inserted in deep muscle and in the isolated region of the lungs (described below). All animals were euthanized with magnesium chloride.

Liquid-Filled Lung Procedures

To quantify acoustic properties in perfluorocarbon-filled lungs in vitro, a series of experiments were performed on isolated adult sheep lungs. There is a striking visual difference between a normal air-filled lung and one which is filled with fluorocarbon liquid. The glistening dark red color characteristic of the successfully filled "liquid lung" was one measure of a lung reaching complete filling. In addition, measurements of acoustic propagation were also used to confirm the degree of filling. It was found, both in the in vitro and in vivo cases, that the lung filling process could be accomplished in about one-quarter of the time previously required for perfluorocarbons if the liquid were completely degassed prior to the initial infusion (only 1–3 minutes). The enhanced filling process was due to the perfluorocarbons' ability to dissolve great quantities of gas, rather than simply depend on displacing the trapped alveolar air. It was found that saline filling required much more time than for the fluorocarbons using partially degassed liquids.

In vitro Ultrasound Experimental Materials and Methods

In vitro ultrasound characterizations were performed with an applicator consisting of a narrow band 1.0-MHz, 6-cm piezo-ceramic disk transducer with temperature controlled coolant/coupling liquid continuously surrounding it. The system was capable of delivering 150 Watts of acoustic power, though these power levels were in excess of that required for fast warmup and certainly much more than was required for stable steady state lung hyperthermia.

The isolated lungs were instrumented either with thermocouple probes (29 gauge) or with ultrasound hydrophones for thermal or acoustic determinations of attenuation, respectively. Acoustic gel was used to insure good coupling into the tissue. The thermal technique used was that of determining the Specific Absorption Rate (SAR) from the initial rate of temperature rise [66] at different depths in the lung. Ratios of SAR at the various depths yielded attenuation. The hydrophone measurements recorded dynamic pressure variations directly which were displayed on an oscilloscope. Squaring of the pressure data resulted in data proportional to intensity, which could then be translated to attenuation values for known acoustic path lengths.

In Vivo Liquid-Lung Ultrasound Hyperthermia Materials and Methods

To provide efficient filling of the lung lobe, completely degassed FC-75 was introduced through a conventional clinical bifurcated bronchial catheter that permitted infusion of the selected lung lobe while sustaining gas ventilation in the remainder of the lung. The catheter was placed without benefit of a bronchoscope, so the correct placement had to be determined by verification of lung inflation motions in the desired lung segments. The perfluorocarbon liquid was introduced at room temperature and only infrequently circulated in and out. In most cases the cranial segment of the right apical lobe was chosen for selective heating, both in the ultrasound and the convective hyperthermia experiments.

These segments had inflated volumes of approximately 250–300 ml. An "acoustic window" to the lung segment was obtained by resection of portions of three ribs essentially analogous to an intraoperative hyperthermia treatment. The treated lung segment was partially exteriorized through the "window" to enable invasive thermometry of the treated lung at different depths. The sound was propagated directly through coupling water and membrane into the lung. In most cases, the lung surface was cooled with 37° C. coupling water.

In addition to heating data, in vivo acoustic measurements were also performed via the hydrophone method previously described. Continuous recording of relevant physiological parameters were performed throughout the experiments. These measurements included systolic and diastolic blood pressure (reduced to Mean Arterial Pressure), core temperature, heart rate, and respiration rate. Gas ventilation was maintained by a mechanical respirator. Cardiopulmonary stability was confirmed throughout the treatments by taking periodic blood samples for arterial pH, $pO_2$, and $pCO_2$.

In Vitro Ultrasound Results

Figure 26:
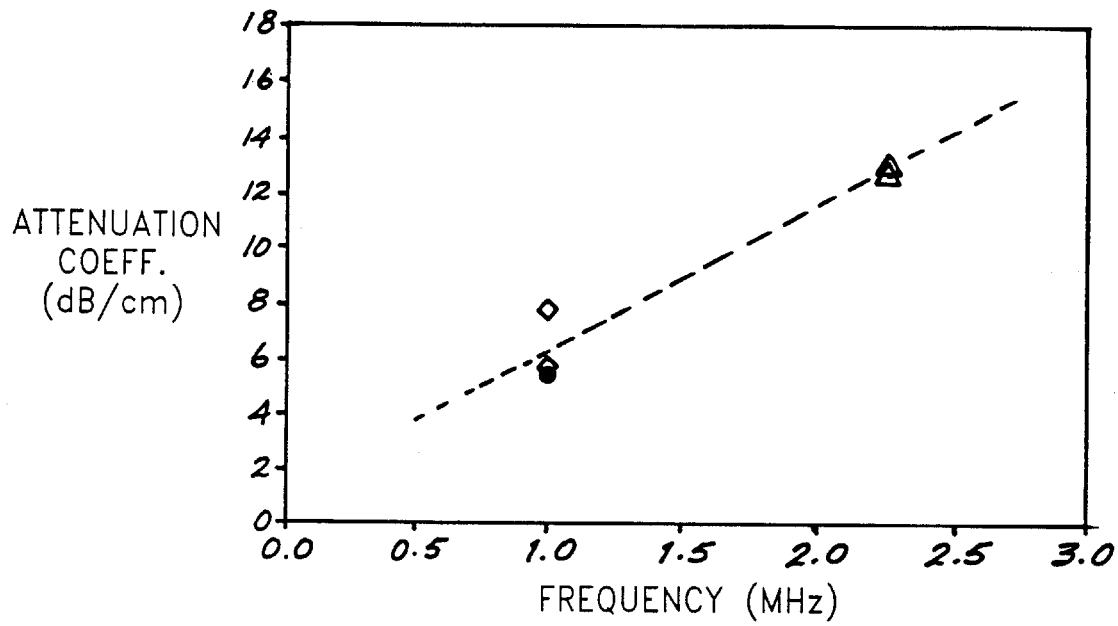
FIG. 26 is a graph of attenuation coefficient (dB/cm) versus frequency (MHz), showing in vitro perfluorocarbon-filled lung attenuation at various frequencies (MHz)

FIG. 26 presents typical in vitro attenuation values for isolated lung of an adult sheep. The attenuation shows a significant increase with increasing frequency. Note also that the attenuation levels are higher in the liquid-filled lung than for the pure liquid. It is postulated that this augmented attenuation is mostly attributable to scattering from the refraction effects of the sound speed mismatch between the parenchymal tissue and the liquid (increased scattering is supported by the ultrasound imaging results as well). Because scattering increases the effective acoustic path length, a wave traverses and spreads the beam slightly, the near loss-free propagation for lower frequencies (e.g., 250 and 500 KHz; FIGS. 20, 21, and 23) in perfluorocarbon liquids is no doubt preferred to frequencies above 1 MHz for deeper hyperthermia. Lower frequency ultrasound should also exhibit significantly reduced scattering since the wavelength increases substantially (e.g., to 3–6 mm) in relation to the main scattering structures (i.e., bronchioles, diameters <1 mm [56]).

Figure 27:
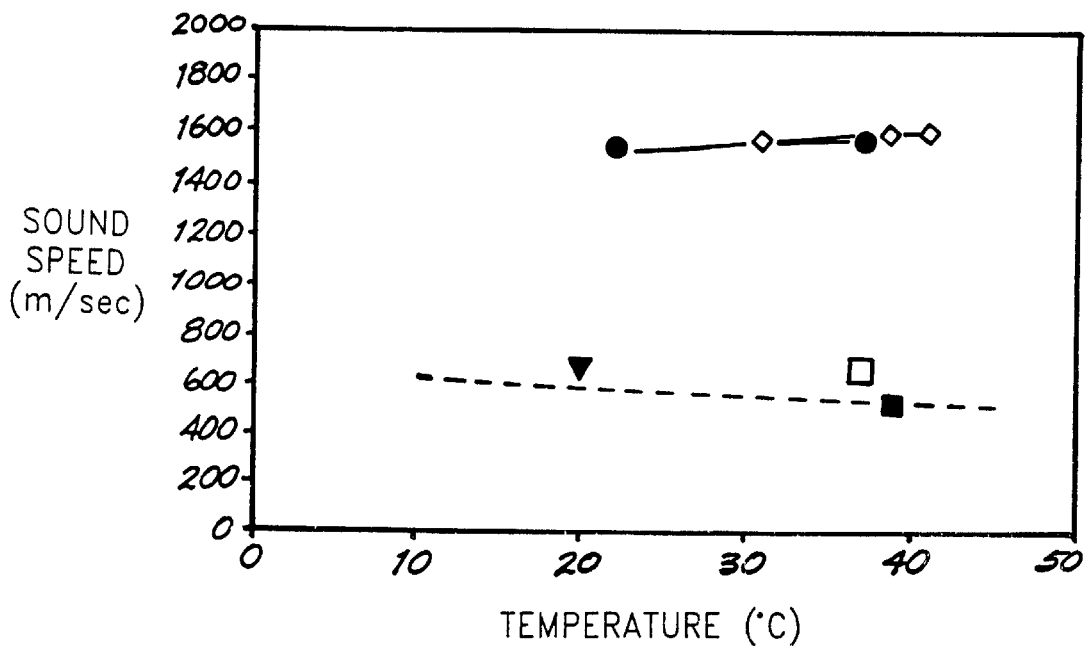
FIG. 27 is a graph of sound speed (m/sec) versus temperature (°C.), indicating the predominance of perfluorocarbon FC-75 in establishing the sound speed in liquid-filled lungs; these properties are compared with blood and muscle.

FIG. 27 demonstrates that the liquid-filled lung acoustic properties are dominated by the presence of the liquid (this likely also holds true for the thermal properties). This data shows that the effective sound speeds measured (both in vivo and in vitro) are close to those of the pure liquid (dashed line). Note that connective tissue sound speeds are usually higher than those of blood and muscle.

Example 6

In Vivo Acoustic Lung Hyperthermia

Figure 28:
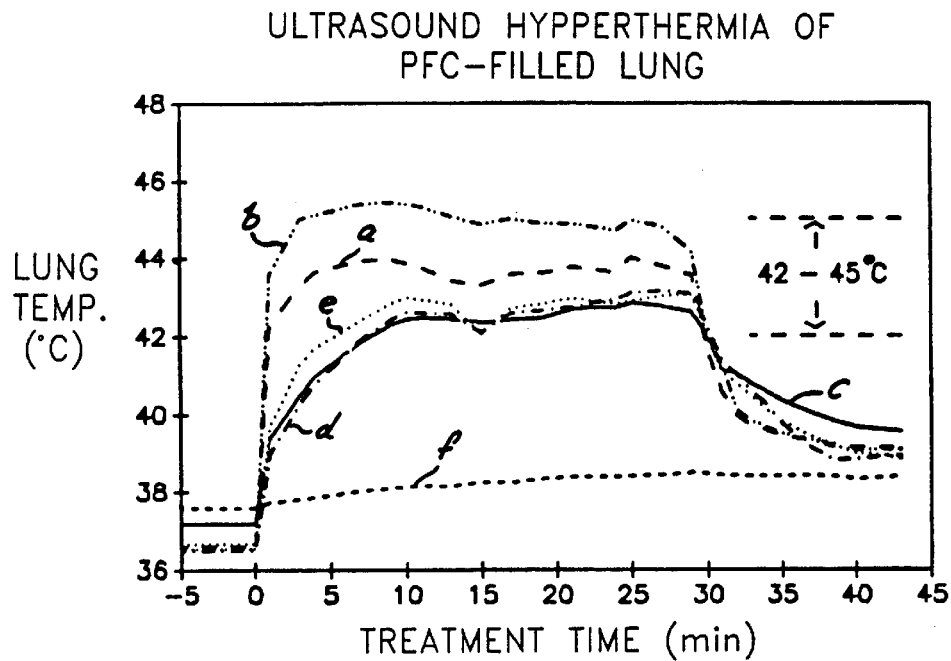
FIG. 28 is a graph of lung temperature (°C.) versus treatment time (min), demonstrating ultrasound hyperthermia of perfluorocarbon-filled pulmonary air passages.

Employing the methods and protocols described in Example 5, sustained hyperthermia (42–45° C. to about 4 cm depth for 30 minutes) was successfully accomplished in the two animals used for the tests. The temperature vs. depth histories which resulted are represented by FIG. 28, which depicts the experiment employing the greatest number of temperature probes. In this case probes were located in the interstitial tissue along the beam central axis at depths of 0.5, 1.0, and 2.0 cm, and also at 3.0 cm but slightly off axis. In addition, an on-axis probe was placed on the distal surface of the lung segment (approximately 6 cm from the treatment surface) between the lung surface and a rubber mat (which also acted as an acoustic absorber). As shown, lung temperatures exceeded 43° C. to approximately 3 cm depth, with acoustic penetration through the lung segment indicated by the high temperatures on the distal surface (effectively 6 cm deep). The close tracking of the 2 and 3 cm depth temperatures (again, not in line with each other) may have been due to refractive effects or differences in local perfusion. The lower temperature at the 0.5 cm site is due to the conductive cooling of the coupling water (at 37° C.). The "thoracic cavity" core temperature probe was located near the treated segment in the cavity. The steady state power requirements in this case ranged between 12 to 15 Watts, again indicative of low pulmonary perfusions due to the liquid presence.

Perfusion Response of the Liquid-Filled Lung

The ultrasound power levels required for steady state hyperthermia were unexpectedly low due to low blood flow levels in the heated lung. An analysis of the physiological mechanisms involved, however, indicates that the perfusion is suppressed due to the combined effects of: 1) increased pulmonary vascular resistance due to the presence of the liquid compressing alveolar capillaries, 2) the shunting of the pulmonary circulation to other areas of the lung from locally low $pO_2$ (here from degassed liquids), and 3) to shunting from a low pH buildup in the lobe [29, 30, 31].

Example 7

In Vivo Convective Lung Hyperthermia

Convection Hyperthermia Materials and Methods

Figure 29:
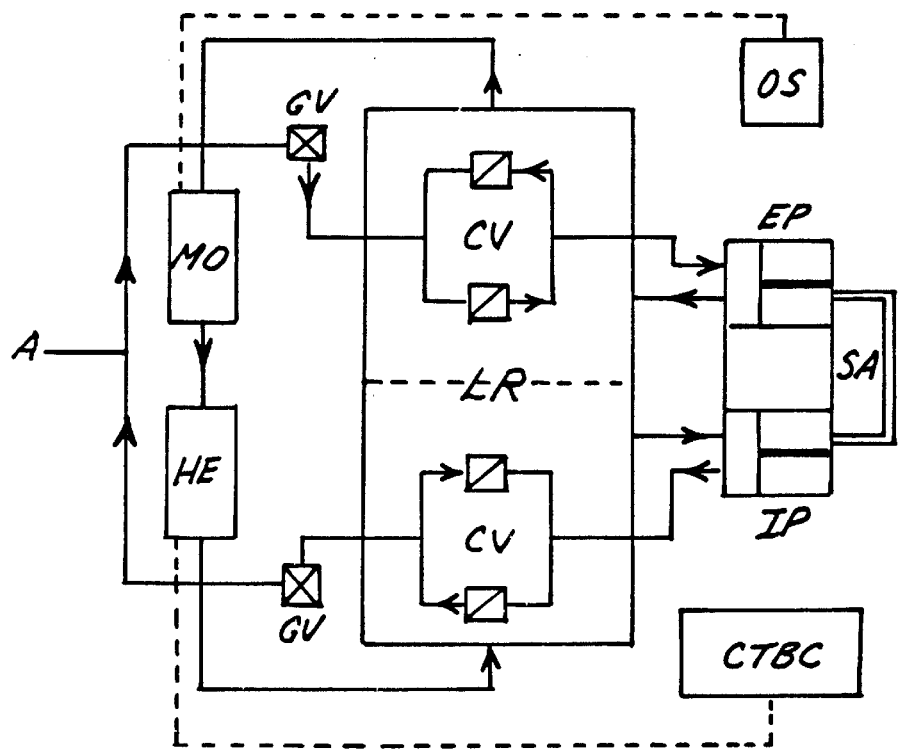
FIG. 29 is a schematic diagram of the Large Animal Liquid Ventilation System at Temple University.

Using the large animal liquid ventilation (LALV) system of Temple University (FIG. 29), heated, temperature-controlled FC-75 could be circulated in and out of lung lobes and segments isolated via the bifurcated bronchial catheter method as described above. The animal preparation was essentially the same as for the ultrasound experiments. In this way convective lung hyperthermia was successfully administered to the cranial segment of the right apical lung lobe. To instrument the lung so that temperature probes could be easily placed at known depths, the lung segment was partially exteriorized through a "window" created in the same manner as was done for the ultrasound experiments.

Figure 30:
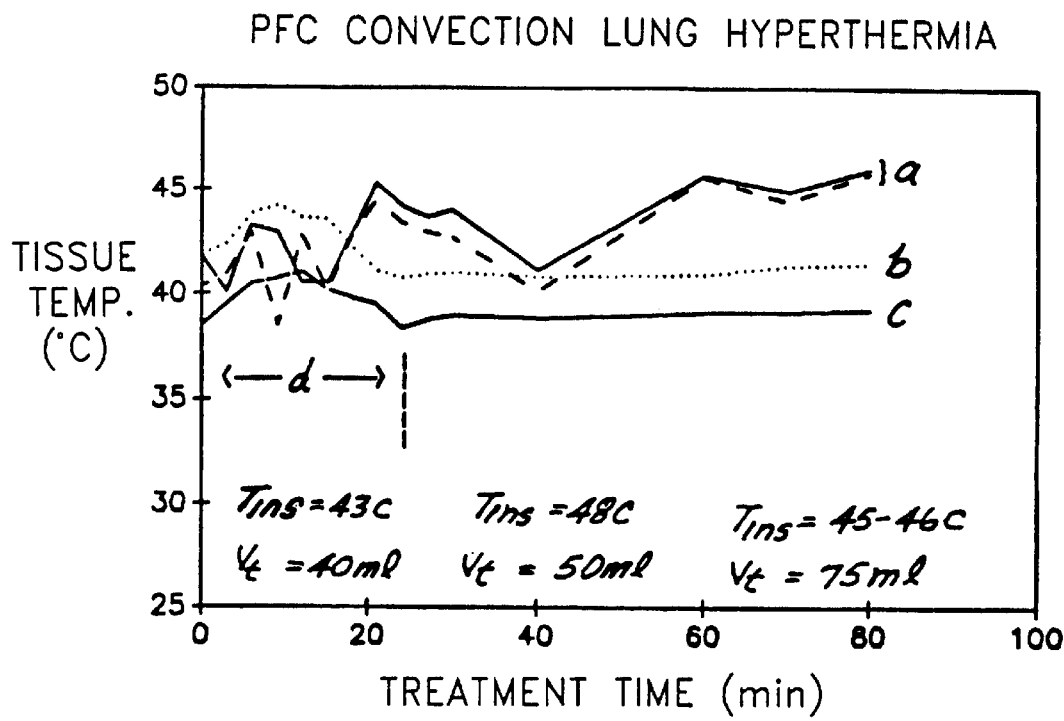
FIG. 30 is a graph of tissue temperature (°C.) versus treatment time (min), demonstrating perfluorocarbon convection lung hyperthermia as a function of tidal volume and liquid inspiration temperature.

FIG. 30 shows the temperature history data for the convective lung hyperthermia experiment. The setup period was used for establishing proper placement and sealing of the liquid delivery catheter, for proper temperature probe placement, and to assess the response of the lung to LLCH parameter changes. It was found that the very thin wall (≈2 mil) vinyl air cuffs on the available bifurcated catheters had very little structural integrity at the elevated liquid temperatures required of the hyperthermic treatment. As such, the catheters provided adequate, but not high quality, sealing. Although this had very little physiological impact (since the gas ventilation of the remaining lung was quite adequate), it did result in diminished heat transfer rates. The development of a suitable liquid delivery catheter was therefore mandated.

During the experiment, the heat transfer to the lung segment was varied by changing both the inspiratory liquid temperature ($T_{ins}$) and the tidal volume ($V_t$) under constant cycling (5 "breaths" per minute) conditions. Beginning with a low $T_{ins}$, low $V_t$ condition (43° C., 40 ml), it was found that temperatures in the therapeutic range slowly fell below hyperthermic values. Lung perfusion effectively cooled the lung under these conditions. However, increases in $T_{ins}$ and $V_t$ overcame this decline, bringing temperatures back up above 45° C. (t ≈60 minutes). Once the lung has reached the desired therapeutic temperature, the $T_{ins}$ and $V_t$ settings were adjusted downward to maintain good steady state hyperthermia (t>60 min).

Noteworthy Trends

First, the temperature probes in the center of the lung segment interstitium (spaced 2–3 cm apart) consistently were within 0.5° C. of each other at the higher tidal flows (t>60 min), and were usually within 1° C. of each other at the lower flows (t<40 min). Therefore, spatially uniform heating can readily be achieved and controlled via the tidal flow. Secondly, the rates of lung temperature increase shown during the experiment (≈0.25 C/min) are much more sluggish than rates which should occur at similar $T_{ins}$ values in a properly designed clinical device. This is due to the aforementioned compromised heat transfer from the leaky catheter cuff. Indeed, much higher rates were found during the setup period prior to cuff leakage (≈1 C/min for t<25 min). Lastly, it should be noted that steady state lung temperatures closely tracked $T_{ins}$, which was measured outside the animal in the liquid circuit. By placing a temperature sensor at the distal end of the catheter, at the entrance to the heated lung lobe or segment, the lung temperatures should be known with a high degree of certainty. This is significant in that there should be no need for invasive lung thermometry during the subject treatment.

Example 8

Ultrasound Imaging for Liquid-Filled Lung Procedures

The presence of liquid in the lung theoretically makes possible the use of ultrasound imaging, both for viewing lung structures and for use in conjunction with the ultrasound and convection treatments. Both in vitro and in vivo ultrasound imaging experiments were performed on perfluorocarbon-filled lungs as part of the animal studies described above. The diagnostic imaging system was a commercial clinical system (Diasonics) capable of sector-scanned images at frequencies from 3 to 7 MHz. B-scan images were obtained on exteriorized perfluorocarbon-filled lung lobes and on lung lobes viewed through the rib cage and intrathoracically.

Consistent with the ultrasound results discussed previously, it was found that the increased attenuation and scattering of the very high diagnostic frequencies (3–7 MHz) rendered the diagnostic value of imaging deep lung structures through liquid-filled lung parenchyma poor. The imaging of structures through liquid-filled lung parenchyma may be the one area where saline-filling of lungs provides a distinct advantage (due to matched sound speeds).

The foremost advantages of diagnostic ultrasound imaging in the present application are for monitoring the lung-filling process and for confirming the integrity of the acoustic path. This conclusion is based on the distinct ultrasound images which were obtained when lung lobes reached gas-free or near-gas-free states.

Example 9

Liquid-Filled Lung Hyperthermia and Chemotherapy

The prospects for using perfluorocarbon liquids as drug delivery vehicles may be quite favorable since commercial examples of fluoropharmaceuticals are many and diverse [60]. In addition, simultaneous locally delivered anesthesia in the treated tissue should also be possible via liquid delivery (though systemic anesthetic effects may also result). Although anesthetic use is often contraindicted in hyperthermia for safety reasons, because the maximum temperature in the lung may be set by the clinician with confidence in the subject (especially convection) treatments, simultaneous anesthesia may be feasible in this procedure. Conicidentally, fluorine-containing inhalation anesthetics account for the largest volume of fluoro-compounds sold for purposes that are nonindustrial [60].

Example 10

Ultrasound Intracavitary Applicator (ICA) Experiments

FIG. 4 shows a schematic of a representative applicator head. A thin-walled piezoelectric ceramic cylinder (≈1.0 MHz resonance) was longitudinally and circumferentially sectioned into four separate power transducers with 120° and 240° included angles, respectively. The multiple-transducer approach provided flexible heating patterns. In these studies transducers 120 and 122 were driven in parallel (forming a synchronous pair), as were 124 and 126. Depending upon whether each pair of both were driven, either 120°, 240°, or a full 360° of heating could be achieved along the length of the cylinder. The transducers were mounted in an applicator with self-contained cooling and an integral water bolus for sound coupling, as depicted in FIG. 6. The diameter of this first engineering prototype ICA transducer was 16 mm. Smaller cylinders more suitable for bronchial applications, however, can be readily made.

The applicator was mounted on a long (1 meter), flexible tubular shaft which housed the inlet and exit flow channels to the coupling bolus, as well as the RF power cables to the transducer. The water coolant flow dissipated heat to a maximum power of 100 Watts. The flow system was also characterized for pressure drop vs. flow rate to assure that acceptable pressure drops could be maintained in the long, narrow coolant channels.

Figure 31:
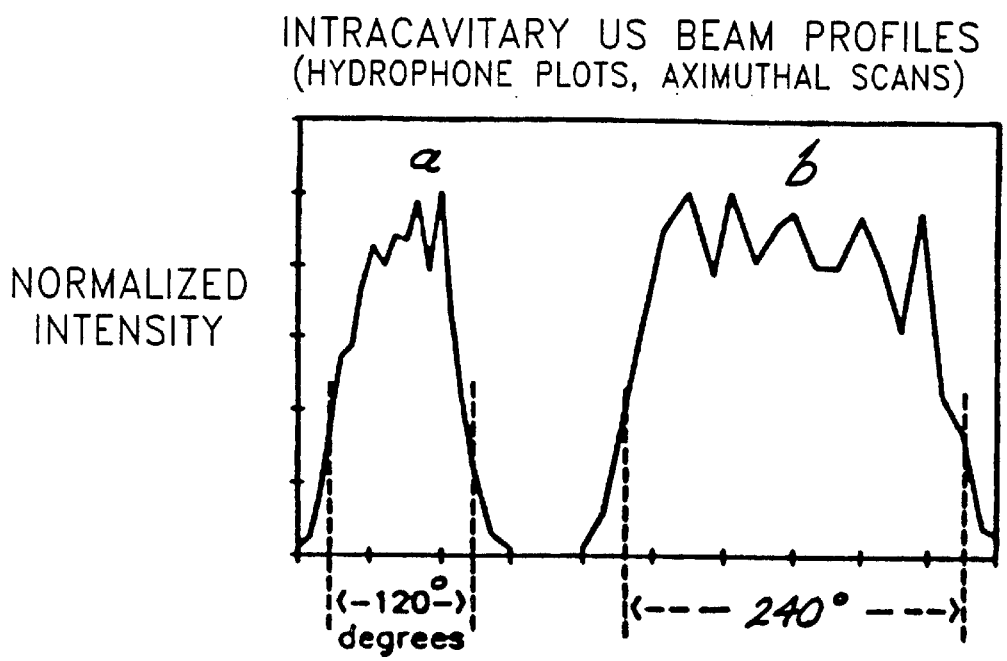
FIG. 31 is a graphical depiction of ultrasound beam profiles from representative intracavitary applicators.
Figure 32:
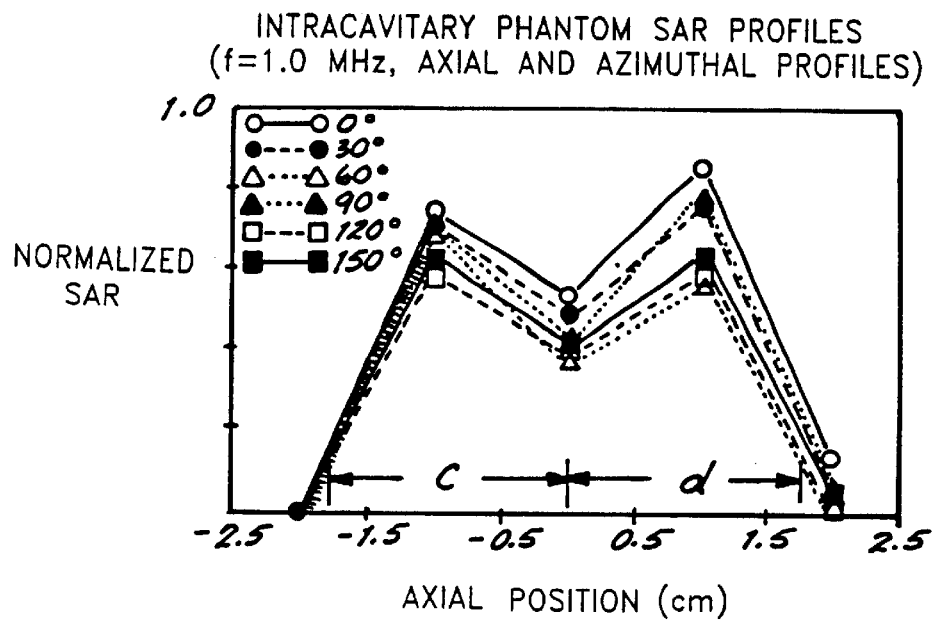
FIG. 32 is a graphical depiction of intracavitary phantom SAR profiles.
Figure 33:
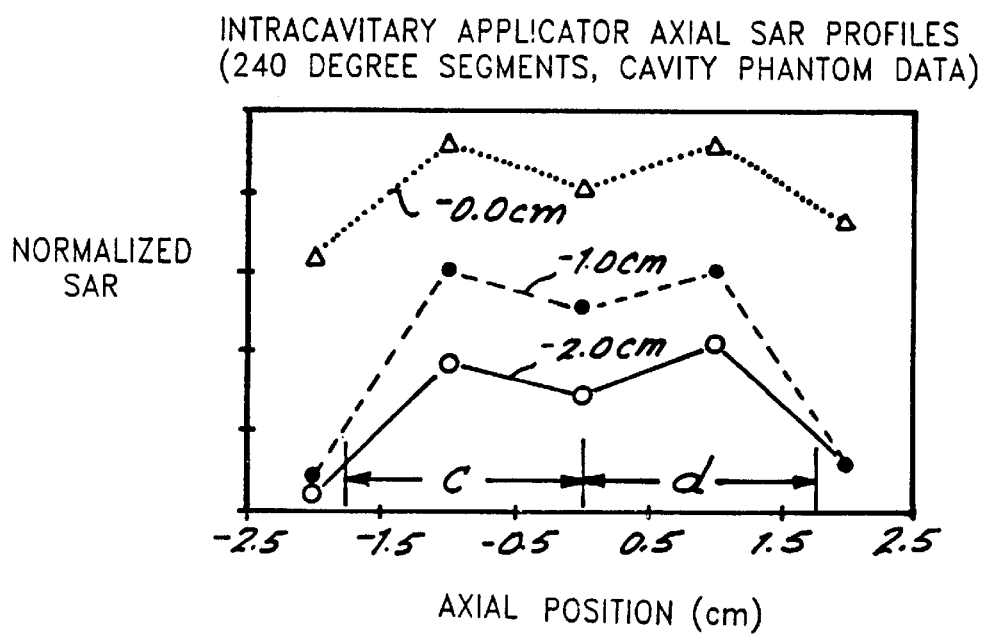
FIG. 33 is a graphical depiction of intracavitary applicator axial SAR profiles.

The ultrasound beam quality was mapped in an acoustic test tank, while the thermal performance of the device was evaluated in a specially constructed body cavity phantom. FIG. 31 shows the acoustic intensity mapped (via hydrophone) in water along the axial direction (z) of the transducer, 2 cm from the surface and in the middle of the 240° arc of energized transducers 124 and 126. FIG. 32 presents SAR patterns measured in tissue-equivalent cavity phantoms by needle thermocouple probes at five axial positions and several azimuthal angles (measured from the center of the 240° arc of transducers 124 and 126. FIG. 33 shows the depth (radially outward) heating patterns in the phantom from the surface to 2 cm into the phantom tissue. The 100-Watt maximum power employed is more than will be needed for most applications.

Example 11

Liquid-Filled Lung Convection Hyperthermia (LLCH) System

FIG. 34 schematically shows a representative LLCH system. The system is constructed under requirements applicable to clinical use. It is designed to maintain complete sterility of the liquids and catheters, and is modular and portable for convenient use in either a surgical theater or hyperthermia/oncology suite. The LLCH system provides heated, temperature-controlled perfluorocarbon liquid to the patient in either degassed or oxygenated form (partially degassed liquid states are also possible). To impose controlled lung temperatures and heat transfer rates, the tidal volume and "ventilation" frequency (cycling rate of the fluid into and out of the lung), and the input liquid temperature are controlled by the operator. To insure sterility, the unit employs roller-type peristaltic pumps which completely contain the liquid in sterile tubing. Similarly, valves, fluid fittings, and reservoirs are easily replaced and sterilizable, or disposable. The inspiratory and expiratory flows, system liquid temperatures and components status are monitored and controlled by a central computer. The computer serves as the operator console during treatment, recording and displaying LLCH system parameters and invasive temperature probe data, and is also a work station for data playback and post-treatment analyses.

Example 12

Pulmonary Administration of Drugs

Cardiovascular and Airway Smooth Muscle Effect

This Example demonstrates a technique for directly delivering biologically active agents (i.e., acetylcholine, epinephrine, priscoline, sodium bicarbonate and sodium nitroprusside) into a patient's cardiopulmonary system, via the patient's pulmonary air passages.

Using previously developed perfluorochemical (PFC) ventilation techniques, similar to those disclosed in Shaffer, *A Brief Review: Liquid Ventilation*, and Wolfson, et al., *A Experimental Approach for the Study of Cardiopulmonary Physiology During Early Development*, (see, notes 3 and 35, respectively, of literature citations, infra), pulmonary gas exchange and acid-base balance were maintained in anesthetized and tracheotomized young cats.

When testing the dose-dependency effect of the pulmonary administration of acetylcholine [ACh], the effect after the administration of the drug (expressed as a percentage of the baseline), as a function of the concentration of the drug, was monitored.

Here, the ACh was dispersed in the PFC liquid medium. The initial amount of ACh dispersed in the PFC liquid was 0.01 mg per each kilogram of the laboratory animal's body weight.

The PFC/ACh liquid medium was then introduced directly into the animal's pulmonary air passages, via the endotracheal tube, during the inspiratory phase of PFC liquid ventilation.

Each of the animals tested had at least one of the following parameters recorded before, during and after the pulmonary administration of the drug: (a) heart rate (bpm), (b) mean arterial pressure (mm Hg), and (c) tracheal pressure (cm water). The averages for each of these recorded parameters were then calculated, depending upon the number of cats tested. These calculated values are plotted on the graph in FIG. 35.

In addition to the above, the following parameters were also monitored and/or controlled: tidal volume, inspiratory and expiratory liquid flow rate, arterial chemistry, pulmonary compliance and resistance, and/or breathing frequency.

The dosage of ACh was then incrementally increased from 0.01 mg/kg up to 1.0 mg/kg. For each incremental increase, the animals tested had at least one of the aforementioned parameters recorded before and after the pulmonary administration of the drug.

Also for each incremental increase, the averages for each recorded parameter were calculated and plotted on the graph in FIG. 35.

Referring to FIG. 35, the data plotted therein demonstrates that, as a function of increasing the concentration of ACh in the inspired PFC liquid, typical dose-dependent cholinergic responses to ACh showed progressive decreases in mean arterial pressure (i.e., reflecting vasodilation) and heart rate, and a progressive increase in the peak tracheal pressure (i.e., reflecting broncho-constriction).

Another way in which the effect of the pulmonary administration of ACh was tested was by monitoring carotid pressure, as a function of time, before, during and after the pulmonary administration of the drug. Here, 0.6 mg/kg of ACh was dispersed in the PFC liquid medium. The PFC/ACh liquid medium was then introduced directly into the animal's pulmonary air passages, via the endotracheal tube, during the inspiratory phase of PFC liquid ventilation.

A tracing of the animal's carotid pressure, before, during and after the pulmonary administration of ACh, demonstrates, among other things, that (a) the carotid pressure decreased by about 40 mm Hg after the drug was administered; (b) the decrease in carotid pressure began almost instantaneously after the drug was administered; and (c) the total time necessary to decrease the carotid pressure by about 40 mm Hg was about 10 seconds.

Yet another way in which the effect of the pulmonary administration of ACh was tested was by monitoring tracheal pressure, as a function of time, before, during and after the pulmonary administration of the drug.

Here, 0.6 mg/kg of ACh was dispersed in the PFC liquid medium. The PFC/ACh liquid medium was then introduced directly into the animal's pulmonary air passages, via the endotracheal tube, during the inspiratory phase of PFC liquid ventilation.

An observation of the animal's tracheal pressure, before, during and after the pulmonary administration of tracheal pressure (cm water) increased by about 6 mm Hg after the drug was administered; (b) the increase in tracheal pressure began almost instantaneously after the drug was administered; and (c) the total time necessary to increase the tracheal pressure (cm water) by about 5 mm Hg was about 20 seconds.

When testing the dose-dependency effect of the pulmonary administration of epinephrine [Epi], the effect after the administration of the drug (expressed as a percentage of the baseline), as a function of the concentration of the drug, was monitored.

Here, the Epi was dispersed in the PFC liquid medium. The initial amount of Epi dispersed in the PFC liquid was 0.01 mg per each kilogram of the laboratory animal's body weight.

The PFC/Epi liquid medium was then introduced directly into the animal's pulmonary air passages, via the endotracheal tube, during the inspiratory phase of PFC liquid ventilation.

Each of the animals tested had at least one of the following parameters recorded before and after the pulmonary administration of the drug: (a) heart rate (bpm), (b) mean arterial pressure (mm Hg), and (c) tracheal pressure (cm water). The averages for each of these recorded parameters were then calculated, depending upon the number of cats tested. These calculated values are plotted on the graph in FIG. 36.

The dosage of Epi was then incrementally increased from 0.01 mg/kg up to 1.0 mg/kg. For each incremental increase, the animals tested had at least one of the aforementioned parameters recorded before and after the pulmonary administration of the drug.

Also for each incremental increase, the averages for each recorded parameter were calculated and plotted on the graph in FIG. 36.

Referring to FIG. 36, the data plotted therein demonstrates that, as a function of increasing the concentration of Epi in the inspired PFC liquid, typical dose-dependent sympathomimetic responses to Epi showed increases in mean arterial pressure (i.e., reflecting vasoconstriction) and heart rate, and a decrease in peak tracheal pressure (i.e., reflecting bronchodilation).

Another way in which the effect of the pulmonary administration of Epi was tested was by monitoring the change in mean arterial pressure and heart rate resulting from drug delivery.

Here, 0.50 mg/kg of Epi was dispersed in the PFC liquid medium. The PFC/Epi liquid medium was then introduced directly into the animal's pulmonary air passages, via the endotracheal tube, during the inspiratory phase of PFC liquid ventilation.

An observation of the animal's tracheal pressure, before, during and after the pulmonary administration of Epi, demonstrates, among other things, a 31% decrease after the drug was administered. Moreover, an observation of the animal's heart rate, before, during and after the pulmonary administration of Epi, demonstrates, among other things, a 33% increase after the drug was administered.

When testing the dose-dependency effect of the pulmonary administration of priscoline [P], the effect after the administration of the drug (expressed as a percentage of the baseline), as a function of the concentration of the drug, was monitored.

Here, the P was dispersed in the PFC liquid medium. The initial amount of P dispersed in the PFC liquid was 4 mg.

The PFC/P liquid medium was then introduced directly into the animal's pulmonary air passages, via the endotracheal tube, during the inspiratory phase of PFC liquid ventilation.

Each of the animals tested weighed approximately 3 kg. Each of these test animals had at least one of the following parameters recorded before and after the pulmonary administration of the drug: (a) heart rate (bpm), (b) mean arterial pressure (mm Hg), and (c) right ventricular pressure.

The averages for each of the aforementioned recorded parameters were then calculated, depending upon the number of cats tested. These calculated values are plotted on the graph in FIG. 37.

The dosage of P was then incrementally increased from 4 mg up to 12 mg. For each incremental increase, the animals tested had at least one of the aforementioned parameters recorded before, during and after the pulmonary administration of the drug.

Also for each incremental increase, the averages for each recorded parameter were calculated and plotted on the graph in FIG. 37.

Referring to FIG. 37, the data plotted therein demonstrates that, as function of increasing the concentration of P in the inspired PFC liquid, typical dose-dependent responses to P showed decreases in mean arterial pressure (i.e., reflecting vasodilation) and right ventricular pressure (i.e., reflecting systemic and pulmonary vasodilation). The heart rate remained fairly constant.

Another way in which the effect of the pulmonary administration of P was tested was by monitoring carotid pressure, as a function of time, before, during and after the pulmonary administration of the drug.

Here, 12 mg of P was dispersed in the PFC liquid medium. The PFC/P liquid medium was then introduced directly into the animal's pulmonary air passages, via the endotracheal tube, during the inspiratory phase of PFC liquid ventilation.

A tracing of the animal's carotid pressure, before, during and after the pulmonary administration of P, demonstrates, among other things, that (a) the carotid pressure decreased by about 30 mm Hg after the drug was administered; (b) the decrease in carotid pressure began almost instantaneously after the drug was administered; and (c) the total time necessary to decrease the carotid pressure by about 30 mm Hg was about 10 seconds.

When testing the absorption effect of the pulmonary administration of sodium bicarbonate [SBi], the concentration of SBi in the animal's blood, as a function of time, was monitored.

Here, 10 mEq of SBi was dispersed in the PFC liquid medium. The PFC/SBi liquid medium was then introduced directly into the animal's pulmonary air passages, via the endotracheal tube, during the inspiratory phase of PFC liquid ventilation.

An observation of the concentration of SBi present in the animal's blood (monitored as a function of mEq/L) 30 and 120 seconds after the pulmonary administration of SBi, demonstrates, among other things, a respective 4.7% and 20.9% absorption level.

When testing the physiological effect of the pulmonary administration of sodium nitroprusside [SNi], the physiological change in the animal's arterial pressure and heart rate, after the administration of the drug, was monitored.

Here, 6 mg/kg of SNi was dispersed in the PFC liquid medium. The PFC/SNi liquid medium was then introduced directly into the animal's pulmonary air passages, via the endotracheal tube, during the inspiratory phase of PFC liquid ventilation.

An observation of the animal's heart rate, before, during and after the pulmonary administration of SNi, demonstrates, among other things, that it did not significantly change, increase after the drug was administered. Moreover, an observation of the animal's arterial pressure; before, during and after the pulmonary administration of SNi, demonstrates, among other things, a 24% decrease after the drug was administered.

It was observed from the above that the pulmonary administration of drugs by liquid ventilation is an effective approach for directly delivering therapeutic agents to the pulmonary and/or systemic systems.

Conclusions

The foregoing research was highlighted by the first in vivo demonstrations of both acoustic and convective hyperthermia of the lung, here in a suitably large animal model. Controlled and sustained therapeutic temperatures were maintained with relatively few complications. These experiments, complemented by laboratory bench and in vitro acoustic measurements with perfluorocarbon liquids, identified the important clinical requirements for liquid-filled lung ultrasound and convection hyperthermia. Among these are a) lower ultrasound frequencies than traditionally used for soft tissue heating are required, b) traditional bifurcated bronchial catheters are inadequate, mainly due to their thin-walled air cuffs and lack of temperature and pressure instrumentation, and c) the use of degassed perfluorocarbon liquids greatly facilitates the filling of lungs. Of tremendous practical significance are the observations that d) diagnostic ultrasound imaging can be very helpful in assessing the lung filling and the acoustic path available, and e) invasive thermometry will likely not be required for the convection hyperthermia treatments. Additionally, the fundamental fluid and thermal design ranges appropriate to the ultrasound treatment, including the range of inflation pressures, temperatures and tidal volumes, were determined.

Perfluorocarbon liquids have several unique properties. Measurable nonlinear acoustical behavior and scattering in the range of powers suitable to hyperthermia were found in laboratory and animal tests. While dictating the use of lower ultrasound frequencies, these characteristics can be advantageous for spatial smoothing of near field beam patterns and may be able to be exploited for their potential to produce localized enhanced absorption with focused ultrasound beams. In addition, the high gas solubility of perfluorocarbons should serve to suppress acoustic cavitation in the liquid by retarding rapid gas saturation.

The salient design requirements for clinical devices for 1) fluid processing and delivery systems suitable for liquid-filled lung hyperthermia procedures, 2) intracavitary ultrasound applicators for broncho-tracheal tumors, and 3) low-frequency external ultrasound applicators were also determined.

In addition to the above, the foregoing research also demonstrates the operability and significant utility of pulmonary administered therapeutic agents through a liquid lavage/ventilation process.

Example 13
Biomechanical Uses of Pulmonary Liquids

The invention encompasses using liquids in the lung for their biomechanical effects, principally those resulting from their ability to uniformly occupy lung tissue in cases where gas cannot (e.g., where airways are collapsed or atalectic) and therefore exert pressure forces which are safer and more evenly distributed than gas. Such pressure effects exerted by an incompressible fluid (again, which can be used simultaneously with ventilation, drug delivery or lavage) can be used to reposition, reshape (temporarily, or permanently if repeatedly applied), or control the motion of lung and surrounding tissues and organs. Representative uses include:

1) Repositioning the lungs and abdominal organs in neonatal diaphragmatic hernia, a condition in which babies are sometimes born with the contents of their abdominal cavity displaced well up into the chest, precluding efficient breathing and having other complications due to the organs being out of place. Liquid inflation of the lungs with simultaneous ventilation provides a method of easing the lungs and surrounding displaced tissues back into more normal locations, either with or without simultaneous surgery to help correct the problem.

2) Suppressing the motion of lungs for short times (either unilaterally, for a single lung, lobe or segment, or bilaterally for both lungs) for various reasons. For example, to decrease motion artifacts in various diagnostic imaging modalities, in order to still tissues for the placement of instruments, in order to hold the lung temporarily still during short acting therapies, e.g., radiotherapy of lung tumors, etc.

3) Inflation of lungs for repairing pneumothorax in which the air leak into the pleural space is through the outer pleural membranes (i.e., not induced by leaks from the lung itself). This method may be superior to using gas inflation of the lung (with or without applying a vacuum on the pleural space) when the lung condition is not conducive to uniform expansion or inflation (e.g., from disease or injury). A combination of liquid inflation, followed by maintenance of constant pressure to hold the shape of the lung, with or without a vacuum applied to the pleural space, could be used.

4) Use of liquid pressure to "mechanically" (not pharmacologically) alter pulmonary blood perfusion (i.e., via hydrostatic pressure and pulmonary vascular resistance effects), for instance to alter the pulmonary delivery of drugs. For example, changing the gravitationally induced top-to-bottom perfusion gradient in the lung may promote more even (e.g., for liquids with densities close to blood) or simply a different and more desired distribution of its absorption over the lung volume. Notably, perfluorocarbon liquids are much denser than saline (the liquid most used in physiology).

Example 14
Mechanical Effects of Ultrasound

The invention also encompasses the use of ultrasound to produce localized mechanical (nonthermal) effects in liquid-filled pulmonary spaces. Ultrasound beams can be focused or scanned on portions of pulmonary tissue (intercostally, intracavitarily, or intraoperatively) to take advantage of nonthermal effects. By employing appropriate powers and frequencies (typically lower than those used for hyperthermia) ultrasound can be used to agitate and mechanically stir (through a phenomenon termed "acoustic streaming") local regions of the liquid in the pulmonary air spaces, liquid which is in intimate contact with lung tissue, and which may or may not be carrying drugs. These mechanical effects can, by inducing localized convective motion in the fluid (on a scale varying from tracheal to alveolar characteristic dimensions), a) enhance drug transport in and to the lungs, b) improve the flushing of substances out of the lung when using lavage, c) breakup "plugged regions" of the airways by inducing high frequency oscillations in the liquid and in movable substances (e.g., mucus, proteinaceous fluids, inhaled particulates, etc.).

Example 15
Noncancer Hyperthermia

The invention also encompasses ultrasound hyperthermia (using all the ultrasound methods and devices disclosed above for cancer) for nonlung cancer applications, for example, to a) produce localized drug action caused by higher local temperatures at desired locations, or b) to make fluid substances which are blocking airways less viscous through heating them, and thus enhance their removal, say through lavage, with or without mechanical effects of ultrasound being exploited.

While representative and preferred embodiments of the invention have been described and illustrated, it is to be understood that, within the scope of the appended claims, various changes can be made therein. Hence, the invention can be practiced in ways other than those specifically described herein.

The embodiments of the invention in which an exclusive property or privilege is claimed are defined as follows:

What is claimed is:

1. A method for the delivery of a therapeutic or diagnostic biological agent to pulmonary air passages of a patient in need thereof comprising the steps of:
    combining said therapeutic or diagnostic biological agent in the form of a solid or immiscible liquid with a perfluorochemical liquid carrier to provide a pharmaceutical preparation; and
    administering said pharmaceutical preparation to the pulmonary air passages of said patient.

2. The method of claim 1 wherein the biological agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

3. The method of claim 1 wherein said perfluorochemical liquid carrier comprises a perfluorocarbon having a boiling point greater than about 55° C.

4. The method of claim 1 wherein said perfluorochemical liquid carrier is selected from the group consisting of FC-84, FC-72, RM-82, FC-75, RM-101, FC-43, RM-175, FC-5311, FC-5312, trimethylbicyclononane, dimethyladamantine and perfluorodecalin, or a combination thereof.

5. The method of claim 1 wherein said pharmaceutical preparation is oxygenated.

6. The method of claim 1 in which the pharmaceutical preparation is administered at a temperature above the body temperature of the patient.

7. The method of claim 1 in which the pharmaceutical preparation is administered at a temperature below the body temperature of the patient.

8. The method of claim 1 wherein the biological agent is a solid.

9. The method of claim 8 wherein the biological agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

10. The method of claim 8 wherein the biological agent comprises a chemotherapeutic agent.

11. The method of claim 8 wherein the biological agent comprises an antibiotic.

12. The method of claim 8 wherein the biological agent comprises a bronchodilator.

13. The method of claim 1 wherein the biological agent is in the form of an immiscible liquid.

14. The method of claim 13 wherein the pharmaceutical preparation comprises an emulsion.

15. The method of claim 14 wherein the biological agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

16. The method of claim 14 wherein the biological agent comprises a chemotherapeutic agent.

17. The method of claim 14 wherein the biological agent comprises an antibiotic.

18. The method of claim 14 wherein the biological agent comprises a bronchodilator.

19. The method of claim 14 wherein the biological agent is dispersed in the perfluorochemical liquid carrier.

20. The method of claim 19 wherein the biological agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

21. The method of claim 13 wherein the immiscible liquid biological agent comprises the therapeutic or diagnostic agent in an aqueous medium.

22. The method of claim 21 wherein said therapeutic or diagnostic agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

23. A method for the delivery of a therapeutic or diagnostic biological agent to pulmonary air passages of a patient in need thereof comprising the steps of:
    combining a liquid perfluorochemical with an immiscible liquid to form an emulsion wherein said emulsion further comprises at least one therapeutic or diagnostic biological agent; and
    administering the emulsion to the pulmonary air passages of said patient.

24. The method of claim 23 wherein said liquid perfluorochemical comprises a perfluorocarbon having a boiling point greater than about 55° C.

25. The method of claim 23 wherein said perfluorochemical liquid carrier is selected from the group consisting of FC-84, FC-72, RM-82, FC-75, RM-101, FC-43, RM-175, RC-5311, FC-5312, trimethylbicyclononane, dimethyladamantine and perfluorodecalin, or a combination thereof.

26. The method of claim 23 wherein said emulsion is oxygenated.

27. The method of claim 23 in which the emulsion is administered at a temperature above the body temperature of the patient.

28. The method of claim 23 in which the emulsion is administered at a temperature below the body temperature of the patient.

29. The method of claim 23 wherein said immiscible liquid is aqueous.

30. The method of claim 23 wherein the biological agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

31. The method of claim 23 wherein the biological agent comprises a chemotherapeutic agent.

32. The method of claim 23 wherein the biological agent comprises an antibiotic.

33. The method of claim 23 wherein the biological agent comprises a bronchodilator.

34. The method of claim 23 wherein the biological agent is dispersed in the liquid perfluorochemical.

35. The method of claim 34 wherein the biological agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

36. The method of claim 34 wherein the biological agent comprises a chemotherapeutic agent.

37. The method of claim 34 wherein the biological agent comprises an antibiotic.

38. The method of claim 34 wherein the biological agent comprises a bronchodilator.

39. The method of claim 23 wherein the liquid comprises the therapeutic or diagnostic agent in an aqueous medium.

40. The method of claim 39 wherein said therapeutic or diagnostic agent is selected from the group consisting of antibody-linked radionuclides, vasoconstrictors, vasodilators, bronchoconstrictors, bronchodilators, anti-cancer agents, surfactants, steroids, antibiotic agents, chemotactic agents, chemotherapeutic agents, contrast agents, antioxidants and antiproteases, or a combination thereof.

41. A method for the delivery of a therapeutic or diagnostic biological agent to pulmonary air passages of a patient in need thereof comprising the steps of:

combining a liquid perfluorochemical with at least one therapeutic or diagnostic biological agent in solid form to provide a dispersion; and administering the dispersion to the pulmonary air passages of said patient.

42. The method of claim 41 wherein said liquid perfluorochemical comprises a perfluorocarbon having a boiling point greater than about 55° C.

43. The method of claim 41 wherein said liquid perfluorochemical is selected from the group consisting of FC-84, FC-72, RM-82, FC-75, RM-101, FC-43, RM-175, FC-5311, FC-5312, trimethylbicyclononane, dimethyladamantine and perfluorodecalin, or a combination thereof.

44. The method of claim 41 wherein said dispersion is oxygenated.

45. The method of claim 41 wherein the solid biological agent comprises a powder.

46. The method of claim 41 wherein the solid biological agent is selected from the group consisting of antibody-linked radionuclides, vasoconstrictors, vasodilators, bronchoconstrictors, bronchodilators, anti-cancer agents, surfactants, steroids, antibiotic agents, chemotactis agents, chemotherapeutic agents, contrast agents, antioxidants and antiproteases, or a combination thereof.

47. The method of claim 41 wherein the solid biological agent comprises a chemotherapeutic agent.

48. The method of claim 41 wherein the solid biological agent comprises an antibiotic.

49. The method of claim 41 wherein the solid biological agent comprises a bronchodilator.

50. The method of claim 41 wherein the solid biological agent comprises a surfactant.

* * * * *

UNITED STATES PATENT AND TRADEMARK OFFICE
CERTIFICATE OF CORRECTION

PATENT NO.   : 6,242,472 B1
DATED        : June 5, 2001
INVENTOR(S)  : Sekins et al.

It is certified that error appears in the above-identified patent and that said Letters Patent is hereby corrected as shown below:

Column 44,
Line 49, "RC-5311" should be -- FC-5311 --.

Signed and Sealed this

Fifth Day of March, 2002

Attest:

JAMES E. ROGAN
Attesting Officer    Director of the United States Patent and Trademark Office